US007850962B2

(12) United States Patent
Teeling et al.

(10) Patent No.: US 7,850,962 B2
(45) Date of Patent: Dec. 14, 2010

(54) HUMAN MONOCLONAL ANTIBODIES AGAINST CD20

(75) Inventors: Jessica Teeling, Swaithling (GB); Martin Glennie, Swaithling (GB); Paul Parren, Odijk (NL); Arnout F. Gerritsen, Bunnik (NL); Sigrid Ruuls, De Bilt (NL); Yvo Graus, Odijk (NL); Jan van de Winkel, Zeist (NL)

(73) Assignee: Genmab A/S, Copenhagen-K (DK)

( * ) Notice: Subject to any disclaimer, the term of this patent is extended or adjusted under 35 U.S.C. 154(b) by 330 days.

(21) Appl. No.: 11/578,818

(22) PCT Filed: Apr. 20, 2005

(86) PCT No.: PCT/DK2005/000270

§ 371 (c)(1),
(2), (4) Date: May 29, 2008

(87) PCT Pub. No.: WO2005/103081

PCT Pub. Date: Nov. 3, 2005

(65) Prior Publication Data
US 2008/0260641 A1    Oct. 23, 2008

(30) Foreign Application Priority Data
Apr. 20, 2004    (DK)    .................... PA 2004 00627

(51) Int. Cl.
*A61K 39/395* (2006.01)
*A61K 39/00* (2006.01)
*G01N 33/53* (2006.01)
*G01N 33/567* (2006.01)
*G01N 33/574* (2006.01)
*G01N 33/00* (2006.01)
*C07K 16/00* (2006.01)
*C12P 21/08* (2006.01)
*C07K 17/00* (2006.01)
*C07K 17/14* (2006.01)

(52) U.S. Cl. .............. 424/130.1; 424/131.1; 424/133.1; 424/135.1; 424/141.1; 424/178.1; 435/7.1; 435/7.21; 435/7.23; 435/7.24; 530/387.1; 530/387.2; 530/387.3; 530/388.1; 530/388.7; 530/391.1; 530/391.3; 530/391.7

(58) Field of Classification Search ........................ None
See application file for complete search history.

(56) References Cited

U.S. PATENT DOCUMENTS

| 5,182,368 | A | 1/1993 | Ledbetter et al. |
|---|---|---|---|
| 5,247,069 | A | 9/1993 | Ledbetter et al. |
| 5,506,126 | A | 4/1996 | Seed et al. |
| 5,540,926 | A | 7/1996 | Aruffo et al. |
| 5,595,721 | A | 1/1997 | Kaminski et al. |
| 5,658,570 | A | 8/1997 | Newman et al. |
| 5,681,722 | A | 10/1997 | Newman et al. |
| 5,693,780 | A | 12/1997 | Newman et al. |
| 5,736,137 | A | 4/1998 | Anderson et al. |
| 5,750,105 | A | 5/1998 | Newman et al. |
| 5,756,096 | A | 5/1998 | Newman et al. |
| 5,770,429 | A | 6/1998 | Lonberg et al. |
| 5,776,456 | A | 7/1998 | Anderson et al. |
| 5,786,456 | A | 7/1998 | Ledbetter et al. |
| 5,830,731 | A | 11/1998 | Seed et al. |
| 5,843,398 | A | 12/1998 | Kaminski et al. |
| 5,843,439 | A | 12/1998 | Anderson et al. |
| 5,849,898 | A | 12/1998 | Seed et al. |
| 5,945,513 | A | 8/1999 | Aruffo et al. |
| 6,015,542 | A | 1/2000 | Kaminski et al. |
| 6,090,365 | A | 7/2000 | Kaminski et al. |
| 6,111,093 | A | 8/2000 | Seed et al. |
| 6,120,767 | A | 9/2000 | Robinson et al. |
| 6,136,310 | A | 10/2000 | Hanna et al. |
| 6,183,744 | B1 | 2/2001 | Goldenberg |
| 6,218,525 | B1 | 4/2001 | Seed et al. |
| 6,224,866 | B1 | 5/2001 | Barbera-Guillem |
| 6,287,537 | B1 | 9/2001 | Kaminski et al. |
| 6,306,393 | B1 | 10/2001 | Goldenberg |
| 6,395,676 | B2 | 5/2002 | Blum et al. |
| 6,399,061 | B1 | 6/2002 | Anderson et al. |
| 6,455,043 | B1 | 9/2002 | Grillo-López |
| 6,696,550 | B2 * | 2/2004 | LaRosa et al. ......... 530/388.23 |
| 6,846,476 | B2 | 1/2005 | White |

(Continued)

FOREIGN PATENT DOCUMENTS

WO    WO 88/04936 A1    7/1988

(Continued)

OTHER PUBLICATIONS

Rudikoff, Giusti, Cook, and Scharff. Single amino acid substitution altering antigen binding specificity. Proceedings of the National Academy of Sciences, 1982. vol. 79, pp. 1979-1983.*

Mac Callum, Martin, and Thornton. Antibody-antigen interactions: contact analysis and binding site topography. Journal of Molecular Biology, 1996. vol. 262, pp. 732-745.*

De Pascalis, Iwahashi, Tamura, Padlan, Gonzales, Santos, Giuliano, Schuck, Schlom, and Kashmiri. Grafting of abbreviated complementarity determining regions containing specificity determining residues essential for ligand contact to engineer a less immunogenic humanzied monoclonal antibody. Journal of Immunology, 2002. vol. 169, pp. 3076-3084.*

(Continued)

*Primary Examiner*—Anne M. Gussow
(74) *Attorney, Agent, or Firm*—Hamilton, Brook, Smith & Reynolds, P.C.

(57) ABSTRACT

Isolated human monoclonal antibodies which bind to and inhibit human CD20, and related antibody-based compositions and molecules, are disclosed. Also disclosed are pharmaceutical compositions comprising the human antibodies, and therapeutic and diagnostic methods for using the human antibodies.

49 Claims, 17 Drawing Sheets

U.S. PATENT DOCUMENTS

| | | | |
|---|---|---|---|
| 6,849,425 B1 * | 2/2005 | Huse et al. | 435/69.1 |
| 6,896,885 B2 | 5/2005 | Hanna | |
| 7,378,503 B2 * | 5/2008 | Graus et al. | 530/387.1 |
| 2001/0018041 A1 | 8/2001 | Hanna et al. | |
| 2001/0033839 A1 | 10/2001 | Barbera-Guillem | |
| 2001/0056066 A1 | 12/2001 | Bugelski et al. | |
| 2002/0006404 A1 | 1/2002 | Hanna et al. | |
| 2002/0009427 A1 | 1/2002 | Wolin et al. | |
| 2002/0009444 A1 | 1/2002 | Grillo-López | |
| 2002/0012665 A1 | 1/2002 | Hanna | |
| 2002/0028178 A1 | 3/2002 | Hanna et al. | |
| 2002/0039557 A1 | 4/2002 | White | |
| 2002/0041847 A1 | 4/2002 | Goldenberg | |
| 2002/0048550 A1 | 4/2002 | Vallera et al. | |
| 2002/0058029 A1 | 5/2002 | Hanna | |
| 2002/0064823 A1 | 5/2002 | Welcher et al. | |
| 2002/0071807 A1 | 6/2002 | Goldenberg | |
| 2002/0128448 A1 | 9/2002 | Reff | |
| 2002/0150580 A1 | 10/2002 | Newman et al. | |
| 2002/0159996 A1 | 10/2002 | Hariharan et al. | |
| 2004/0167319 A1 | 8/2004 | Teeling et al. | |

FOREIGN PATENT DOCUMENTS

| | | |
|---|---|---|
| WO | WO 92/03918 A1 | 3/1992 |
| WO | WO 93/02108 A1 | 2/1993 |
| WO | WO 94/11026 A2 | 5/1994 |
| WO | WO 94/25585 A1 | 11/1994 |
| WO | WO 97/09351 A1 | 3/1997 |
| WO | WO 98/04281 A1 | 2/1998 |
| WO | WO 98/24884 A1 | 6/1998 |
| WO | WO 98/42378 A1 | 10/1998 |
| WO | WO 99/14353 A2 | 3/1999 |
| WO | WO 99/33485 A1 | 7/1999 |
| WO | WO 00/03733 A1 | 1/2000 |
| WO | WO 00/09160 A1 | 2/2000 |
| WO | WO 00/20864 A1 | 4/2000 |
| WO | WO 00/27428 A1 | 5/2000 |
| WO | WO 00/27433 A1 | 5/2000 |
| WO | WO 00/67796 A1 | 11/2000 |
| WO | WO 00/74718 A1 | 12/2000 |
| WO | WO 01/03734 A1 | 1/2001 |
| WO | WO 01/10460 A1 | 2/2001 |
| WO | WO 01/10462 A1 | 2/2001 |
| WO | WO 01/34194 A1 | 5/2001 |
| WO | WO 01/72333 A1 | 10/2001 |
| WO | WO 01/74388 A1 | 10/2001 |
| WO | WO 01/80884 A1 | 11/2001 |
| WO | WO 01/97843 A2 | 12/2001 |
| WO | WO 01/97858 A2 | 12/2001 |
| WO | WO 02/04021 A1 | 1/2002 |
| WO | WO 02/07783 A2 | 1/2002 |
| WO | WO 02/12437 A2 | 2/2002 |
| WO | WO 02/22212 A2 | 3/2002 |
| WO | WO 02/34790 A1 | 5/2002 |
| WO | WO 02/060484 A1 | 8/2002 |
| WO | WO 02/060485 A2 | 8/2002 |
| WO | WO 02/062946 A2 | 8/2002 |
| WO | WO 2004/035607 A2 | 4/2004 |

OTHER PUBLICATIONS

Casset, Roux, Mouchet, Bes, Chardes, Granier, Mani, Pugniere, Laune, Pau, Kaczorek, Lahana, and Rees. A peptide mimetic of an anti-CD4 monoclonal antibody by rational design. Biochemical and Biophysical Research Communications, 2003. vol. 307, pp. 198-205.*

Vajdos, Adams, Breece, Presta, De Vos, and Sidhu. Comprehensive functional maps of the antigen binding site of an anti-ErbB2 antibody obtained with shotgun scanning mutagenesis. Journal of Molecular Biology, 2002. vol. 320, pp. 415-428.*

Holm, Jafari, and Sundstrom. Functional mapping and single chain construction of the anti-cytokeratin 8 monoclonal antibody TS1. Molecular Immunology, 2007. vol. 44, pp. 1075-1084.*

Chen, Wiesmann, Fuh, Li, Christinger, Mc Kay, De Vos, and Lowman. Selection and analysis of an optimized anti-VEGF antibody: crystal structure of an affinity-matured Fab in complex with antigen. Journal of Molecular Biology, 1999. vol. 293, pp. 865-881.*

Wu, Nie, Huse, and Watkins. Humanization of a murine monoclonal antibody by simultaneous optimization of framework and CDR residues. Journal of Molecule Biology, 1999. vol. 294, pp. 151-162.*

Granziero, Krajewski, Farness, Yuan, Courtney, Jackson, Peterson, and Vitiello. Adoptive immunotherapy prevents prostate cancer in a transgenic animal model. European Journal of Immunology, 1999. vol. 29, pp. 1127-1138.*

Byers. What can randomized controlled trials tell us about nutrition and cancer prevention? CA Cancer Journal Clin. 1999. vol. 49, pp. 353-361.*

Mount and Gilliland. Emerging biological therapies in systemic lupus erythematosus. Clinical Pharmacology and Therapeutics, 2008. vol. 83, pp. 167-171.*

Perosa, Prete, Racanelli, and Dammacco. CD20 depleting therapy in autoimmune diseases: from basic research to the clinic. Journal of Internal Medicine, 2010. vol. 267, pp. 260-277.*

Johns, Doyle, Lipman, Cwynarski, Cleverly, Isaacson, Shaw, and Agarwal. Successful treatment of HIV-associated multicentric Castleman's disease and multiple organ failure with rituximab and supportive care: a case report. Journal of Medical Care Reports, 2010. vol. 4:32 (pp. 1-6).*

Edwards, J. C. W. And Cambridge, G., "Sustained Improvement in Rheumatoid Arthritis Following a Protocol Designed to Deplete B Lymphocytes," *Rheumatology*, 40:205-211 (2001).

Gazzano-Santoro, H., et al., "A Non-Radioactive Complement-Dependent Cytotoxicity Assay for Anti-CD20 Monoclonal Antibody," *Journal of Immunological Methods*, 202:163-171 (1997).

van Spriel, A. B., et al., "Immunotherapeutic Perspective for Bispecific Antibodies," *Immunology Today*, 21(8):391-397 (2000).

Supplemental European Search Report for EP 03609145.0 (PCT/US03/33057).

International Search Report for PCT/US03/33057.

Dechant, M., et al., "Novel Fully Human CD20 Antibodies with Different Mechanisms of Action." Blood, vol. 102, No. 11, p. 103a (Nov. 2003).

Teeling, J.L., et al., "Characterization of New Human CD20 Monoclonal Antibodies with Potent Cytolytic Activity Against Non-Hodgkin Lymphomas," Blood, W.B. Saunders Company, Orlando, FL., US, vol. 104, No. 6, pp. 1793-1800 (Sep. 2004).

Coiffier, B., "Monoclonal Antibodies Combined to Chemotherapy for the Treatment of Patients with Lymphoma," Blood Reviews, vol. 17, No. 1, pp. 25-31 (Mar. 2003).

Johnson, P.W., et al., "Rituximab: Mechanisms and Applications." British Journal of Cancer, vol. 85, No. 11, pp. 1619-1623 (Nov. 2001).

* cited by examiner rituximab

11B8

2C6 IgG1,κ anti-KLH rituximab

11B8

2C6 IgG1,κ anti-KLH

Figure 14

Variable Heavy chain sequence alignment

```
1         10        20        30        40        50
EVQLVESGGGLVQPGRSLRLSCAASGFTFDDYAMHWVRQAPGKGLEWVSGISWNSGSI    Germline VH3-20
AVQLVESGGGLVQPGRSLRLSCAASGFTFGDYTMHWVRQAPGKGLEWVSGISWNSGSI    2C6 V_H 60        70        80        90        100       110       120
GYADSVKGRFTISRDNAKNSLYLQMNSLRAEDTALYYCAKD----------------------    Germline VH3-20  (SEQ ID NO:73)
GYADSVKGRFTISRDNAKNSLYLQMNSLRAEDTALYYCTKDNQYGSGSTYGLGVWGQGTLVTVSS 2C6 V_H          (SEQ ID NO:74)
```

Variable Light chains sequence alignments

```
1         10        20        30        40        50
EIVLTQSPATLSLSPGERATLSCRASQSVSSYLAWYQQKPGQAPRLLIYDASNRATGI    Germline VKIII-L6
EIVLTQSPATLSLSPGERATLSCRASQSVSSYLAWYQQKPGQAPRLLIYDASNRATGI    2C6 V_La
EIVLTQSPATLSLSPGERATLSCRASQSVSSYLAWYQQKPGQAPRLLIYDASNRATGI    11B8 V_L 60        70        80        90        100
PARFSGSGSGTDFTLTISSLEPEDFAVYYCQQRSNWP-------------          Germline VKIII-L6 (SEQ ID NO:75)
PARFSGSGSGTDFTLTISSLEPEDFAVYYCQQRSNWPLTFGGGTKVEIK           2C6 V_La          (SEQ ID NO:76)
PARFSGSGSGTDFTLTISSLEPEDFAVYYCQQRSDWPLTFGGGTKVEIK           11B8 V_L          (SEQ ID NO:77)

1         10        20        30        40        50
DIQMTQSPSSLSASVGDRVTITCRASQGISSWLAWYQQKPEKAPKSLIYAASSLQSGV    Germline VKI-L15
DIQMTQSPSSLSASVGDRVTITCRASQGISSWLAWYQQKPEKAPKSLIYAASSLQSGV    2C6 V_Lb 60        70        80        90        100
PSRFSGSGSGTDFTLTISSLQPEDFATYYCQQYNSYP-----------            Germline VKI-L15 (SEQ ID NO:78)
PSRFSGSGSGTDFTLTISSLQPEDFATYYCQQYNSVFTFGPGTKVDIK            2C6 V_Lb         (SEQ ID NO:79)
```

HUMAN MONOCLONAL ANTIBODIES AGAINST CD20

RELATED APPLICATIONS

This application is the U.S. National Stage of International Application No. PCT/DK2005/000270, filed Apr. 20, 2005, published in English, and claims priority under 35U.S.C. §119 or 365 to Denmark Application No. PA 2004 00627, filed Apr. 20, 2004.

BACKGROUND OF THE INVENTION

The CD20 molecule (also called human B-lymphocyte-restricted differentiation antigen or Bp35) is a hydrophobic transmembrane protein with a molecular weight of approximately 35 kD located on pre-B and mature B lymphocytes (Valentine et al. (1989) *J. Biol. Chem.* 264(19):11282-11287; and Einfield et al. (1988) *EMBO J.* 7(3):711-717). CD20 is found on the surface of greater than 90% of B cells from peripheral blood or lymphoid organs and is expressed during early pre-B cell development and remains until plasma cell differentiation. CD20 is present on both normal B cells as well as malignant B cells. In particular, CD20 is expressed on greater than 90% of B cell non-Hodgkin's lymphomas (NHL) (Anderson et al. (1984) *Blood* 63(6):1424-1433), but is not found on hematopoietic stem cells, pro-B cells, normal plasma cells, or other normal tissues (Tedder et al. (1985) *J. Immunol.* 135(2):973-979).

The 85 amino acid carboxyl-terminal region of the CD20 protein is located within the cytoplasm. The length of this region contrasts with that of other B cell-specific surface structures such as IgM, IgD, and IgG heavy chains or histocompatibility antigens class II α or β chains, which have relatively short intracytoplasmic regions of 3, 3, 28, 15, and 16 amino acids, respectively (Komaromy et al. (1983) *NAR* 11:6775-6785). Of the last 61 carboxyl-terminal amino acids, 21 are acidic residues, whereas only 2 are basic, indicating that this region has a strong net negative charge. The GenBank Accession No. is NP_690605.

It is thought that CD20 might be involved in regulating an early step(s) in the activation and differentiation process of B cells (Tedder et al. (1986) *Eur. J. Immunol.* 16:881-887) and could function as a calcium ion channel (Tedder et al. (1990) *J. Cell. Biochem.* 14D:195).

Despite uncertainty about the actual function of CD20 in promoting proliferation and/or differentiation of B cells, it provides an important target for antibody mediated therapy to control or kill B cells involved in cancers and autoimmune disorders. In particular, the expression of CD20 on tumor cells, e.g., NHL, makes it an important target for antibody mediated therapy to specifically target therapeutic agents against CD20-positive neoplastic cells. However, while the results obtained to date clearly establish CD20 as a useful target for immunotherapy, they also show that currently available murine and chimeric antibodies do not constitute ideal therapeutic agents.

Accordingly, the need exists for improved therapeutic antibodies against CD20 which are effective in preventing and/or treating a range of diseases involving cells expressing CD20.

SUMMARY OF THE INVENTION

The present invention provides a human monoclonal antibody which specifically binds to human CD20, and which comprises a heavy chain variable region and a light chain variable region, wherein the heavy chain variable region contains the $V_H$ CDR3 of SEQ ID NO:10.

In one embodiment the human monoclonal antibody comprises the $V_H$ CDR1 of SEQ ID NO:8, the $V_H$ CDR2 of SEQ ID NO:9 and the $V_H$ CDR3 of SEQ ID NO:10.

In one embodiment the invention provides a human monoclonal antibody which specifically binds to human CD20, and which comprises the $V_H$ region of SEQ ID NO:2, or a $V_H$ region which is at least 90% homologous, preferably at least 95% homologous, and more preferably at least 98% homologous, or at least 99% homologous to the amino acid sequence of SEQ ID NO:2.

In one embodiment the human monoclonal antibody as disclosed in any of the above embodiments comprises
(i) the $V_L$ CDR3 of SEQ ID NO:16,
(ii) the $V_L$ CDR1 of SEQ ID NO:14, the $V_L$ CDR2 of SEQ ID NO:15 and the $V_L$ CDR3 of SEQ ID NO:16,
(iii) the $V_L$ region of SEQ ID NO:5, or a $V_L$ region which is at least 90% homologous, preferably at least 95% homologous, and more preferably at least 98% homologous, or at least 99% homologous to the amino acid sequence of SEQ ID NO:5,
(iv) the $V_L$ CDR3 of SEQ ID NO:13,
(v) the $V_L$ CDR1 of SEQ ID NO:11, the $V_L$ CDR2 of SEQ ID NO:12 and the $V_L$ CDR3 of SEQ ID NO:13,
(vi) the $V_L$ region of SEQ ID NO:4, or a $V_L$ region which is at least 90% homologous, preferably at least 95% homologous, and more preferably at least 98% homologous, or at least 99% homologous to the amino acid sequence of SEQ ID NO:4,
(vii) the $V_L$ CDR3 of SEQ ID NO:19,
(viii) the $V_L$ CDR1 of SEQ ID NO:17, the $V_L$ CDR2 of SEQ ID NO:18 and the $V_L$ CDR3 of SEQ ID NO:19, or
(ix) the $V_L$ region of SEQ ID NO:7, or a $V_L$ region which is at least 90% homologous, preferably at least 95% homologous, and more preferably at least 98% homologous, or at least 99% homologous to the amino acid sequence of SEQ ID NO:7.

In one embodiment the human monoclonal antibody is an IgG1 or IgM antibody, e.g. an IgG1,κ or IgM,κ antibody.

In one embodiment the human monoclonal antibody is encoded by human heavy chain nucleic acids and human kappa light chain nucleic acids comprising variable heavy chain nucleotide sequence SEQ ID NO:1, and variable light chain nucleotide sequence SEQ ID NO:3 or SEQ ID NO:6, or conservative sequence modifications thereof.

In one embodiment the human monoclonal antibody is an antibody fragment, a single chain antibody, or a binding-domain immunoglobulin fusion protein comprising (i) a binding domain polypeptide in the form of a heavy chain variable region as defined in SEQ ID NO:2 or a light chain variable region as defined in SEQ ID NOs:4, 5 or 7 that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region.

In one embodiment the invention relates to a human monoclonal antibody, which specifically binds to human CD20, and which comprises a heavy chain variable region derived from human germline sequence $V_H$3-20 and a light chain variable region derived from human germline sequence VκIII-L6 or VκI-L15.

In one embodiment the human monoclonal antibody as defined in any of the embodiments above does not bind to CD20 which has been mutated at positions 163 or 166. More particularly, the human antibody does not bind to human CD20 mutants N163D or N166D.

In one embodiment the human monoclonal antibody as defined in any of the embodiments above binds to a discontinuous epitope on CD20, wherein the epitope has part of the first small extracellular loop and part of the second extracellular loop.

In one embodiment the invention relates to a hybridoma which produces a human monoclonal antibody against CD20 encoded by human heavy chain and human light chain nucleic acids comprising nucleotide sequences in their variable heavy chain region as set forth in SEQ ID NO:1, and nucleotide sequences in their variable light chain region as set forth in SEQ ID NO:3 or SEQ ID NO:6, respectively, or conservative sequence modifications thereof.

In one embodiment the invention relates to a hybridoma which produces a human monoclonal against CD20 having human heavy chain and light chain variable regions which comprise the human heavy chain variable amino acid sequence as set forth in SEQ ID NO:2, and the human light chain variable amino sequence as set forth in SEQ ID NO:4, SEQ ID NO:5, or SEQ ID NO:7, respectively, or conservative sequence modifications thereof.

In one embodiment the invention relates to a transfectoma which produces a human monoclonal antibody against CD20 encoded by human heavy chain variable nucleic acids as set forth in SEQ ID NO:1, and human light chain nucleic acids as set forth SEQ ID NO:3 or SEQ ID NO:6, or conservative sequence modifications thereof.

In one embodiment the invention relates to a transfectoma which produces a human monoclonal antibody against CD20 having human heavy chain and light chain variable regions which comprise the human heavy chain variable amino acid sequence as set forth in SEQ ID NO:2, and the human light chain variable amino sequence as set forth in SEQ ID NO:4, SEQ ID NO:5, or SEQ ID NO:7, respectively, or conservative sequence modifications thereof.

In one embodiment the invention relates to a eukaryotic or prokaryotic host cell which produces a human monoclonal antibody as disclosed in any of the above embodiments, and conservative sequence modifications thereof.

In one embodiment the invention relates to a pharmaceutical composition comprising the human monoclonal antibody of the invention and a pharmaceutically acceptable carrier.

In one embodiment the pharmaceutical composition may comprise one or more further therapeutic agents.

In one embodiment the antibody of the invention can further comprising a chelator linker for attaching a radioisotope.

In one embodiment the invention relates to an immunoconjugate comprising the human monoclonal antibody of the invention linked to a cytotoxic agent, a radioisotope, or a drug.

In one embodiment the immunoconjugate comprises a monomeric IgM antibody according to the invention linked to a cytotoxic agent, a radioisotope, or a drug.

In one embodiment the invention relates to a bispecific molecule comprising an antibody of the invention and a binding specificity for a human effector cell, e.g. a binding specificity for a human Fc receptor or a binding specificity for a T cell receptor, such as CD3.

In one embodiment the invention relates to a method of treating or preventing a disease or disorder involving cells expressing CD20, comprising administering to a subject a human monoclonal antibody, a pharmaceutical composition, immunoconjugate, or bispecific molecule, or an expression vector of the invention in an amount effective to treat or prevent the disease or disorder. Such methods, which also include administering one or more further therapeutic agents to the subject, are disclosed in further details in the following sections.

In one embodiment the invention relates to an in vitro method for detecting the presence of CD20 antigen, or a cell expressing CD20, in a sample comprising:

contacting the sample with the antibody of the invention under conditions that allow for formation of a complex between the antibody and CD20; and detecting the formation of a complex.

In one embodiment the invention relates to a kit for detecting the presence of CD20 antigen, or a cell expressing CD20, in a sample comprising the antibody of the invention.

In one embodiment the invention relates to an in vivo method for detecting CD20 antigen, or a cell expressing CD20, in an subject comprising:

administering the antibody of the invention under conditions that allow for formation of a complex between the antibody and CD20; and detecting the formed complex.

In one embodiment the invention relates to an expression vector comprising a heavy chain nucleotide sequence of SEQ ID NO:1, the variable region of a light chain nucleotide sequence of SEQ ID NO:3 or SEQ ID NO:6, or both the variable region of the heavy chain nucleotide sequence of SEQ ID NO:1 and the variable region of the light chain nucleotide sequence of SEQ ID NO:3 or SEQ ID NO:6, or conservative modifications thereof.

In one embodiment the expression vector further comprises a nucleotide sequence encoding the constant region of a light chain, heavy chain or both light and heavy chains of a human antibody, which binds to human CD20.

In one embodiment the invention relates to an expression vector comprising a nucleotide sequence encoding a heavy chain variable region comprising an amino acid sequence as set forth in SEQ ID NO:2, and a nucleotide sequence encoding a light chain variable region comprising an amino acid sequence as set forth in SEQ ID NO:4, SEQ ID NO:5 or SEQ ID NO:7, or conservative modifications thereof.

In one embodiment the invention relates to a pharmaceutical composition comprising the expression vector as disclosed in any of the above embodiments and a pharmaceutically acceptable carrier.

In one embodiment the invention relates to an anti-idiotypic antibody binding to an antibody of the invention, e.g. 2C6 IgG1,κ, and use of such anti-idiotypic antibodies for detecting the level of human monoclonal antibody against CD20 in a sample.

Anti-idiotypic antibodies can be produced by immunizing Balb/C mice with an antibody of the invention, e.g. 2C6 IgG1,κ and generating hybridomas from spleens of these mice by fusion with NS1 myeloma cells using standard techniques. The anti-idiotype antibodies can be tested for specific binding to the relevant antibody by coating ELISA plates with purified antibody (diluted in PBS to a final concentration of 1-2 μg/ml, 37° C., 2 hours).

The specific anti-idiotypic antibodies can be used as an immunodiagnostic tool to detect and quantify levels of human monoclonal antibodies against CD20 in laboratory or patient samples. This may be useful for examining pharmakokinetics of the anti-CD20 antibody or for determining and adjusting the dosage of the anti-CD20 antibody and for monitoring the disease and the effect of treatment in a patient. As an example of such an assay, ELISA plates are coated with 4 μg/ml anti-idiotypic antibody. Plates are blocked with PBS containing 0.05% Tween-20 and 2% chicken serum (room temperature, 1 hour). Subsequently, the plates are incubated with a serial dilution of the relevant antibody, e.g. 2C6 IgG1,κ (10,000-9.77 ng/ml, room temperature, 2 hours). Bound 2C6 IgG1,κ is detected with mouse-anti-human IgG HRP-conjugated antibody.

Other features and advantages of the instant invention will be apparent from the following detailed description and claims.

BRIEF DESCRIPTION OF THE DRAWINGS

FIG. 14 shows the $V_H$ 2C6, $V_L$a 2C6, $V_L$b 2C6, and $V_L$ 11B8 amino acid sequences aligned with their germline sequences.

BRIEF DESCRIPTION OF SEQUENCE LISTING

Figure 1A:
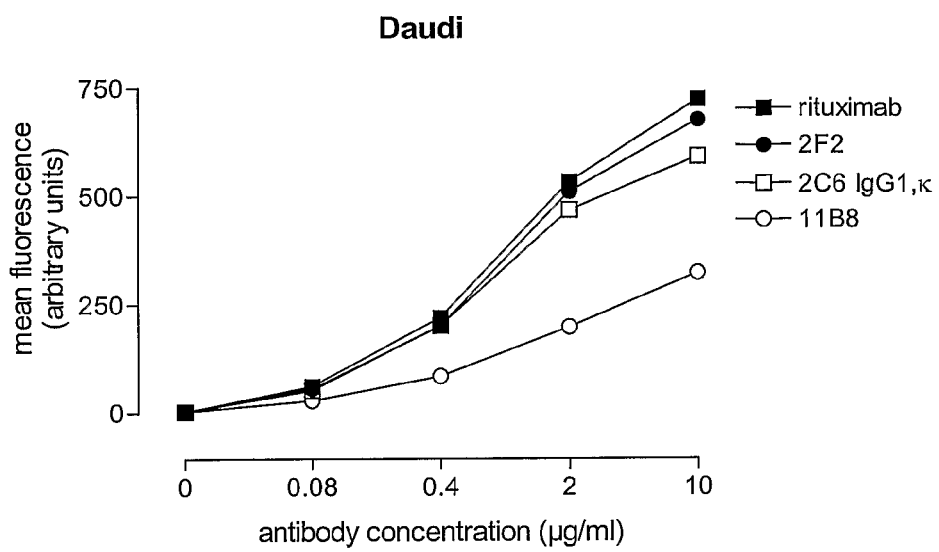
FIGS. 1A and 1B show the binding of 2C6 IgG1,κ, and in comparison herewith rituximab (chimeric anti-CD20 antibody, IDEC), 2F2 (human recombinant monoclonal IgG1,κ anti-CD20 antibody as further disclosed herein and in WO 2004/035607) and 11B8 (human recombinant monoclonal IgG1,κ anti-CD20 antibody as further disclosed herein and in WO 2004/035607), to Daudi cells (FIG. 1A) or Raji cells (FIG. 1B) using flow cytometry.
Figure 1B:
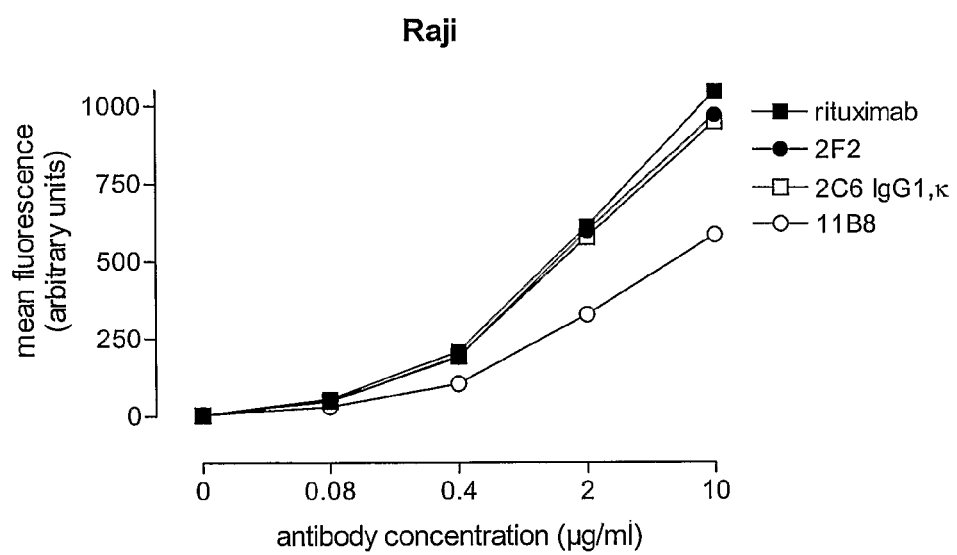

SEQ ID NO:1 is the $V_H$ 2C6 nucleotide sequence. SEQ ID NO:2 is the $V_H$ 2C6 amino acid sequence.
SEQ ID NO:3 is the $V_L$a 2C6 nucleotide sequence.
SEQ ID NO:4 is the $V_L$a 2C6 amino acid sequence.
SEQ ID NO:5 is the $V_L$b 2C6 amino acid sequence.
SEQ ID NO:6 is the $V_L$ 11B8 nucleotide sequence.
SEQ ID NO:7 is the $V_L$ 11B8 amino acid sequence.
SEQ ID NO:8 is the $V_H$ 2C6 CDR1 amino acid sequence.
SEQ ID NO:9 is the $V_H$ 2C6 CDR2 amino acid sequence.
SEQ ID NO:10 is the $V_H$ 2C6 CDR3 amino acid sequence.
SEQ ID NO:11 is the $V_L$a 2C6 CDR1 amino acid sequence.
SEQ ID NO:12 is the $V_L$a 2C6 CDR2 amino acid sequence.
SEQ ID NO:13 is the $V_L$a 2C6 CDR3 amino acid sequence.
SEQ ID NO:14 is the $V_L$b 2C6 CDR1 amino acid sequence.
SEQ ID NO:15 is the $V_L$b 2C6 CDR2 amino acid sequence.
SEQ ID NO:16 is the $V_L$b 2C6 CDR3 amino acid sequence.
SEQ ID NO:17 is the $V_L$ 11B8 CDR1 amino acid sequence.
SEQ ID NO:18 is the $V_L$ 11B8 CDR2 amino acid sequence.
SEQ ID NO:19 is the $V_L$ 11B8 CDR3 amino acid sequence.
SEQ ID NOs:20-27 are the primers used in Example 3.

DETAILED DESCRIPTION OF THE INVENTION

In order that the present invention may be more readily understood, certain terms are first defined. Additional definitions are set forth throughout the detailed description.

The terms "CD20" and "CD20 antigen" are used interchangeably herein, and include any variants, isoforms and species homologs of human CD20 which are naturally expressed by cells or are expressed on cells transfected with the CD20 gene. Binding of an antibody of the invention to the CD20 antigen mediate the killing of cells expressing CD20 (e.g., a tumor cell) by inactivating CD20. The killing of the cells expressing CD20 may occur by one or more of the following mechanisms:

complement dependent cytotoxicity (CDC) of cells expressing CD20;

effector cell phagocytosis of cells expressing CD20; or effector cell antibody dependent cellular cytotoxicity (ADCC) of cells expressing CD20.

Synonyms of CD20, as recognized in the art, include B-lymphocyte antigen CD20, B-lymphocyte surface antigen B1, Leu-16, Bp35, BM5, and LF5.

As used herein, the term "inhibits growth" (e.g., referring to cells) is intended to include any measurable decrease in the cell growth when contacted with an anti-CD20 antibody as compared to the growth of the same cells not in contact with an anti-CD20 antibody, e.g., the inhibition of growth of a cell culture by at least about 10%, 20%, 30%, 40%, 50%, 60%, 70%, 80%, 90%, 99%, or 100%. Such a decrease in cell growth can occur by a variety of mechanisms, e.g., effector cell phagocytosis, ADCC, CDC, and/or apoptosis.

The term "antibody" as referred to herein includes whole antibodies and any antigen binding fragment (i.e., "antigen-binding portion") or single chain thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region (abbreviated herein as $C_H$). Each light chain is comprised of a light chain variable region (abbreviated herein as $V_L$) and a light chain constant region (abbreviated herein as $C_L$). The $V_H$ and $V_L$ regions can be further subdivided into regions of hypervariability, termed complementarity determining regions (CDRs), interspersed with regions that are more conserved, termed framework regions (FRs). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding portion" of an antibody (or simply "antibody portion"), as used herein, refers to one or more fragments of an antibody that retain the ability to specifically bind to an antigen (e.g., CD20). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_H$ domains; (ii) a F(ab')$_2$ fragment, a bivalent fragment comprising two Fab fragments linked by a disulfide bridge at the hinge region; (iii) a Fd fragment consisting of the $V_H$ and $C_H$ domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; (vi) an isolated complementarity determining region (CDR), and (vii) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. A further example is binding-domain immunoglobulin fusion proteins comprising (i) a binding domain polypeptide that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. The binding domain polypeptide can be a heavy chain variable region or a light chain variable region. Such binding-domain immunoglobulin fusion proteins are further disclosed in US 2003/0118592 and US 2003/0133939. These antibody fragments are obtained using conventional techniques known to those with skill in the art, and the fragments are screened for utility in the same manner as are intact antibodies.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

The term "discontinuous epitope", as used herein, means a conformational epitope on a protein antigen which is formed from at least two separate regions in the primary sequence of the protein.

The term "bispecific molecule" is intended to include any agent, e.g., a protein, peptide, or protein or peptide complex, which has two different binding specificities. For example, the molecule may bind to, or interact with, (a) a cell surface antigen and (b) an Fc receptor on the surface of an effector cell. The term "multispecific molecule" or "heterospecific molecule" is intended to include any agent, e.g., a protein, peptide, or protein or peptide complex, which has more than two different binding specificities. For example, the molecule may bind to, or interact with, (a) a cell surface antigen, (b) an Fc receptor on the surface of an effector cell, and (c) at least one other component. Accordingly, the invention includes, but is not limited to, bispecific, trispecific, tetraspecific, and other multispecific molecules which are directed to CD20, and to other cell surface antigens or targets, such as Fc receptors on effector cells.

The term "bispecific antibodies" also includes diabodies. Diabodies are bivalent, bispecific antibodies in which the $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Nat. Acad. Sci. USA 90:6444-6448; Poljak, R. J., et al. (1994) Structure 2:1121-1123).

The term "human antibody derivatives" refers to any modified form of the antibody, e.g., a conjugate of the antibody and another agent or antibody.

As used herein, a human antibody is "derived from" a particular germine sequence if the antibody is obtained from a system using human immunoglobulin sequences, e.g., by immunizing a transgenic mouse carrying human immunoglobulin genes or by screening a human immunoglobulin gene library, and wherein the selected human antibody is at least 90%, more preferably at least 95%, even more preferably at least 96%, 97%, 98%, or 99% identical in amino acid sequence to the amino acid sequence encoded by the germine immunoglobulin gene. Typically, a human antibody derived from a particular human germline sequence will display no more than 10 amino acid differences, more preferably, no more than 5, or even more preferably, no more than 4, 3, 2, or 1 amino acid difference from the amino acid sequence encoded by the germine immunoglobulin gene.

The term "human antibody", as used herein, is intended to include antibodies having variable and constant regions derived from human germline immunoglobulin sequences. The human antibodies of the invention may include amino acid residues not encoded by human germine immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The terms "monoclonal antibody" or "monoclonal antibody composition" as used herein refer to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences.

The term "recombinant human antibody", as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further in Section I, below), (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable and constant regions derived from human germine immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

The term "transfectoma", as used herein, includes recombinant eukaryotic host cells expressing the antibody, such as CHO cells, NS/0 cells, HEK293 cells, plant cells, or fungi, including yeast cells.

As used herein, a "heterologous antibody" is defined in relation to the transgenic non-human organism producing such an antibody. This term refers to an antibody having an amino acid sequence or an encoding nucleic acid sequence corresponding to that found in an organism not consisting of the transgenic non-human animal, and generally from a species other than that of the transgenic non-human animal.

An "isolated antibody", as used herein, is intended to refer to an antibody which is substantially free of other antibodies having different antigenic specificities (e.g., an isolated antibody that specifically binds to CD20 is substantially free of antibodies that specifically bind antigens other than CD20). An isolated antibody that specifically binds to an epitope, isoform or variant of human CD20 may, however, have cross-reactivity to other related antigens, e.g., from other species (e.g., CD20 species homologs). Moreover, an isolated antibody may be substantially free of other cellular material and/or chemicals. In one embodiment of the invention, a combination of "isolated" monoclonal antibodies having different specificities are combined in a well defined composition.

As used herein, "specific binding" refers to antibody binding to a predetermined antigen. Typically, the antibody binds with an affinity corresponding to a $K_D$ of about $10^{-7}$ M or less, such as about $10^{-8}$ M or less, such as about $10^{-9}$ M or less, about $10^{-10}$ M or less, or about $10^{-11}$ M or even less, when measured as apparent affinities based on $IC_{50}$ values in FACS, and binds to the predetermined antigen with an affinity corresponding to a $K_D$ that is at least ten-fold lower, such as at least 100-fold lower than its affinity for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen".

The term "$K_D$" (M), as used herein, is intended to refer to the dissociation equilibrium constant of a particular antibody-antigen interaction.

As used herein, "isotype" refers to the antibody class (e.g., IgM or IgG1) that is encoded by heavy chain constant region genes.

As used herein, "isotype switching" refers to the phenomenon by which the class, or isotype, of an antibody changes from one immunoglobulin class to one of the other immunoglobulin classes.

As used herein, "nonswitched isotype" refers to the isotypic class of heavy chain that is produced when no isotype switching has taken place; the $C_H$ gene encoding the non-switched isotype is typically the first $C_H$ gene immediately downstream from the functionally rearranged VDJ gene. Isotype switching has been classified as classical or non-classical isotype switching. Classical isotype switching occurs by recombination events which involve at least one switch sequence region in the transgene. Non-classical isotype switching may occur by, for example, homologous recombination between human $\sigma_\mu$ and human $\Sigma_\mu$ (δ-associated deletion). Alternative non-classical switching mechanisms, such as intertransgene and/or interchromosomal recombination, among others, may occur and effectuate isotype switching.

As used herein, the term "switch sequence" refers to those DNA sequences responsible for switch recombination. A "switch donor" sequence, typically a μ switch region, will be 5' (i.e., upstream) of the construct region to be deleted during the switch recombination. The "switch acceptor" region will be between the construct region to be deleted and the replacement constant region (e.g., γ, ε, etc.). As there is no specific site where recombination always occurs, the final gene sequence will typically not be predictable from the construct.

As used herein, "glycosylation pattern" is defined as the pattern of carbohydrate units that are covalently attached to a protein, more specifically to an immunoglobulin (antibody) protein. A glycosylation pattern of a heterologous antibody can be characterized as being substantially similar to glycosylation patterns which occur naturally on antibodies produced by the species of the non-human transgenic animal, when one of ordinary skill in the art would recognize the glycosylation pattern of the heterologous antibody as being more similar to said pattern of glycosylation in the species of the non-human transgenic animal than to the species from which the CH genes of the transgene were derived.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "rearranged" as used herein refers to a configuration of a heavy chain or light chain immunoglobulin locus wherein a V segment is positioned immediately adjacent to a D-J or J segment in a conformation encoding essentially a complete $V_H$ or $V_L$ domain, respectively. A rearranged immunoglobulin (antibody) gene locus can be identified by comparison to germline DNA; a rearranged locus will have at least one recombined heptamer/nonamer homology element.

The term "unrearranged" or "germline configuration" as used herein in reference to a V segment refers to the configuration wherein the V segment is not recombined so as to be immediately adjacent to a D or J segment.

The term "nucleic acid molecule", as used herein, is intended to include DNA molecules and RNA molecules. A nucleic acid molecule may be single-stranded or double-stranded, but preferably is double-stranded DNA.

The term "isolated nucleic acid molecule", as used herein in reference to nucleic acids encoding whole antibodies or antibody portions (e.g., $V_H$, $V_L$, CDR3) that bind to CD20, is intended to refer to a nucleic acid molecule in which the nucleotide sequences encoding the intact antibody or antibody portion are free of other nucleotide sequences encoding whole antibodies or antibody portions that bind antigens other than CD20, which other sequences may naturally flank the nucleic acid in human genomic DNA.

As disclosed and claimed herein, the sequences set forth in SEQ ID NOs: 1-19 include "conservative sequence modifications", i.e., nucleotide and amino acid sequence modifications which do not significantly affect or alter the binding characteristics of the antibody encoded by the nucleotide sequence or containing the amino acid sequence. Such conservative sequence modifications include nucleotide and amino acid substitutions, additions and deletions. Modifications can be introduced into the sequences by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in a human anti-CD20 antibody is preferably replaced with another amino acid residue from the same side chain family.

The present invention also encompasses "derivatives" of the amino acid sequences as set forth in SEQ ID NOs:2, 4, 5, and 7 and conservative sequence modifications thereof, wherein one or more of the amino acid residues have been derivatised, e.g., by acylation or glycosylation, without significantly affecting or altering the binding characteristics of the antibody containing the amino acid sequences.

Furthermore, the present invention comprises antibodies in which one or more alterations have been made in the Fc region in order to change functional or pharmacokinetic properties of the antibodies. Such alterations may result in a decrease or increase of C1q binding and CDC (complement dependent cytotoxicity) or of FcγR binding and antibody-dependent cellular cytotoxicity (ADCC). Substitutions can for example be made in one or more of the amino acid positions 234, 235, 236, 237, 297, 318, 320, and 322 of the heavy chain constant region, thereby causing an alteration in an effector function while retaining binding to antigen as compared with the unmodified antibody, cf. U.S. Pat. No. 5,624, 821 and U.S. Pat. No. 5,648,260. Further reference may be had to WO 00/42072 disclosing antibodies with altered Fc regions that increase ADCC, and WO 94/29351 disclosing antibodies having mutations in the N-terminal region of the CH2 domain that alter the ability of the antibodies to bind to FcR and thereby decreases the ability of the antibodies to bind to C1q which in turn decreases the ability of the antibodies to fix complement. Furthermore, Shields et al., *J. Biol. Chem.* (2001) 276:6591-6604 teaches combination variants, e.g. T256A/S298A, S298A/E333A, and S298A/E333A/K334A, that improve FcγRIII binding.

The in vivo half-life of the antibodies can also be improved by modifying the salvage receptor epitope of the Ig constant domain or an Ig-like constant domain such that the molecule does not comprise an intact CH2 domain or an intact Ig Fc region, cf. U.S. Pat. No. 6,121,022 and U.S. Pat. No. 6,194, 551. The in vivo half-life can furthermore be increased by making mutations in the Fc region, e.g. by substituting threonine for leucine at position 252, threonine for serine at position 254, or threonine for phenylalanine at position 256, cf. U.S. Pat. No. 6,277,375.

Furthermore, the glycosylation pattern of the antibodies can be modified in order to change the effector function of the antibodies. For example, the antibodies can be expressed in a transfectoma which does not add the fucose unit normally attached to the carbohydrate attached to Asn at position 297 of Fc in order to enhance the affinity of Fc for FcγRIII which in turn will result in an increased ADCC of the antibodies in the presence of NK cells, cf. Shield et al. (2002) *J. Biol. Chem.*, 277:26733. Furthermore, modification of galactosylation can be made in order to modify CDC. Further reference may be had to WO 99/54342 and Umana et al., *Nat. Biotechnol.* (1999) 17:176 disclosing a CHO cell line engineered to express GntIII resulting in the expression of monoclonal antibodies with altered glycoforms and improved ADCC activity.

Furthermore, the antibody fragments, e.g. Fab fragments, of the invention can be pegylated to increase the half-life. This can be carried out by pegylation reactions known in the art, as described, for example, in *Focus on Growth Factors* (1992) 3:4-10, EP 154 316 and EP 401 384.

Furthermore, the antibodies can be administered in combination with beta-glucan to enhance ADCC activity, cf. Ross, G. D., et al. (1999) *Immunopharmacology* 42:61-74; Vetvicka, V., et al. JCI (1996) 98:50-61; Yan, J., et al. JI (1999) 163:3045-3052; Cheung, N-K. V., et al. *Cancer Immunol. Immunother* (2002) 51:557-564; and Hong F., et al. *Cancer Research* (2003) 63:9023-9031.

Alternatively, in another embodiment, mutations can be introduced randomly along all or part of an anti-CD20 antibody coding sequence, such as by saturation mutagenesis, and the resulting modified anti-CD20 antibodies can be screened for binding activity.

Accordingly, antibodies encoded by the (heavy and light chain variable region) nucleotide sequences disclosed herein (i.e., SEQ ID NOs:1, 3 and 6) and/or containing the (heavy and light chain variable region) amino acid sequences disclosed herein (i.e., SEQ ID NOs:2, 4, 5 and 7) include substantially similar antibodies encoded by or containing similar sequences which have been conservatively modified. Further discussion as to how such substantially similar antibodies can be generated based on the partial (i.e., heavy and light chain variable regions) sequences disclosed herein is provided below.

For nucleotide and amino acid sequences, the term "homology" indicates the degree of identity between two nucleic acid or amino acid sequences when optimally aligned and compared with appropriate insertions or deletions. Alternatively, substantial homology exists when the DNA segments will hybridize under selective hybridization conditions, to the complement of the strand.

The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package, using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (*Comput. Appl. Biosci.*, 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* 48:444-453 (1970)) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6.

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. Current Protocols in Molecular Biology, Greene Publishing and Wiley Interscience, New York (1987).

The nucleic acid compositions of the present invention, while often in a native sequence (except for modified restriction sites and the like), from either cDNA, genomic or mixtures thereof, may be mutated in accordance with standard techniques to provide gene sequences. For coding sequences, these mutations, may affect amino acid sequence as desired. In particular, DNA sequences substantially homologous to or derived from native V, D, J, constant, switches and other such sequences described herein are contemplated (where "derived" indicates that a sequence is identical or modified from another sequence).

A nucleic acid is "operably linked" when it is placed into a functional relationship with another nucleic acid sequence. For instance, a promoter or enhancer is operably linked to a coding sequence if it affects the transcription of the sequence. With respect to transcription of regulatory sequences, operably linked means that the DNA sequences being linked are contiguous and, where necessary to join two protein coding regions, contiguous and in reading frame. For switch sequences, operably linked indicates that the sequences are capable of effecting switch recombination.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. Recombinant host cells include, for example, transfectomas, such as CHO cells, NS/0 cells, and lymphocytic cells.

As used herein, the term "subject" includes any human or non-human animal. The term "non-human animal" includes all vertebrates, e.g., mammals and non-mammals, such as non-human primates, sheep, dog, cow, chickens, amphibians, reptiles, etc.

The terms "transgenic, non-human animal" refers to a non-human animal having a genome comprising one or more human heavy and/or light chain transgenes or transchromosomes (either integrated or non-integrated into the animal's natural genomic DNA) and which is capable of expressing fully human antibodies. For example, a transgenic mouse can have a human light chain transgene and either a human heavy chain transgene or human heavy chain transchromosome, such that the mouse produces human anti-CD20 antibodies when immunized with CD20 antigen and/or cells expressing CD20. The human heavy chain transgene can be integrated into the chromosomal DNA of the mouse, as is the case for transgenic, e.g., HuMAb mice, such as HCo7 or HCo12 mice, or the human heavy chain transgene can be maintained extrachromosomally, as is the case for transchromosomal KM mice as described in WO 02/43478. Such transgenic and transchromosomal mice are capable of producing multiple isotypes of human monoclonal antibodies to CD20 (e.g., IgM, IgG, IgA and/or IgE) by undergoing V-D-J recombination and isotype switching.

Various aspects of the invention are described in further detail in the following subsections.

I. Production of Human Antibodies to CD20

Human monoclonal antibodies of the invention can be produced by a variety of techniques, including conventional monoclonal antibody methodology, e.g., the standard somatic cell hybridization technique of Kohler and Milstein, *Nature* 256:495 (1975). Although somatic cell hybridization procedures are preferred, in principle, other techniques for producing monoclonal antibody can be employed, e.g., viral or oncogenic transformation of B-lymphocytes or phage display techniques using libraries of human antibody genes.

In a preferred embodiment, human monoclonal antibodies directed against CD20 can be generated using transgenic or transchromosomal mice carrying parts of the human immune system rather than the mouse system. These transgenic and transchromosomic mice include mice referred to herein as HuMAb mice and KM mice, respectively, and are collectively referred to herein as "transgenic mice."

The HuMAb mouse contains a human immunoglobulin gene miniloci that encodes unrearranged human heavy (μ and γ) and κ light chain immunoglobulin sequences, together with targeted mutations that inactivate the endogenous μ and κ chain loci (Lonberg, N. et al. (1994) *Nature* 368 (6474):856-859). Accordingly, the mice exhibit reduced expression of mouse IgM or K and in response to immunization, the introduced human heavy and light chain transgenes, undergo class switching and somatic mutation to generate high affinity human IgG,κ monoclonal antibodies (Lonberg, N. et al. (1994), supra; reviewed in Lonberg, N. (1994) *Handbook of Experimental Pharmacology* 113:49-101; Lonberg, N. and Huszar, D. (1995) *Intern. Rev. Immunol. Vol.* 13:65-93, and Harding, F. and Lonberg, N. (1995) *Ann. N.Y. Acad. Sci.* 764:536-546). The preparation of HuMAb mice is described in detail in Taylor, L. et al. (1992) *Nucleic Acids Research* 20:6287-6295; Chen, J. et al. (1993) *International Immunology* 5:647-656; Tuaillon et al. (1994) *J. Immunol.* 152:2912-2920; Lonberg et al., (1994) *Nature* 368(6474):856-859; Lonberg, N. (1994) *Handbook of Experimental Pharmacology* 113:49-101; Taylor, L. et al. (1994) *International Immunology* 6:579-591; Lonberg, N. and Huszar, D. (1995) *Intern. Rev. Immunol. Vol.* 13:65-93; Harding, F. and Lonberg, N. (1995) *Ann. N.Y. Acad. Sci.* 764:536-546; Fishwild, D. et al. (1996) *Nature Biotechnology* 14:845-851. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay, as well as U.S. Pat. No. 5,545,807 to Surani et al.; WO 98/24884, WO 94/25585, WO 93/1227, WO 92/22645, WO 92/03918 and WO 01/09187.

The KM mouse contains a human heavy chain transchromosome and a human kappa light chain transgene. The endogenous mouse heavy and light chain genes also have been disrupted in the KM mice such that immunization of the mice leads to production of human immunoglobulins rather than mouse immunoglobulins. Construction of KM mice and their use to raise human immunoglobulins is described in detail in WO 02/43478.

Immunizations

To generate fully human monoclonal antibodies to CD20, transgenic or trans-chromosomal mice containing human immunoglobulin genes (e.g., HCo12, HCo7 or KM mice) can be immunized with an enriched preparation of CD20 antigen and/or cells expressing CD20, as described, for example, by Lonberg et al. (1994), supra; Fishwild et al. (1996), supra, and WO 98/24884. Alternatively, mice can be immunized with DNA encoding human CD20. Preferably, the mice will be 6-16 weeks of age upon the first infusion. For example, an enriched preparation (5-50 μg) of the CD20 antigen can be used to immunize the HuMAb mice intraperitoneally. In the event that immunizations using a purified or enriched preparation of the CD20 antigen do not result in antibodies, mice can also be immunized with cells expressing CD20, e.g., a cell line, to promote immune responses.

Cumulative experience with various antigens has shown that the HuMAb transgenic mice respond best when initially immunized intraperitoneally (i.p.) or subcutaneously (s.c.) with CD20 expressing cells in complete Freund's adjuvant, followed by every other week i.p. immunizations (up to a total of 10) with CD20 expressing cells in PBS. The immune response can be monitored over the course of the immunization protocol with plasma samples being obtained by retroorbital bleeds. The plasma can be screened by FACS analysis, and mice with sufficient titers of anti-CD20 human immunoglobulin can be used for fusions. Mice can be boosted intravenously with CD20 expressing cells for example 4 and 3 days before sacrifice and removal of the spleen.

Generation of Hybridomas Producing Human Monoclonal Antibodies to CD20

To generate hybridomas producing human monoclonal antibodies to human CD20, splenocytes and lymph node cells from immunized mice can be isolated and fused to an appropriate immortalized cell line, such as a mouse myeloma cell line. The resulting hybridomas can then be screened for the production of antigen-specific antibodies. For example, single cell suspensions of splenic lymphocytes from immunized mice can be fused to SP2/0 nonsecreting mouse myeloma cells (ATCC, CRL 1581) with 50% PEG (w/v). Cells can be plated at approximately $1 \times 10^5$ per well in flat bottom microtiter plate, followed by a two week incubation in selective medium containing besides usual reagents 10% fetal Clone Serum, 5-10% origen hybridoma cloning factor (IGEN) and 1×HAT (Sigma). After approximately two weeks, cells can be cultured in medium in which the HAT is replaced with HT. Individual wells can then be screened by ELISA for human kappa-light chain containing antibodies and by FACS analysis using CD20 expressing cells for CD20 specificity. Once extensive hybridoma growth occurs, medium can be observed usually after 10-14 days. The antibody secreting hybridomas can be replated, screened again, and if still positive for human IgG, anti-CD20 monoclonal antibodies can be subcloned at least twice by limiting dilution. The stable subclones can then be cultured in vitro to generate antibody in tissue culture medium for characterization.

Generation of Transfectomas Producing Human Monoclonal Antibodies to CD20

Human antibodies of the invention also can be produced in a host cell transfectoma using, for example, a combination of recombinant DNA techniques and gene transfection methods as is well known in the art, see e.g. Morrison, S. (1985) *Science* 229:1202.

For example, to express the antibodies, or antibody fragments thereof, DNAs encoding partial or full-length light and heavy chains, can be obtained by standard molecular biology techniques (e.g., PCR amplification, site directed mutagenesis) and can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vectors or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_L$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel; Gene Expression Technology. Methods in Enzymology 185, Academic Press, San Diego, Calif. (1990). It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP)) and polyoma. Alternatively, nonviral regulatory sequences may be used, such as the ubiquitin promoter or β-globin promoter.

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. No. 4,399,216, U.S. Pat. No. 4,634,665 and U.S. Pat. No. 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection, lipofectin transfection and the like.

In one embodiment the antibodies are expressed in eukaryotic cells, such as mammalian host cells. Preferred mammalian host cells for expressing the recombinant antibodies of the invention include CHO cells (including dhfr-CHO cells, described in Urlaub and Chasin, (1980) Proc. Natl. Acad. Sci. USA 77:4216-4220, used with a DHFR selectable marker, e.g., as described in R. J. Kaufman and P. A. Sharp (1982) Mol. Biol. 159:601-621), NS/0 myeloma cells, COS cells, HEK293 cells and SP2.0 cells. In particular for use with NS/0 myeloma cells, another preferred expression system is the GS (glutamine synthetase) gene expression system disclosed in WO 87/04462, WO 89/01036 and EP 338 841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Further Recombinant Means for Producing Human Monoclonal Antibodies to CD20

Alternatively the cloned antibody genes can be expressed in other expression systems, including prokaryotic cells, such as microorganisms, e.g. E. coli for the production of scFv antibodies, algi, as well as insect cells. Furthermore, the antibodies can be produced in transgenic non-human animals, such as in milk from sheep and rabbits or eggs from hens, or in transgenic plants. See e.g. Verma, R., et al. (1998) "Antibody engineering: Comparison of bacterial, yeast, insect and mammalian expression systems", J. Immunol. Meth. 216: 165-181; Pollock, et al. (1999) "Transgenic milk as a method for the production of recombinant antibodies", J. Immunol. Meth. 231:147-157; and Fischer, R., et al. (1999) "Molecular farming of recombinant anti-bodies in plants", Biol. Chem. 380:825-839.

Use of Partial Antibody Sequences to Express Intact Antibodies

Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) Nature 332:323-327; Jones, P. et al. (1986) Nature 321:522-525; and Queen, C. et al. (1989) Proc. Natl. Acad. Sci. USA 86:10029-10033). Such framework sequences can be obtained from public DNA databases that include germine antibody gene sequences. These germine sequences will differ from mature antibody gene sequences because they will not include completely assembled variable genes, which are formed by V(D)J joining during B cell maturation. Germline gene sequences will also differ from the sequences of a high affinity secondary repertoire antibody which contains mutations throughout the variable gene but typically clustered in the CDRs. For example, somatic mutations are relatively infrequent in the amino terminal portion of framework region 1 and in the carboxy-terminal portion of framework region 4. For this reason, it is not necessary to obtain the entire DNA sequence of a particular antibody in order to recreate an intact recombinant antibody having binding properties similar to those of the original antibody (see WO 99/45962). Partial heavy and light chain sequence spanning the CDR regions is typically sufficient for this purpose. The partial sequence is used to determine which germline variable and joining gene segments contributed to the recombined antibody variable genes. The germline sequence is then used to fill in missing portions of the variable regions. Heavy and light chain leader sequences are cleaved during protein maturation and do not contribute to the properties of the final antibody. To add missing sequences, cloned cDNA sequences can be combined with synthetic oligonucleotides by ligation or PCR amplification. Alternatively, the entire variable region can be synthesized as a set of short, overlapping, oligonucleotides and combined by PCR amplification to create an entirely synthetic variable region clone.

This process has certain advantages such as elimination or inclusion or particular restriction sites, or optimization of particular codons.

The nucleotide sequences of heavy and light chain transcripts from hybridomas are used to design an overlapping set of synthetic oligonucleotides to create synthetic V sequences with identical amino acid coding capacities as the natural sequences. The synthetic heavy and kappa chain sequences can differ from the natural sequences in three ways: strings of repeated nucleotide bases are interrupted to facilitate oligonucleotide synthesis and PCR amplification; optimal translation initiation sites are incorporated according to Kozak's rules (Kozak, 1991, J. Biol. Chem. 266:19867-19870); and HindIII sites are engineered upstream of the translation initiation sites.

For both the heavy and light chain variable regions, the optimized coding and corresponding non-coding, strand sequences are broken down into 30-50 nucleotides approximately at the midpoint of the corresponding non-coding oligonucleotide. Thus, for each chain, the oligonucleotides can be assembled into overlapping double stranded sets that span segments of 150-400 nucleotides. The pools are then used as templates to produce PCR amplification products of 150-400 nucleotides. Typically, a single variable region oligonucleotide set will be broken down into two pools which are separately amplified to generate two overlapping PCR products. These overlapping products are then combined by PCR amplification to form the complete variable region. It may also be desirable to include an overlapping fragment of the heavy or light chain constant region (including the BbsI site of the kappa light chain, or the AgeI site of the gamma heavy chain) in the PCR amplification to generate fragments that can easily be cloned into the expression vector constructs.

The reconstructed heavy and light chain variable regions are then combined with cloned promoter, leader, translation initiation, constant region, 3' untranslated, polyadenylation, and transcription termination, sequences to form expression vector constructs. The heavy and light chain expression constructs can be combined into a single vector, co-transfected, serially transfected, or separately transfected into host cells which are then fused to form a host cell expressing both chains.

In another aspect of the invention, the structural features of the human anti-CD20 antibodies of the invention are used to create structurally related human anti-CD20 antibodies that retain at least one functional property of the antibodies of the invention, such as binding to CD20. More specifically, one or more CDR regions of 2C6 can be combined recombinantly with known human framework regions and CDRs to create additional, recombinantly-engineered, human anti-CD20 antibodies of the invention.

Accordingly, in another embodiment, the invention provides a method for preparing an anti-CD20 antibody comprising:

preparing an antibody comprising (1) human heavy chain framework regions and human heavy chain CDRs, wherein at least one of the human heavy chain CDRs comprises an amino acid sequence selected from the amino acid sequences of CDRs shown in SEQ ID NOs:8-10); and (2) human light chain framework regions and human light chain CDRs, wherein at least one of the human light chain CDRs comprises an amino acid sequence selected from the amino acid sequences of CDRs shown in SEQ ID NOs:11-3, 14-16 or 17-19); wherein the antibody retains the ability to bind to CD20.

Since it is well known in the art that antibody heavy and light chain CDR3 domains play a particularly important role in the binding specificity/affinity of an antibody for an antigen, the recombinant antibodies of the invention prepared as set forth above preferably comprise the $V_H$ CDR3 of SEQ ID NO:10.

II. Bispecific/Multispecific Molecules Which Bind to CD20

In yet another embodiment of the invention, human monoclonal antibodies to CD20 can be derivatized or linked to another functional molecule, e.g., another peptide or protein (e.g., a Fab' fragment) to generate a bispecific or multispecific molecule which binds to multiple binding sites or target epitopes. For example, an antibody of the invention can be functionally linked (e.g., by chemical coupling, genetic fusion, noncovalent association or otherwise) to one or more other binding molecules, such as another antibody, peptide or binding mimetic.

Accordingly, the present invention includes bispecific and multispecific molecules comprising at least one first binding specificity for CD20 and a second binding specificity for a second target epitope. In a particular embodiment of the invention, the second target epitope is an Fc receptor, e.g., human FcγRI (CD64) or a human Fcα receptor (CD89), or a T cell receptor, e.g., CD3. Therefore, the invention includes bispecific and multispecific molecules capable of binding both to FcγR, FcαR or FcεR expressing effector cells (e.g., monocytes, macrophages or polymorphonuclear cells (PMNs)), and to target cells expressing CD20. These bispecific and multispecific molecules target CD20 expressing cells to effector cell and, like the human monoclonal antibodies of the invention, trigger Fc receptor-mediated effector cell activities, such as phagocytosis of CD20 expressing cells, antibody dependent cellular cytotoxicity (ADCC), cytokine release, or generation of superoxide anion.

Bispecific and multispecific molecules of the invention can further include a third binding specificity, in addition to an anti-Fc binding specificity and an anti-CD20 binding specificity. In one embodiment, the third binding specificity is an anti-enhancement factor (EF) portion, e.g., a molecule which binds to a surface protein involved in cytotoxic activity and thereby increases the immune response against the target cell. The "anti-enhancement factor portion" can be an antibody, functional antibody fragment or a ligand that binds to a given molecule, e.g., an antigen or a receptor, and thereby results in an enhancement of the effect of the binding determinants for the Fc receptor or target cell antigen. The "anti-enhancement factor portion" can bind an Fc receptor or a target cell antigen. Alternatively, the anti-enhancement factor portion can bind to an entity that is different from the entity to which the first and second binding specificities bind. For example, the anti-enhancement factor portion can bind a cytotoxic T cell (e.g., via CD2, CD3, CD8, CD28, CD4, CD40, ICAM-1 or other immune cell that results in an increased immune response against the target cell).

In one embodiment, the bispecific and multispecific molecules of the invention comprise as a binding specificity at least one further antibody, including, e.g., an Fab, Fab', F(ab')$_2$, Fv, or a single chain Fv. The antibody may also be a light chain or heavy chain dimer, or any minimal fragment thereof such as a Fv or a single chain construct as described in Ladner et al. in U.S. Pat. No. 4,946,778. The antibody may also be a binding-domain immunoglobulin fusion protein as disclosed in US 2003/0118592 and US 2003/0133939.

In one embodiment, the binding specificity for an Fc receptor is provided by a human monoclonal antibody, the binding of which is not blocked by human immunoglobulin G (IgG). As used herein, the term "IgG receptor" refers to any of the eight γ-chain genes located on chromosome 1. These genes encode a total of twelve transmembrane or soluble receptor isoforms which are grouped into three Fcγ receptor classes: FcγRI (CD64), FcγRII (CD32), and FcγRIII (CD16). In one preferred embodiment, the Fcγ receptor is a human high affinity FcγRI.

The production and characterization of these preferred monoclonal antibodies are described by Fanger et al. in WO 88/00052 and in U.S. Pat. No. 4,954,617. These antibodies bind to an epitope of FcγRI, FcγRII or FcγRIII at a site which is distinct from the Fcγ binding site of the receptor and, thus, their binding is not blocked substantially by physiological levels of IgG. Specific anti-FcγRI antibodies useful in this invention are mAb 22, mAb 32, mAb 44, mAb 62 and mAb 197. In other embodiments, the anti-Fcγ receptor antibody is a humanized form of mAb 22 (H22). The production and characterization of the H22 antibody is described in Graziano, R. F. et al. (1995) *J. Immunol.* 155 (10):4996-5002 and WO 94/10332. The H22 antibody producing cell line was deposited at the American Type Culture Collection on Nov. 4, 1992 under the designation HA022CL1 and has the accession No. CRL 11177.

In still other preferred embodiments, the binding specificity for an Fc receptor is provided by an antibody that binds to a human IgA receptor, e.g., an Fcα receptor (FcαI (CD89)), the binding of which is preferably not blocked by human immunoglobulin A (IgA). The term "IgA receptor" is intended to include the gene product of one α-gene (FcαRI) located on chromosome 19. This gene is known to encode several alternatively spliced transmembrane isoforms of 55 to 110 kDa. FcαRI (CD89) is constitutively expressed on monocytes/macrophages, eosinophilic and neutrophilic granulocytes, but not on non-effector cell populations. FcαRI has medium affinity for both IgA1 and IgA2, which is increased upon exposure to cytokines such as G-CSF or GM-CSF (Morton, H. C. et al. (1996) *Critical Reviews in Immunology* 16:423-440). Four FcαRI-specific monoclonal antibodies, identified as A3, A59, A62 and A77, which bind FcαRI outside the IgA ligand binding domain, have been described (Monteiro, R. C. et al. (1992) *J. Immunol.* 148:1764).

FcαRI, FcγRI, FcγRII and FcγRIII, especially FcγRII and FcγRIII, are preferred trigger receptors for use in the invention because they (1) are expressed primarily on immune effector cells, e.g., monocytes, PMNs, macrophages and dendritic cells; (2) are expressed at high levels (e.g., 5,000-100,000 per cell); (3) are mediators of cytotoxic activities (e.g., ADCC, phagocytosis); and (4) mediate enhanced antigen presentation of antigens, including self-antigens, targeted to them.

An "effector cell specific antibody" as used herein refers to an antibody or functional antibody fragment that binds the Fc receptor of effector cells. Preferred anti-bodies for use in the subject invention bind the Fc receptor of effector cells at a site which is not bound by endogenous immunoglobulin.

As used herein, the term "effector cell" refers to an immune cell which is involved in the effector phase of an immune response, as opposed to the cognitive and activation phases of an immune response. Exemplary immune cells include a cell of a myeloid or lymphoid origin, e.g., lymphocytes (e.g., B cells and T cells including cytolytic T cells (CTLs)), killer cells, natural killer cells, macrophages, monocytes, eosinophils, neutronphils, polymorphonuclear cells, granulocytes, mast cells, and basophils. Some effector cells express specific Fc receptors and carry out specific immune functions. In preferred embodiments, an effector cell is capable of inducing antibody-dependent cellular cytotoxicity (ADCC), e.g., a neutrophil capable of inducing ADCC. For example, monocytes, macrophages, which express FcR are involved in specific killing of target cells and presenting antigens to other components of the immune system, or binding to cells that present antigens. In other embodiments, an effector cell can phagocytose a target antigen, target cell, or microorganism. The expression of a particular FcR on an effector cell can be regulated by humoral factors such as cytokines. For example, expression of FcγRI has been found to be up-regulated by interferon gamma (IFN-γ) and/or G-CSF. This enhanced expression increases the cytotoxic activity of FcγRI-bearing cells against targets. An effector cell can phagocytose or lyse a target antigen or a target cell.

"Target cell" shall mean any undesirable cell in a subject (e.g., a human or animal) that can be targeted by a composition (e.g., a human monoclonal antibody, a bispecific or a multispecific molecule) of the invention. In preferred embodiments, the target cell is a cell expressing or overexpressing CD20. Cells expressing CD20 typically include B cells and B cell tumors.

While human monoclonal antibodies are preferred, other antibodies which can be employed in the bispecific or multispecific molecules of the invention are murine, chimeric and humanized monoclonal antibodies. Such murine, chimeric and humanized monoclonal antibodies can be prepared by methods known in the art.

Bispecific and multispecific molecules of the present invention can be made using chemical techniques (see e.g., D. M. Kranz et al. (1981) *Proc. Natl. Acad. Sci. USA* 78:5807), "polydoma" techniques (see U.S. Pat. No. 4,474,893), or recombinant DNA techniques.

In particular, bispecific and multispecific molecules of the present invention can be prepared by conjugating the constituent binding specificities, e.g., the anti-FcR and anti-CD20 binding specificities, using methods known in the art. For example, each binding specificity of the bispecific and multispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-5-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl)cyclohexane-1-carboxylate (sulfo-SMCC) see e.g., Karpovsky et al. (1984) *J. Exp. Med.* 160:1686; Liu, M. A., et al. (1985) *Proc. Natl. Acad. Sci. USA* 82:8648. Other methods include those described by Paulus (Behring Ins. Mitt. (1985) *No.* 78, 118-132); Brennan et al. (1985) *Science* 229:81-83, and Glennie et al. (1987) *J. Immunol.* 139:2367-2375. Preferred conjugating agents are SATA and sulfo-SMCC, both available from Pierce Chemical Co. (Rockford, Ill.).

When the binding specificities are antibodies, they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific and multispecific molecule is a mAb×mAb, mAb×Fab, Fab×F(ab')₂ or ligand×Fab fusion protein. A bispecific and multispecific molecule of the invention, e.g., a bispecific molecule can be a single chain molecule, such as a single chain bispecific antibody, a single chain bispecific molecule comprising one single chain antibody and a binding determinant, or a single chain bispecific molecule comprising two binding determinants. Bispecific and multispecific molecules can also be single chain molecules or may comprise at least two single chain molecules. Methods for preparing bi- and multispecific molecules are described for example in U.S. Pat. No. 5,260,203; U.S. Pat. No. 5,455,030; U.S. Pat. No. 4,881,175; U.S. Pat. No. 5,132,405; U.S. Pat. No. 5,091,513; U.S. Pat. No. 5,476,786; U.S. Pat. No. 5,013,653; U.S. Pat. No. 5,258,498; and U.S. Pat. No. 5,482,858.

Binding of the bispecific and multispecific molecules to their specific targets can be confirmed by enzyme-linked immunosorbent assay (ELISA), a radioimmunoassay (RIA), FACS analysis, a bioassay (e.g., growth inhibition), or a Western Blot Assay. Each of these assays generally detects the presence of protein-antibody complexes of particular interest by employing a labeled reagent (e.g., an antibody) specific for the complex of interest. For example, the FcR-antibody complexes can be detected using e.g., an enzyme-linked antibody or antibody fragment which recognizes and specifically binds to the antibody-FcR complexes. Alternatively, the complexes can be detected using any of a variety of other immunoassays. For example, the antibody can be radioactively labeled and used in a radioimmunoassay (RIA) (see, for example, Weintraub, B., Principles of Radioimmunoassays, Seventh Training Course on Radioligand Assay Techniques, The Endocrine Society, March, 1986). The radioactive isotope can be detected by such means as the use of a γ counter or a scintillation counter or by autoradiography.

III. Immunoconjugates

In another aspect, the present invention features a human anti-CD20 monoclonal antibody conjugated to a therapeutic moiety, such as a cytotoxin, a chemotherapeutic drug, an immunosuppressant or a radioisotope. Such conjugates are referred to herein as "immunoconjugates". A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Suitable chemotherapeutic agents for forming immunoconjugates of the invention include, but are not limited to, antimetabolites (e.g., methotrexate, 6-mercaptopurine, 6-thioguanine, cytarabine, fludarabin, 5-fluorouracil, decarbazine, hydroxyurea, azathiprin, gemcitabin and cladribin), alkylating agents (e.g., mechlorethamine, thioepa, chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, docetaxel, paclitaxel and vinorelbin).

Suitable radioisotopes are e.g. iodine-131, yttrium-90 or indium-111.

Further examples of therapeutic moieties may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-γ; or biological response modifiers such as, for example, lymphokines, interleukin-1 (IL-1), interleukin-2 (IL-2), interleukin-6 (IL-6), granulocyte macrophage colony stimulating factor (GM-CSF), granulocyte colony stimulating factor (G-CSF), or other growth factors.

In a preferred embodiment, the therapeutic moiety is doxorubicin, cisplatin, bleomycin, carmustine, chlorambucil, cyclophosphamide or ricin A.

Techniques for conjugating such therapeutic moiety to antibodies are well known, see, e.g., Amon et al., "Monoclonal Antibodies For Immunotargeting Of Drugs In Cancer Therapy", *Monoclonal Antibodies And Cancer Therapy*, Reisfeld et al. (eds.), pp. 243-56 (Alan R. Liss, Inc. 1985); Hellstrom et al., "Antibodies For Drug Delivery", *Controlled Drug Delivery* (2nd Ed.), Robinson et al. (eds.), pp. 623-53 (Marcel Dekker, Inc. 1987); Thorpe, "Antibody Carriers Of Cytotoxic Agents In Cancer Therapy: A Review", *Monoclonal Antibodies* 1984: Biological And Clinical Applications, Pinchera et al. (eds.), pp. 475-506 (1985); "Analysis, Results, And Future Prospective Of The Therapeutic Use Of Radiolabeled Antibody In Cancer Therapy", *Monoclonal Antibodies For Cancer Detection And Therapy*, Baldwin et al. (eds.), pp. 303-16 (Academic Press 1985), and Thorpe et al., "The Preparation And Cytotoxic Properties Of Antibody-Toxin Conjugates", *Immunol. Rev.*, 62:119-58 (1982).

In a further embodiment, the human monoclonal antibodies according to the invention are attached to a linker-chelator, e.g., tiuxetan, which allows for the antibody to be conjugated to a radioisotope.

IV. Pharmaceutical Compositions

In another aspect, the present invention provides a composition, e.g., a pharmaceutical composition comprising a human monoclonal antibody of the present invention. The pharmaceutical compositions may be formulated with pharmaceutically acceptable carriers or diluents as well as any other known adjuvants and excipients in accordance with conventional techniques such as those disclosed in Remington: The Science and Practice of Pharmacy, $19^{th}$ Edition, Gennaro, Ed., Mack Publishing Co., Easton, Pa., 1995.

The pharmaceutical composition may be administered by any suitable route and mode. As will be appreciated by the skilled artisan, the route and/or mode of administration will vary depending upon the desired results.

The pharmaceutical compositions of the present invention include those suitable for oral, nasal, topical (including buccal and sublingual), rectal, vaginal and/or parenteral administration.

Formulations of the present invention which are suitable for vaginal administration include pessaries, tampons, creams, gels, pastes, foams or spray formulations containing such carriers as are known in the art to be appropriate. Dosage forms for the topical or transdermal administration of compositions of this invention include powders, sprays, ointments, pastes, creams, lotions, gels, solutions, patches and inhalants.

The pharmaceutical composition is preferably administered parenterally.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

In one embodiment the pharmaceutical composition is administered by intravenous or subcutaneous injection or infusion.

In one embodiment the human monoclonal antibodies of the invention are administered in crystalline form by subcutaneous injection, cf. Yang et al. (2003) *PNAS,* 100(12):6934-6939.

Regardless of the route of administration selected, the compounds of the present invention, which may be used in the form of a pharmaceutically acceptable salt or in a suitable hydrated form, and/or the pharmaceutical compositions of the present invention, are formulated into pharmaceutically acceptable dosage forms by conventional methods known to those of skill in the art.

As used herein, "pharmaceutically acceptable carrier" includes any and all solvents, dispersion media, coatings, antibacterial and antifungal agents, isotonicity agents, antioxidants and absorption delaying agents, and the like that are physiologically compatible.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated.

Preferably, the carrier is suitable for parenteral administration, e.g. intravenous or subcutaneous injection or infusion.

Pharmaceutical compositions typically must be sterile and stable under the conditions of manufacture and storage. The composition can be formulated as a solution, microemulsion, liposome, or other ordered structure suitable to high drug concentration. Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

The pharmaceutical compositions may also contain adjuvants such as preservatives, wetting agents, emulsifying agents and dispersing agents. Prevention of presence of microorganisms may be ensured both by sterilization procedures and by the inclusion of various antibacterial and antifungal agents, for example, paraben, chlorobutanol, phenol, sorbic acid, and the like. It may also be desirable to include isotonicity agents, such as sugars, polyalcohols such as mannitol, sorbitol, glycerol or sodium chloride in the compositions. Pharmaceutically-acceptable antioxidants may also be included, for example (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients e.g. as enumerated above, as required, followed by sterilization microfiltration. Generally, dispersions are prepared by incorporating the active compound into a sterile vehicle that contains a basic dispersion medium and the required other ingredients e.g. from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

If appropriate, the antibody may be used in a suitable hydrated form or in the form of a pharmaceutically acceptable salt. A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methyl-glucamine, chloroprocaine, choline, diethanolamine, ethylenediamine, procaine and the like.

Depending on the route of administration, the active compound, i.e., antibody, and bispecific/multispecific molecule, may be coated in a material to protect the compound from the action of acids and other natural conditions that may inactivate the compound. For example, the compound may be administered to a subject in an appropriate carrier, for example, liposomes. Liposomes include water-in-oil-in-water CGF emulsions as well as conventional liposomes (Strejan et al. (1984) J. Neuroimmunol. 7:27).

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Methods for the preparation of such formulations are generally known to those skilled in the art. See, e.g., *Sustained and Controlled Release Drug Delivery Systems,* J. R. Robinson, ed., Marcel Dekker, Inc., New York, 1978.

The pharmaceutical compositions can be administered with medical devices known in the art. For example, in a preferred embodiment, a therapeutic composition of the invention can be administered with a needleless hypodermic injection device, such as the devices disclosed in U.S. Pat. No. 5,399,163; U.S. Pat. No. 5,383,851; U.S. Pat. No. 5,312,335; U.S. Pat. No. 5,064,413; U.S. Pat. No. 4,941,880; U.S. Pat. No. 4,790,824; or U.S. Pat. No. 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known to those skilled in the art.

In certain embodiments, the human monoclonal antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. No. 4,522,811; U.S. Pat. No. 5,374,548; and U.S. Pat. No. 5,399,331. The liposomes may comprise one or more moieties which are selectively transported into specific cells or organs, thus enhance targeted drug delivery (see, e.g., V.V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J. Physiol.* 1233:134), different species of which may comprise the formulations of the inventions, as well as components of the invented molecules; p120 (Schreier et al. (1994) J. Biol. Chem. 269:9090); see also K. Keinanen; M. L. Laukkanen (1994) *FEBS Lett.* 346:123; J. J. Killion; I. J. Fidler (1994) *Immunomethods* 4:273. In one embodiment of the invention, the therapeutic compounds of the invention are formulated in liposomes; in a more preferred embodiment, the liposomes include a targeting moiety. In a most preferred embodiment, the therapeutic compounds in the liposomes are delivered by bolus injection to a site proximal to the desired area, e.g., the site of inflammation or infection, or the site of a tumor. The composition must be fluid to the extent that easy syringability exists. It must be stable under the conditions of manufacture and storage and must be preserved against the contaminating action of microorganisms such as bacteria and fungi.

In a further embodiment, the human monoclonal antibodies of the invention can be formulated to prevent or reduce their transport across the placenta. This can be done by methods known in the art, e.g., by PEGylation of the antibodies or by use of F(ab')$_2$ fragments. Further references can be made to Cunningham-Rundles C., Zhuo Z., Griffith B., Keenan J. (1992) Biological activities of polyethylene-glycol immunoglobulin conjugates. Resistance to enzymatic degradation. *J Immunol Methods.* 152:177-190; and to Landor M. (1995) Maternal-fetal transfer of immunoglobulins, *Ann. Allergy Asthma Immunol.* 74:279-283. This is particularly relevant when the antibodies are used for treating or preventing recurrent spontaneous abortion.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. In general, a suitable daily dose of a composition of the invention will be that amount of the compound which is the lowest dose effective to produce a therapeutic effect. Such an effective dose will generally depend upon the factors described above. It is preferred that administration be intravenous, intramuscular, intraperitoneal, or subcutaneous, preferably administered proximal to the site of the target. If desired, the effective daily dose of a therapeutic composition may be administered as two, three, four, five, six or more sub-doses administered separately at appropriate intervals throughout the day, optionally, in unit dosage forms. While it is possible for a compound of the present invention to be administered alone, it is preferable to administer the compound as a pharmaceutical formulation (composition).

In one embodiment, the human monoclonal antibodies according to the invention can be administered by infusion in a weekly dosage of from 10 to 500 mg/m$^2$, such as of from 200 to 400 mg/m$^2$. Such administration can be repeated, e.g., 1 to 8 times, such as 3 to 5 times. The administration may be performed by continuous infusion over a period of from 2 to 24 hours, such as of from 2 to 12 hours.

In another embodiment, the human monoclonal antibodies can be administered by slow continuous infusion over a long period, such as more than 24 hours, in order to reduce toxic side effects.

In still another embodiment the human monoclonal antibodies can be administered in a weekly dosage of from 50 mg to 4000 mg, e.g. of from 250 mg to 2000 mg, such as for example 300 mg, 500 mg, 700 mg, 1000 mg, 1500 mg or 2000 mg, for up to 8 times, such as from 4 to 6 times. The administration may be performed by continuous infusion over a period of from 2 to 24 hours, such as of from 2 to 12 hours. Such regimen may be repeated one or more times as necessary, for example, after 6 months or 12 months.

In yet another embodiment the human monoclonal antibodies can be administered in a weekly dosage of from 50 mg to 4000 mg, e.g. of from 250 mg to 2000 mg, such as for example 300 mg, 500 mg, 700 mg, 1000 mg, 1500 mg or 2000 mg, for up to 8 times, such as from 4 to 6 times. The weekly dosage may be divided into two or three subdosages and administered over more than one day. For example, a dosage of 300 mg may be administered over 2 days with 100 mg on day one (1), and 200 mg on day two (2). A dosage of 500 mg may be administered over 3 days with 100 mg on day one (1), 200 mg on day two (2), and 200 mg on day three (3), and a dosage of 700 mg may be administered over 3 days with 100 mg on day 1 (one), 300 mg on day 2 (two), and 300 mg on day 3 (three). Such mode of administration may be useful in e.g. CLL. The regimen may be repeated one or more times as necessary, for example, after 6 months or 12 months.

The dosage can be determined or adjusted by measuring the amount of circulating monoclonal anti-CD20 antibodies upon administration in a biological sample by using anti-idiotypic antibodies which target the anti-CD20 antibodies.

In yet another embodiment, the human monoclonal antibodies can be administered by maintenance therapy, such as, e.g., once a week for a period of 6 months or more.

In still another embodiment, the human monoclonal antibodies according to the invention can be administered by a regimen including one infusion of a human monoclonal antibody against CD20 followed by an infusion of a human monoclonal antibody against CD20 conjugated to a radioisotope. The regimen may be repeated, e.g., 7 to 9 days later.

A "therapeutically effective dosage" for tumor therapy can be measured by objective tumor responses which can either be complete or partial. A complete response (CR) is defined as no clinical, radiological or other evidence of disease. A partial response (PR) results from a reduction in aggregate tumor size of greater than 50%. Median time to progression is a measure that characterizes the durability of the objective tumor response.

A "therapeutically effective dosage" for tumor therapy can also be measured by its ability to stabilize the progression of disease. The ability of a compound to inhibit cancer can be evaluated in an animal model system predictive of efficacy in human tumors. Alternatively, this property of a composition can be evaluated by examining the ability of the compound to inhibit cell growth or apoptosis by in vitro assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

A "therapeutically effective dosage" for rheumatoid arthritis preferably will result in an ACR20 Preliminary Definition of Improvement in the patients, more preferred in an ACR50 Preliminary Definition of Improvement and even more preferred in an ARC70 Preliminary Definition of Improvement.

ACR20 Preliminary Definition of Improvement is defined as: $\geq$20% improvement in: Tender Joint Count (TiC) and Swollen Joint Count (SJC) and $\geq$20% improvement in 3 of following 5 assessments: Patient Pain Assessment (VAS), Patient Global assessment (VAS), Physician Global Assessment (VAS), Patent Self-Assessed Disability (HAQ), Acute Phase Reactant (CRP or ESR).

ACR50 and ACR70 are defined in the same way with $\geq$50% and $\geq$70% improvements, respectively. For further details see Felson et al. in American College of Rheumatology Preliminary Definition of Improvement in Rheumatoid Arthritis; *Arthritis Rheumatism* (1995) 38:727-735.

The pharmaceutical composition of the invention may contain one or a combination of human monoclonal antibodies of the invention. Thus, in a further embodiment, the pharmaceutical compositions include a combination of multiple (e.g., two or more) isolated human antibodies of the invention which act by different mechanisms, e.g., one antibody which predominately acts by inducing CDC in combination with another antibody which predominately acts by inducing apoptosis.

The pharmaceutical compositions of the invention also can be administered in combination therapy, i.e., combined with one or more further therapeutic agents in any suitable ratios. For example, the combination therapy can include administration of a composition of the present invention together with at least one chemotherapeutic agent, at least one anti-inflammatory agent, at least one disease modifying antirheumatic drug (DMARD), or at least one immunosuppressive agent. Such administration can be simultaneous, separate or sequential. For simultaneous administration the agents can be administered as one compositions or as separate compositions, as appropriate.

In one embodiment, such therapeutic agents include one or more chemotherapeutics selected from antimetabolites (e.g., methotrexate, 6-mercaptopurine, 6-thioguanine, cytarabine, fludarabin, 5-fluorouracil, decarbazine, hydroxyurea, azathiprin, gemcitabin and cladribin), alkylating agents (e.g., mechlorethamine, thioepa, chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vin-blastine, docetaxel, paclitaxel and vinorelbin).

In a further embodiment, the chemotherapeutic agent is selected form doxorubicin, cisplatin, bleomycin, carmustine, cyclophosphamide, and chlorambucil.

Co-administration of the human anti-CD20 antibodies of the present invention with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells which would render them unreactive with the antibody.

In another embodiment, human antibodies of the present invention may be administered in combination with chlorambucil and prednisolone; cyclophosphamide and prednisolone; cyclophosphamide, vincristine, and prednisone; cyclophosphamide, vincristine, doxorubicin, and prednisone; fludarabine and anthracycline; or in combination with other common multi-drugs regimens for NHL, such as disclosed, e.g., in Non-Hodgkin's Lymphomas: Making sense of Diagnosis, Treatment, and Options, Lorraine Johnston, 1999, O'Reilly and Associates, Inc.

In yet another embodiment, the human antibodies may be administered in conjunction with radiotherapy and/or autologous peripheral stem cell or bone marrow transplantation.

In yet a further embodiment, the human monoclonal antibodies can be administered in combination with an anti-CD25 antibody for the treatment of bullous pemphigoid, e.g., in patients with graft-versus-host disease.

In another embodiment such therapeutic agents include one or more anti-inflammatory agents, such as a steroidal drug or a NSAID (nonsteroidal anti-inflammatory drug). Preferred agents include, for example, aspirin and other salicylates, Cox-2 inhibitors, such as rofecoxib and celecoxib, NSAIDs such as ibuprofen, fenoprofen, naproxen, sulindac, diclofenac, piroxicam, ketoprofen, diflunisal, nabumetone, etodolac, oxaprozin, and indomethacin.

In another embodiment, such therapeutic agents include one or more disease modifying antirheumatic drugs (DMARDs), such as methotrexate, hydroxychloroquine, sulfasalazine, pyrimidine synthesis inhibitors, e.g., leflunomide, IL-1 receptor blocking agents, e.g., anakinra, and TNF-α blocking agents, e.g., etanercept, infliximab, and adalimumab.

In yet another embodiment, such therapeutic agents include one or more immunosuppressive agents, such as cyclosporine and azathioprine.

In another particular embodiment, the human monoclonal antibodies may be administered in combination with one or more antibodies selected from anti-CD19 anti-bodies, anti-CD21 antibodies, anti-CD22 antibodies, anti-CD37 antibodies, and anti-CD38 antibodies for the treatment of malignant diseases.

In still another particular embodiment, the human antibodies are administered in combination with one or more anti-bodies selected from anti-IL6R antibodies, anti-IL8 antibodies, anti-IL15 antibodies, anti-IL15R antibodies, anti-CD4 antibodies, anti-CD11a antibodies (e.g., efalizumab), anti-alpha-4/beta-1 integrin (VLA4) antibodies (e.g natalizumab), and CTLA4-Ig for the treatment of inflammatory diseases.

In yet a further embodiment, the human antibodies may be administered in combination with an anti-C3b(i) antibody in order to enhance complement activation.

Also within the scope of the present invention are kits comprising the antibody compositions of the invention (e.g., human antibodies and immunoconjugates) and instructions for use. The kit can further contain one or more additional agents, such as an immunosuppressive reagent, a cytotoxic agent or a radiotoxic agent, or one or more additional human antibodies of the invention (e.g., a human antibody having a complementary activity).

V. Uses and Methods of the Invention

The human antibodies (including immunoconjugates, bispecific/multispecific molecules, compositions and other derivatives described herein) of the present invention have numerous in vitro and in vivo diagnostic and therapeutic utilities involving the diagnosis and treatment of disorders involving cells expressing CD20. For example, the antibodies can be administered to cells in culture, e.g., in vitro or ex vivo, or to human subjects, e.g., in vivo, to treat, prevent and to diagnose a variety of disorders. As used herein, the term "subject" is intended to include human and non-human animals which respond to the human antibodies against CD20. Preferred subjects include human patients having disorders that can be corrected or ameliorated by inhibiting or controlling B cells (normal or malignant).

For example, the human antibodies can be used to elicit in vivo or in vitro one or more of the following biological activities: to inhibit the growth of and/or differentiation of a cell expressing CD20, to induce apoptosis of a cell expressing CD20, to kill a cell expressing CD20, to mediate phagocytosis or ADCC of a cell expressing CD20 in the presence of human effector cells, and to mediate CDC of a cell expressing CD20 in the presence of complement.

The invention provides methods for treating a disorder involving cells expressing CD20 in a subject by administering to the subject the human antibodies of the invention. Such antibodies and derivatives thereof are used to inhibit CD20 induced activities associated with certain disorders, e.g., proliferation and/or differentiation. By contacting the antibody with CD20 (e.g., by administering the antibody to a subject), the ability of CD20 to induce such activities is inhibited and, thus, the associated disorder is treated.

Accordingly, in one embodiment, the present invention provides a method for treating or preventing a tumorigenic disorder involving CD20 expressing cells.

The method involves administering to a subject an antibody composition of the present invention in an amount effective to treat or prevent the disorder. The antibody composition can be administered alone or along with another therapeutic agent, such as a cytotoxic or a radiotoxic agent which acts in conjunction with or synergistically with the antibody composition to treat or prevent the diseases involving CD20 expressing cells. Alternatively, immunoconjugates can be used to kill cells which have CD20 expressed on their surface by targeting cytotoxins or radiotoxins to CD20.

In a particular embodiment, the antibodies of the invention are used to treat or to prevent B cell lymphoma, e.g. non-Hodgkin's lymphoma (NHL), as the antibodies deplete the CD20 bearing tumor cells. CD20 is usually expressed at elevated levels on neoplastic (i.e., tumorigenic) B cells associated with NHL. Accordingly, CD20 binding antibodies of the invention can be used to deplete CD20 bearing tumor cells which lead to NHL and, thus, can be used to prevent or treat this disease.

The B cell lymphomas may be relapsed B cell lymphomas, e.g. B cell lymphomas relapsed after chemotherapy (e.g. cisplatin therapy) or after treatment with another anti-CD20 antibody (e.g. rituximab).

Non-Hodgkin's lymphoma (NHL) is a type of B cell lymphoma. Lymphomas, e.g., B cell lymphomas, are a group of related cancers that arise when a lymphocyte (a blood cell) becomes malignant. The normal function of lymphocytes is to defend the body against invaders: germs, viruses, fungi, even cancer. There are many subtypes and maturation stages of lymphocytes and, therefore, there are many kinds of lymphomas. Like normal cells, malignant lymphocytes can move to many parts of the body. Typically, lymphoma cells form tumors in the lymphatic system: bone marrow, lymph nodes, spleen, and blood. However, these cells can migrate to other organs. Certain types of lymphoma will tend to grow in locations in which the normal version of the cell resides. For example, it's common for follicular NHL tumors to develop in the lymph nodes.

Examples of non-Hodgkin's lymphoma (NHL) include precursor B cell lymphoblastic leukemia/lymphoma and mature B cell neoplasms, such as B cell chronic lymphocytic leukemia (CLL)/small lymphocytic lymphoma (SLL), B cell prolymphocytic leukemia, lymphoplasmacytic lymphoma, mantle cell lymphoma (MCL), follicular lymphoma (FL), including low-grade, intermediate-grade and high-grade FL, cutaneous follicle center lymphoma, marginal zone B cell lymphoma (MALT type, nodal and splenic type), hairy cell leukemia, diffuse large B cell lymphoma, Burkitt's lymphoma, plasmacytoma, plasma cell myeloma, post-transplant lymphoproliferative disorder, Waldenström's macroglobulinemia, anaplastic large-cell lymphoma (ALCL), lymphomatoid granulomatosis, primary effusion lymphoma, intravascular large B cell lymphoma, mediastinal large B cell lymphoma, heavy chain diseases (including γ, μ, and a disease), lymphomas induced by therapy with immunosuppressive agents, such as cyclosporine-induced lymphoma, and methotrexate-induced lymphoma.

In one embodiment the disease is follicular lymphoma (FL). In another embodiment the disease is lymphocytic leukemia (CLL)/small lymphocytic lymphoma (SLL).

In a further embodiment, the human antibodies of the present invention can be used to treat Hodgkin's lymphoma.

Human antibodies (e.g., human monoclonal antibodies, multispecific and bispecific molecules) of the present invention also can be used to block or inhibit other effects of CD20. For example, it is known that CD20 is expressed on B lymphocytes and is involved in the proliferation and/or differentiation of these cells. Since B lymphocytes function as immunomodulators, CD20 is an important target for antibody mediated therapy to target B lymphocytes, e.g., to inactivate or kill B lymphocytes, involved in immune, autoimmune, inflammatory or infectious disease or disorder involving human CD20 expressing cells.

Examples of diseases and disorders in which CD20 expressing B cells are involved and which can be treated and/or prevented include immune, autoimmune, inflammatory and infectious diseases and disorders, such as psoriasis, psoriatic arthritis, dermatitis, systemic sclerosis, inflammatory bowel disease (IBD), Crohn's disease, ulcerative colitis, respiratory distress syndrome, meningitis, encephalitis, uveitis, glomerulonephritis, eczema, asthma, atherosclerosis, leukocyte adhesion deficiency, multiple sclerosis, Raynaud's syndrome, Sjögren's syndrome, juvenile onset diabetes, Reiter's disease, Behçet's disease, immune complex nephritis, IgA nephropathy, IgM polyneuropathies, immune-mediated thrombocytopenias, such as acute idiopathic thrombocytopenic purpura and chronic idiopathic thrombocytopenic purpura, hemolytic anemia, myasthenia gravis, lupus nephritis, systemic lupus erythematosus, rheumatoid arthritis (RA), atopic dermatitis, pemphigus, Graves' disease, severe acute respiratory distress syndrome, choreoretinitis. Hashimoto's thyroiditis, Wegener's granulomatosis, Omenn's syndrome, chronic renal failure, acute infectious mononucleosis, HIV, herpes virus associated diseases, as well as diseases and disorders caused by or mediated by infection of B-cells with virus, such as Epstein-Barr virus (EBV).

Further examples of inflammatory, immune and/or autoimmune disorders in which autoantibodies and/or excessive B lymphocyte activity are prominent and which can be treated and/or prevented, include the following:

vasculitides and other vessel disorders, such as microscopic polyanguitis, Churg-Strauss syndrome, and other ANCA-associated vasculitides, polyarteritis nodosa, essential cryoglobulinaemic vasculitis, cutaneous leukocytoclastic angiitis, Kawasaki disease, Takayasu arteritis, giant cell arthritis, Henoch-Schönlein purpura, primary or isolated cerebral angiitis, erythema nodosum, thrombangiitis obliterans, thrombotic thrombocytopenic purpura (including hemolytic uremic syndrome), and secondary vasculitides, including cutaneous leukocytoclastic vasculitis (e.g., secondary to hepatitis B, hepatitis C, Waldenström's macroglobulinemia, B-cell neoplasias, rheumatoid arthritis, Sjögren's syndrome, and systemic lupus erythematosus), erythema nodosum, allergic vasculitis, panniculitis, Weber-Christian disease, purpura hyperglobulinaemica, and Buerger's disease;

skin disorders, such as contact dermatitis, linear IgA dermatosis, vitiligo, pyoderma gangrenosum, epidermolysis bullosa acquisita, pemphigus vulgaris (including cicatricial pemphigoid and bullous pemphigoid), alopecia greata (including alopecia universalis and alopecia totalis), dermatitis herpetiformis, erythema multiforme, and chronic autoimmune urticaria (including angioneurotic edema and urticarial vasculitis);

immune-mediated cytopenias, such as autoimmune neutropenia, and pure red cell aplasia;

connective tissue disorders, such as CNS lupus, discoid lupus erythematosus, CREST syndrome, mixed connective tissue disease, polymyositis/dermatomyositis, inclusion body myositis, secondary amyloidosis, cryoglobulinemia type I and type II, fibromyalgia, phospholipid antibody syndrome, secondary hemophilia, relapsing polychondritis, sarcoidosis, stiff man syndrome, rheumatic fever, and eosinophil fasciitis;

arthritides, such as ankylosing spondylitis, juvenile chronic arthritis, adult Still's disease, SAPHO syndrome, sacroileitis, reactive arthritis, Still's disease, and gout;

hematologic disorders, such as aplastic anemia, primary hemolytic anemia (including cold agglutinin syndrome), hemolytic anemia with warm autoantibodies, hemolytic anemia secondary to CLL or systemic lupus erythematosus; POEMS syndrome, pernicious anemia, Waldemström's purpura hyperglobulinaemica, Evans syndrome, agranulocytosis, autoimmune neutropenia, Franklin's disease, Seligmann's disease, µ-chain disease, factor VIII inhibitor formation, factor IX inhibitor formation, and paraneoplastic syndrome secondary to thymoma and lymphomas;

endocrinopathies, such as polyendocrinopathy, and Addison's disease; further examples are autoimmune hypoglycemia, autoimmune hypothyroidism, autoimmune insulin syndrome, de Quervain's thyroiditis, and insulin receptor antibody-mediated insulin resistance;

hepato-gastrointestinal disorders, such as celiac disease, Whipple's disease, primary biliary cirrhosis, chronic active hepatitis, primary sclerosing cholangiitis, and autoimmune gastritis;

nephropathies, such as rapid progressive glomerulonephritis, post-streptococcal nephritis, Goodpasture's syndrome, membranous glomerulonephritis, cryoglobulinemic nephritis, minimal change disease, and steroid-dependent nephritic syndrome;

neurological disorders, such as autoimmune neuropathies, mononeuritis multiplex, Lambert-Eaton's myasthenic syndrome, Sydenham's chorea, tabes dorsalis, and Guillain-Barré's syndrome; further examples are myelopathy/tropical spastic paraparesis, myasthenia gravis, acute inflammatory demyelinating polyneuropathy, and chronic inflammatory demyelinating polyneuropathy;

cardiac and pulmonary disorders, such as fibrosing alveolitis, bronchiolitis obliterans, allergic aspergillosis, cystic fibrosis, Löffler's syndrome, myocarditis, and pericarditis; further examples are hypersensitivity pneumonitis, and paraneoplastic syndrome secondary to lung cancer;

allergic disorders, such as bronchial asthma, hyper-IgE syndrome, and angioneurotic syndrome;

opthalmologic disorders, such as idiopathic chorioretinitis, and amaurosis fugax;

infectious diseases, such as parvovirus B infection (including hands-and-socks syndrome);

gynecological-obstetrical disorders, such as recurrent abortion, recurrent fetal loss, intrauterine growth retardation, and paraneoplastic syndrome secondary to gynaecological neoplasms;

male reproductive disorders, such as paraneoplastic syndrome secondary to testicular neoplasms; and transplantation-derived disorders, such as allograft and xenograft rejection, and graft-versus-host disease.

In one embodiment, the disease is rheumatoid arthritis (RA).

In another embodiment, the disease is selected from inflammatory bowel disease (IBD), ulcerative colitis, Crohn's disease, juvenile onset diabetes, multiple sclerosis, immune-mediated thrombocytopenias, such as acute idiopathic thrombocytopenic purpura and chronic idiopathic thrombocytopenic purpura, hemolytic anemia (including autoimmune hemolytic anemia), myasthenia gravis, systemic sclerosis, and pemphigus vulgaris.

In yet a further embodiment, the disease is selected from inflammatory bowel disease (IBD), ulcerative colitis, Crohn's disease, and multiple sclerosis.

Target-specific effector cells, e.g., effector cells linked to compositions (e.g., human antibodies, bispecific/multispecific) of the invention can also be used as therapeutic agents. Effector cells for targeting can be human leukocytes such as macrophages, neutrophils or monocytes. Other cells include eosinophils, natural killer cells and other IgG- or IgA-receptor bearing cells. If desired, effector cells can be obtained from the subject to be treated. The target-specific effector cells, can be administered as a suspension of cells in a physiologically acceptable solution. The number of cells administered can be in the order of 108 to 109 but will vary depending on the therapeutic purpose. In general, the amount will be sufficient to obtain localization at the target cell, e.g., a tumor cell expressing CD20, and to effect cell killing by, e.g., phagocytosis.

Therapy with target-specific effector cells can be performed in conjunction with other techniques for removal of targeted cells. For example, anti-tumor therapy using the compositions (e.g., human antibodies, bispecific/multispecific molecules) of the invention and/or effector cells armed with these compositions can be used in conjunction with chemotherapy. Additionally, combination immunotherapy may be used to direct two distinct cytotoxic effector populations toward tumor cell rejection. For example, anti-CD20 antibodies linked to anti-FcγRI or anti-CD3 may be used in conjunction with IgG- or IgA-receptor specific binding agents.

Bispecific and multispecific molecules of the invention can also be used to modulate FcγR or FcαR levels on effector cells, such as by capping and elimination of receptors on the cell surface. Mixtures of anti-Fc receptors can also be used for this purpose.

The compositions (e.g., human antibodies, multispecific and bispecific molecules and immunoconjugates) of the invention which have complement binding sites, such as portions from IgG1, -2, or -3 or IgM which bind complement, can also be used in the presence of complement. In one embodiment, ex vivo treatment of a population of cells comprising target cells with a binding agent of the invention and appropriate effector cells can be supplemented by the addition of complement or serum containing complement. Phagocytosis of target cells coated with a binding agent of the invention can be improved by binding of complement proteins. In another embodiment target cells coated with the compositions (e.g., human antibodies, multispecific and bispecific molecules) of the invention can also be lysed by complement. In yet another embodiment, the compositions of the invention do not activate complement.

The compositions (e.g., human antibodies, multispecific and bispecific molecules and immunoconjugates) of the invention can also be administered together with complement. Accordingly, within the scope of the invention are compositions comprising human antibodies, bispecific/multispecific molecules and serum or complement. These compositions are advantageous in that the complement is located in close proximity to the human antibodies, bispecific/multispecific molecules. Alternatively, the human antibodies, bispecific/multispecific molecules of the invention and the complement or serum can be administered separately. Binding of the compositions of the present invention to target cells is believed to cause translocation of the CD20 antigen-antibody complex into lipid rafts of the cell membrane. Such translocation creates a high density of antigen-antibody complexes which may efficiently activate and/or enhance CDC.

In other embodiments, the subject can be additionally treated with an agent that modulates, e.g., enhances or inhibits, the expression or activity of Fcα or Fcγ receptors by, for example, treating the subject with a cytokine. Preferred cytokines for administration during treatment with the multispecific molecule include of granulocyte colony-stimulating factor (G-CSF), granulocyte-macrophage colony-stimulating factor (GM-CSF), interferon-γ (IFN-γ), and tumor necrosis factor (TNF).

The compositions (e.g., human antibodies, multispecific and bispecific molecules) of the invention can also be used to target cells expressing FcγR or CD20, for example for labeling such cells. For such use, the binding agent can be linked to a molecule that can be detected. Thus, the invention provides methods for localizing ex vivo or in vitro cells expressing Fc receptors, such as FcγR, or CD20. The detectable label can be, e.g., a radioisotope, a fluorescent compound, an enzyme, or an enzyme co-factor.

In a particular embodiment, the invention provides methods for detecting the presence of CD20 antigen in a sample, or measuring the amount of CD20 antigen, comprising contacting the sample, and a control sample, with a human monoclonal antibody which specifically binds to CD20, under conditions that allow for formation of a complex between the antibody or portion thereof and CD20. The formation of a complex is then detected, wherein a difference complex formation between the sample compared to the control sample is indicative the presence of CD20 antigen in the sample.

In another embodiment, human antibodies of the invention can be used to detect levels of circulating CD20 or levels of cells which contain CD20 on their membrane surface, which levels can then be linked to certain disease symptoms. Alternatively, the antibodies can be used to deplete or interact with the function of CD20 expressing cells, thereby implicating these cells as important mediators of the disease. This can be achieved by contacting a sample and a control sample with the anti-CD20 antibody under conditions that allow for the formation of a complex between the antibody and CD20. Any complexes formed between the antibody and CD20 are detected and compared in the sample and the control.

Human antibodies of the invention can be initially tested for binding activity associated with therapeutic or diagnostic use in vitro. For example, the antibodies can be tested using flow cytometric assays described in the Examples below. Moreover, activity of the antibodies in triggering at least one effector-mediated effector cell activity, including inhibiting the growth of and/or killing of cells expressing CD20, can be assayed. For example, the ability of the antibodies to trigger CDC and/or apoptosis can be assayed. Protocols for assaying for CDC, homotypic adhesion, molecular clustering or apoptosis are described in the Examples below.

In still another embodiment, the invention provides a method for detecting the presence or quantifying the amount of CD20-expressing cells in vivo or in vitro. The method comprises (i) administering to a subject a composition (e.g., a multi- or bispecific molecule) of the invention conjugated to a detectable marker; (ii) exposing the subject to a means for detecting said detectable marker to identify areas containing CD20-expressing cells.

In yet another embodiment, immunoconjugates of the invention can be used to target compounds (e.g., therapeutic agents, labels, cytotoxins, radiotoxins immuno-suppressants, etc.) to cells which have CD20 expressed on their surface by linking such compounds to the antibody. Thus, the invention also provides methods for localizing ex vivo or in vitro cells expressing CD20, such as Reed-Sternberg cells (e.g., with a detectable label, such as a radioisotope, a fluorescent compound, an enzyme, or an enzyme co-factor).

The present invention is further illustrated by the following examples which should not be construed as further limiting.

EXAMPLES

| B-cell lines used in the examples | | |
|---|---|---|
| Cell line | Origin | Obtained from |
| Daudi | Negroid Burkitt's Lymphoma | ECACC (85011437) |
| Raji | Negroid Burkitt's Lymphoma | ECACC (85011429) |

Daudi and Raji B-cell lines were cultured in RPMI 1640 culture medium supplemented with 10% fetal calf serum (FCS) (Optimum C241, Wisent Inc., st. Bruno, Canada), 2 mM L-glutamine, 100 IU/ml penicillin, 100 µg/ml streptomycin, and 1 mM sodium pyruvate (all Gibco BRL, Life Technologies, Paisley, Scotland).

Cultures were maintained at 37° C. in a humidified 5% $CO_2$ incubator, split and harvested at 80-90% confluence. Medium was refreshed twice a week. At this time cells were split and seeded out to $1-1.5 \times 10^6$ cells/ml to ensure viability and optimal growth.

Example 1

Production of IgM Human Monoclonal Antibodies Against CD20

KM Mice: Fully human monoclonal antibodies to CD20 were prepared using KM mice which express human antibody genes. In the KM mouse strain, the endogenous mouse kappa light chain gene has been homozygously disrupted as described in Chen et al. (1993) *EMBO J.* 12:811-820 and the endogenous mouse heavy chain gene has been homozygously disrupted as described in Example 1 of WO 01/09187. This mouse strain carries a human kappa light chain transgene, KCo5, as described in Fishwild et al. (1996) *Nature Biotechnology* 14:845-851. This mouse strain also carries a human heavy chain transchromosome composed of chromosome 14 fragment hCF (SC20) as described in WO 02/43478.

KM Mouse Immunizations: KM mice were immunized with human CD20 transfected NS/0 cells. For the first immunization, per mouse, $1 \times 10^7$ cells in 100 µl PBS were mixed 1:1 with Complete Freunds Adjuvant and injected intraperitoneally (i.p.). Subsequent i.p. immunizations (9 immunizations in total) were done every fortnight using a similar amount of cells in phosphate buffered saline (PBS), without adjuvant. Four and three days prior to fusion the mice were intravenously boosted with $1 \times 10^5$ cells suspended in PBS.

The presence of antibodies directed against human CD20 in the serum of the mice was monitored by flow cytometry using FACS analysis, using human CD20 transfected NS/0 cells as well as CD20 negative parental NS/0 cells.

Generation of Hybridomas Producing Human Monoclonal Antibodies to CD20: The mouse splenocytes were isolated from the KM mice and fused with PEG to a mouse myeloma cell line based upon standard protocols. The resulting hybridomas were then screened for human antibody production by ELISA and for CD20 specificity using human CD20 transfected NS/0 and SKBR3 cells by FACS analysis.

More particularly, single cell suspensions of splenic lymphocytes from immunized mice were fused to one-fourth the number of SP2/0 nonsecreting mouse myeloma cells (ATCC, CRL 1581) with 50% PEG (Sigma). Cells were plated at approximately $1 \times 10^5$/well in flat bottom microtiter plates followed by about two week incubation in selective medium containing 10% fetal bovine serum (FBS), 10% P388D1 (ATCC, CRL TIB-63) conditioned medium, 3-5% origen (IGEN) in DMEM (Mediatech, CRL 10013, with high glucose, L-glutamine and sodium pyruvate) plus 5 mM HEPES, 0.055 mM 2-mercaptoethanol, 50 mg/ml gentamycin and 1×HAT (Sigma, H-0262). After 1-2 weeks, cells were cultured in medium in which the HAT was replaced with HT (Sigma, H-0137). Individual wells were then screened by flow cytometry for human anti-CD20 monoclonal antibodies. Once extensive hybridoma growth occurred, usually after 10-14 days, the medium was monitored. The antibody secreting hybridomas were replated, screened again and, if still positive for human anti-CD20 monoclonal antibodies were subcloned by limiting dilution. The stable subclones were then cultured in vitro to generate small amounts of antibody in tissue culture medium for characterization. One clone from each hybridoma, which retained the reactivity of parent cells (by FACS), was chosen. 5-10 vial cell banks were generated for each clone and stored in liquid nitrogen.

A hybridoma was chosen expressing a human monoclonal IgM anti-CD20 antibody denoted 2C6 which is characterised further in the following examples.

Example 2

Functional Characteristics of 2C6 IgM

Binding to CD20-NS/0 cells: Supernatant obtained from the 2C6 IgM clone was used to determine binding to CD20 on CD20-positive NS/0 cells. In comparison herewith rituximab (IDEC), human IgM control antibody and human IgG1 control antibody were used. The FACS staining was performed as follows: $1 \times 10^5$ cells/well in 50 µl FACS buffer (PBS, azide, bovine serum albumin (BSA)) and 50 µl supernatant or purified antibody (10 µg/ml) were incubated for 30 min at 4° C. Thereafter, the cells were washed with FACS buffer and conjugate was added to the cells (anti-human IgM-FITC or anti-human IgG-FITC for detecting rituximab, 4° C., 30 min). After washing, the cells were analyzed by flow cytometry. The data in Table 1 show that 2C6 IgM binds to CD20, albeit that fluorescence is approximately half of fluorescence after binding of rituximab.

Blocking experiments: For the blocking experiment the cells were first incubated with 2C6 IgM supernatant and in comparison herewith rituximab, human IgM control antibody and human IgG1 control antibody (4° C., 30 min), whereupon the cells were stained with rituximab-FITC (10 µg/ml) and analyzed on the FACS. The data in Table 1 below show that 2C6 IgM could not completely block binding of rituximab.

CDC activity: To determine the CDC activity of 2C6 IgM, elevated membrane permeability was assessed using FACS analysis of propidium iodide (PI)-stained cells. Briefly, Daudi cells were washed and resuspended in RPMI/1% BSA at $1 \times 10^6$ cells/ml. Various dilutions of 2C6 IgM containing supernatant and in comparison herewith rituximab, IgM control antibody and IgG1 control antibody were added to the cells and allowed to bind to CD20 expressed on the Daudi cells for 10-15 min at room temperature. Thereafter, serum as a source of complement was added to a final concentration of 20% (v/v) and the mixtures were incubated for 45 min at 37° C. The cells were then kept at 4° C. until analysis. Each sample (150 µl) was then added to 10 µl of PI solution (10 µg/ml in PBS) in a FACS tube. The mixture was assessed immediately by flow cytometry. The data in Table 1 show that 2C6 IgM can induce CDC, but to a lesser extent than rituximab.

TABLE 1

Functional characteristics of 2C6 IgM

|  | Binding[1] NS/0 | Binding[1] CD20-NS/0 | Blocking of rituximab | CDC of Daudi cells[2] |
|---|---|---|---|---|
| Rituximab | 9 | 730 | 15 | 92 |
| 2C6 IgM | 6 | 389 | 54 | 67 |
| Hu IgM control | n.d.[3] | 9 | 182 | n.d.[3] |
| Hu IgG1 control | 12 | 14 | 179 | 17 |

[1]The values are stated as mean fluorescence
[2]The values are stated as % lysis
[3]Not determined Example 3

Class Switching of 2C6 IgM to 2C6 IgG1,κ

The example discloses class switching of the 2C6 IgM antibody to an IgG1,κ antibody.

In the following all kits were used according to manufacturers' instructions unless otherwise specified.

Approximately $10^7$ hybridoma cells were collected by centrifugation (1500 rpm, 4° C.) and washed in 1 ml PBS. Cell suspension was transferred to 1.5 ml microcentrifuge tube and pelleted by centrifugation (13,000 rpm for 10 seconds).

mRNA was prepared using Quickprep-micro mRNA purification kit from Amersham Biosciences (Uppsala, Sweden).

cDNA was prepared using $1^{st}$ Strand cDNA synthesis kit from Amersham Biosciences.

Both heavy and variable chain region DNA were amplified by PCR utilising primers which recognised 5' signal sequences and 3' start of the constant region sequences for µ and κ chains:

one min, and elongation for two min at 72° C. A final elongation reaction of 10 min was performed to ensure formation of full-length transcripts.

PCR products were mixed with 2.8 µl gel loading buffer, and each sample was loaded onto a 0.7% horizontal agarose gel containing ethidium bromide and separated at 120 V, along with 1 kB DNA ladder (Gene-ruler, Fermentas AB, Vilnius, Lithuania) to allow estimation of fragment size. PCR products were visualised under UV light, excised and gel extracted using QIAEX II gel extraction kit from Qiagen (Westburg B.V., Leusden, The Netherlands).

The purified PCR products were then cloned with Zero Blunt TOPO PCR Cloning kit from Invitrogen and transformed into the kits' TOP10 chemically competent *E. coli* and plated out onto kanamycin selection LB agar plates. Individual colonies were picked and grown up overnight in kanamycin selection LB medium for DNA purification using QIAprep miniprep kit from Qiagen.

Purified DNA was selected for the presence of inserts by EcoRI (Promega) digest and sequenced. 2.5 µl of mini-prep sample that included the correct sized insert was used for each sequence reaction with the addition of 2 µl of Big Dye Terminator v1.1 Cycle Sequencing mix, 2 µl of 10× reaction buffer (Applied Biosystems, Foster City, Calif., USA) and 1 µl of T7 or SP6 primer (1 pmol/ml) and 2.5 µl water. PCR reactions were performed in an Applied Biosystems Gene-Amp PCR System 9700 for 3 hours using the standard Big-Dye protocol consisting of 25 cycles of; denaturing at 96° C. for 10 seconds, annealing at 50° C. for 5 seconds and elongation at 60° C. for 4 min, samples were then cooled to 4° C.

DNA from each PCR reaction was then precipitated by adding 1 µl of 3 M sodium acetate and 25 µl of 100% ethanol to 10 µl of sample in a 1.5 ml microcentrifuge tube and incubating the samples on ice for 10 min. DNA was pelleted by centrifugation at 16,000 g for 30 min at 4° C., then washed in 250 µl of 70% ethanol, and re-pelleted for 10 min. Ethanol was completely removed and the DNA pellet was re-suspended in 2 µl of loading buffer (1:4 of dextran:formaldehyde).

```
Primer          aa position  Sequence (5'-3')
Heavy chain 5'  -20 to -12   GGGAATTCATGGAGYTTGGGCTGASCTGGSTTTYT  (SEQ ID NO: 20)
Heavy chain 3'  125 to 120   CCCAAGCTTAGACGAGGGGGAAAAGGGTT        (SEQ ID NO: 21)
Light chain κ5' -22 to -14   GGGAATTCATGGACATGRRRDYCCHVGYKCASCTT  (SEQ ID NO: 22)
Light chain κ3' 122 to 117   CCCAAGCTTCATCAGATGGCGGGAAGAT         (SEQ ID NO: 23)
```

Variations in the target sequence were allowed for by using degenerate primers where: D=A or T or G; H=A or T or C; K=T or G; R=A or G; S=C or G; V=A or C or G; and Y=C or T.

DNA amplification was performed utilising Pfu polymerase (Promega, Southampton, UK) to decrease the number of replicable errors inserted into the DNA sequence of interest. Briefly, 1 µl of the applicable 5' and 3' primer (100 ng/ml) was added to 0.5 µl of cDNA with 2.5 µl of Pfu reaction buffer and 0.5 µl of dNTP mix, together with 0.5 µl of Pfu polymerase (5 U/µl) in a total volume of 25 µl.

The PCR reactions were run using a PTC-100 thermal control system (MJ Research Inc., Waltham, Mass., USA). DNA was denatured at 94° C. for 5 min, followed by 30 cycles of denaturing at 94° C. for 30 seconds, annealing at 55° C. for DNA sequence samples were run on a Perkin Elmer ABI Prism 377 DNA Sequencer (Fremont, Calif., USA) and analysed using DNASTAR Sequence Manager software (Madison, Wis., USA).

The obtained sequences were compared to the known sequences and new primers designed which would introduce restriction sites for cloning with constant region sequences:

```
Primer         Sequence (5'-3')
                                                    (SEQ ID NO: 24)
                       HindIII
Heavy Chain    ATAAGCTTCAGGACTCACCATGGAGTTTGGGCTGAGC
5'
                                                    (SEQ ID NO: 25)
                       SpeI
```

-continued

| Primer | Sequence (5'-3') |
|---|---|
| Heavy Chain 3' | GGTGACTAGTGTCCCTTGGCCCCA |
| | (SEQ ID NO: 26) |
| | HindIII |
| Light Chain κ5' | ATAAGCTTCAGGACTCACCATGGACATGGAGGCCCCG |
| | (SEQ ID NO: 27) |
| | BsiWI |
| Light Chain κ3' | CACCGTACGTTTGATCTCCACCTT |

Light and heavy chain variable regions with inserted restriction sites were produced by PCR as detailed in the first PCR above, with the exception that the annealing temperature was altered to 50° C.

The PCR products were isolated and sub-cloned into TOPO blunt end PCR vectors and sequenced as detailed above.

The obtained sequences were compared to the source sequences and then digested with HindIII/SpeI for the heavy chain or HindIII/BsiWI for the light chain alongside vectors containing human IgG constant regions for IgG1 and K chains respectively. The digest products were visualised and extracted as previously detailed. The digested fragments were then ligated using T4 DNA ligase (Promega) overnight at 4° C. and transformed into chemically competent JM109 *E. coli* (Promega) and plated out onto ampicillin selection LB agar plates. Individual colonies were picked and grown up overnight in ampicillin selection LB media for DNA purification using QIAprep miniprep kit from Qiagen and subsequent diagnostic digest with the appropriate restriction enzymes.

Once ligated with their constant regions, the full length heavy and light chains were then extracted by double restriction digest using HindIII and EcoRI alongside pEE6.1 and pEE14.1 mammalian expression vectors respectively (Lonza Biologics, Slough, UK). The digested fragments were then ligated using T4 DNA ligase (Promega) overnight at 4° C. and transformed into chemically competent JM109 *E.coli* (Promega) and plated out onto ampicillin selection LB agar plates. Individual colonies were picked and grown up overnight in ampicillin selection LB media for DNA purification using QIAprep miniprep kit from Qiagen and subsequent diagnostic digest with the appropriate restriction enzymes.

This experiment revealed that 2C6 has the $V_H$ nucleotide sequence SEQ ID NO:1 and amino acid sequence SEQ ID NO:2. Furthermore, the 2C6 hybridoma expresses two light variable chains, $V_L$a 2C6 with nucleotide sequence SEQ ID NO:3 and amino acid sequence SEQ ID NO:4, and $V_L$b 2C6 with amino acid sequence SEQ ID NO:5.

Example 4

Transient Transfection of 2C6 Heavy Chain and 11B8 Light Chain Using Freestyle 293 Expression System (Invitrogen, Breda, The Netherlands)

HEK293F cells were obtained from Invitrogen and transfected with 2C6 heavy chain IgG1 DNA and 11B8 K light chain DNA according to the manufacturer's instructions, using 293fectin. The recombinant antibody is denoted 2C6 IgG1,κ and is used in the experiments disclosed in the following examples. The production of human monoclonal anti-CD20 antibody 11B8 is disclosed below.

Production of Human Monoclonal Antibody 11B8 Binding to CD20

HCo7 Immunization: HCo7 mice were immunized with human CD20 transfected NS/0 cells. For the first immunization, per mouse, $1\times10^7$ cells in 150 μl PBS were mixed 1:1 with Complete Freunds Adjuvant and injected intraperitoneally (i.p.). Subsequent i.p. immunizations were done using a similar amount of cells in PBS without adjuvant. Three and two days prior to fusion the mice were intravenously boosted with $0.5\times10^7$ cells suspended in PBS.

The HCo7 mice have a JKD disruption in their endogenous light chain (kappa) genes (as described in Chen et al. (1993) *EMBO J.* 12:821-830), a CMD disruption in their endogenous heavy chain genes (as described in Example 1 of WO 01/14424), a KCo5 human kappa light chain transgene (as described in Fishwild et al. (1996) *Nature Biotechnology* 14:845-851), and a HCo7 human heavy chain transgene (as described in U.S. Pat. No. 5,770,429).

The presence of antibodies directed against human CD20 in the serum of the mice was monitored by flow cytometry using FACS analysis, using human CD20 transfected NS/0 cells as well as CD20 negative parental NS/0 cells.

The mouse splenocytes were isolated from the HCo7 mice and fused with PEG to a mouse myeloma cell line based upon standard protocols. The resulting hybridomas were then screened for human IgG,κ production by ELISA and for CD20 specificity using human CD20 transfected NS/0 and SKBR3 cells by FACS analysis. Single cell suspensions of splenic lymphocytes from immunized mice were fused to one-fourth the number of SP2/0 nonsecreting mouse myeloma cells (ATCC, CRL 1581) with 50% PEG (Sigma). Cells were plated at approximately $1\times10^5$/well in flat bottom microtiter plate, followed by about two week incubation in selective medium containing 10% fetal bovine serum, 10% P388D1 (ATCC, CRL TIB-63) conditioned medium, 3-5% origen (IGEN) in DMEM (Mediatech, CRL 10013, with high glucose, L-glutamine and sodium pyruvate) plus 5 mM HEPES, 0.055 mM 2-mercaptoethanol, 50 mg/ml gentamycin and 1×HAT (Sigma, CRL P-7185). After 1-2 weeks, cells were cultured in medium in which the HAT was replaced with HT. Individual wells were then screened by flow cytometry for human anti-CD20 monoclonal IgG antibodies. Once extensive hybridoma growth occurred, usually after 10-14 days, medium was monitored. The antibody secreting hybridomas were replated, screened again and, if still positive for human IgG, anti-CD20 monoclonal antibodies were subcloned by limiting dilution. The stable subclones were then cultured in vitro to generate small amounts of antibody in tissue culture medium for characterization. One clone from each hybridoma, which retained the reactivity of parent cells (by FACS), was chosen. 5-10 vial cell banks were generated for each clone and stored in liquid nitrogen.

The following hybridoma was generated from the HCo7 mouse, expressing a human monoclonal IgG3,κ anti-CD20 antibody denoted 11B8.

The 11B8 antibody was sequenced according to standard techniques in a similar manner as disclosed in Example 3 using appropriate primers. The 11B8 antibody has the $V_L$ nucleotide sequence as set forth in SEQ ID NO:6, and the $V_L$ amino acid sequence as set forth in SEQ ID NO:7. The $V_H$ region has the following amino acid sequence:

Met Glu Leu Gly Leu Ser Trp Val Phe Leu Val Ala Ile Leu Lys
Gly Val Gln Cys Glu Val Gln Leu Val Gln Ser Gly Gly Gly Leu
Val His Pro Gly Gly Ser Leu Arg Leu Ser Cys Thr Gly Ser Gly
Phe Thr Phe Ser Tyr His Ala Met His Trp Val Arg Gln Ala Pro
Gly Lys Gly Leu Glu Trp Val Ser Ile Ile Gly Thr Gly Gly Val

Thr Tyr Tyr Ala Asp Ser Val Lys Gly Arg Phe Thr Ile Ser Arg
Asp Asn Val Lys Asn Ser Leu Tyr Leu Gln Met Asn Ser Leu
Arg Ala Glu Asp Met Ala Val Tyr Tyr Cys Ala Arg Asp Tyr Tyr
Gly Ala Gly Ser Phe Tyr Asp Gly Leu Tyr Gly Met Asp Val Trp
Gly Gln Gly Thr Thr Val Thr Val Ser Ser (SEQ ID NO:28).

Example 5

Binding Characteristics of 2C6 IgG1,κ Against CD20

Binding to Daudi and Raji cell lines: Daudi and Raji cells were incubated for 30 min at 4° C. with FITC conjugated human antibodies: 2C6 IgG1,κ, or the reference antibodies, rituximab, 2F2, or 11B8. Binding was assessed by flow cytometry. As shown in FIGS. 1A and 1B, 2C6 IgG1,κ bound to the two different Burkitt lymphoma B cell lines indicating that 2C6 IgG1,κ retains the binding characteristics of the original 2C6 IgM antibody.

2F2 is a human monoclonal IgG1,κ anti-CD20 antibody raised in a KM mouse having the variable $V_H$ amino acid sequence:

Met Glu Leu Gly Leu Ser Trp Ile Phe Leu Leu Ala Ile Leu Lys
Gly Val Gln Cys Glu Val Gln Leu Val Glu Ser Gly Gly Gly Leu
Val Gln Pro Gly Arg Ser Leu Arg Leu Ser Cys Ala Ala Ser Gly
Phe Thr Phe Asn Asp Tyr Ala Met His Trp Val Arg Gln Ala Pro
Gly Lys Gly Leu Glu Trp Val Ser Thr Ile Ser Trp Asn Ser Gly
Ser Ile Gly Tyr Ala Asp Ser Val Lys Gly Arg Phe Thr Ile Ser
Arg Asp Asn Ala Lys Lys Ser Leu Tyr Leu Gln Met Asn Ser
Leu Arg Ala Glu Asp Thr Ala Leu Tyr Tyr Cys Ala Lys Asp Ile
Gln Tyr Gly Asn Tyr Tyr Tyr Gly Met Asp Val Trp Gly Gln Gly
Thr Thr Val Thr Val Ser (SEQ ID NO:29)

and the variable $V_L$ amino acid sequence:

Met Glu Ala Pro Ala Gln Leu Leu Phe Leu Leu Leu Leu Trp
Leu Pro Asp Thr Thr Gly Glu Ile Val Leu Thr Gln Ser Pro Ala
Thr Leu Ser Leu Ser Pro Gly Glu Arg Ala Thr Leu Ser Cys Arg
Ala Ser Gln Ser Val Ser Ser Tyr Leu Ala Trp Tyr Gln Gln Lys
Pro Gly Gln Ala Pro Arg Leu Leu Ile Tyr Asp Ala Ser Asn Arg
Ala Thr Gly Ile Pro Ala Arg Phe Ser Gly Ser Gly Ser Gly Thr
Asp Phe Thr Leu Thr Ile Ser Ser Leu Glu Pro Glu Asp Phe Ala
Val Tyr Tyr Cys Gln Gln Arg Ser Asn Trp Pro Ile Thr Phe Gly
Gln Gly Thr Arg Leu Glu Ile Lys (SEQ ID NO:30).

The 2F2 antibody used in the experiments is produced recombinantly in CHO cells.

The 11B8 antibody used in the experiments is also produced recombinantly in CHO cells.

FIG. 1 also shows that 2C6 IgG1,κ exhibits similar apparent $K_D$ as the reference antibodies, indicating that 2C6 IgG1,κ binds with similar affinity.

Figure 2:
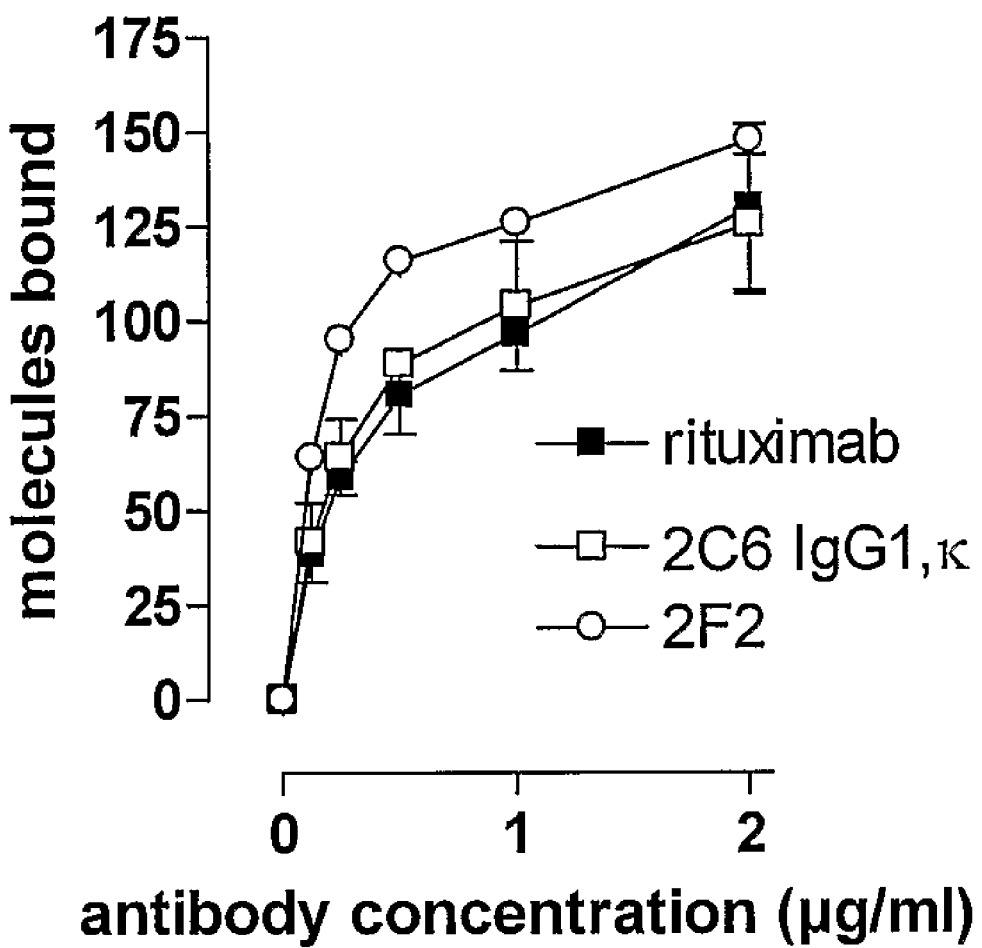
FIG. 2 shows the binding of 2C6 IgG1,κ, and in comparison herewith rituximab and 2F2), to Daudi cells.

Binding of $^{125}$I-labeled anti-CD20 monoclonal antibodies to Daudi cells: $^{125}$I-labeled anti-CD20 monoclonal antibodies (2C6 IgG1,κ, and the reference antibodies, rituximab and 2F2) were incubated with Daudi cells for 2 hours at room temperature at different concentrations. The cell-bound and free $^{125}$I-labeled anti-CD20 monoclonal antibodies were then separated by centrifugation through phthalate oils, and the cell pellets together with bound antibody were counted for radioactivity in a gamma counter The results are shown in FIG. 2. All antibodies tested bound in a similar way to Daudi cells and saturated at 0.5 μg/ml.

Figure 3:
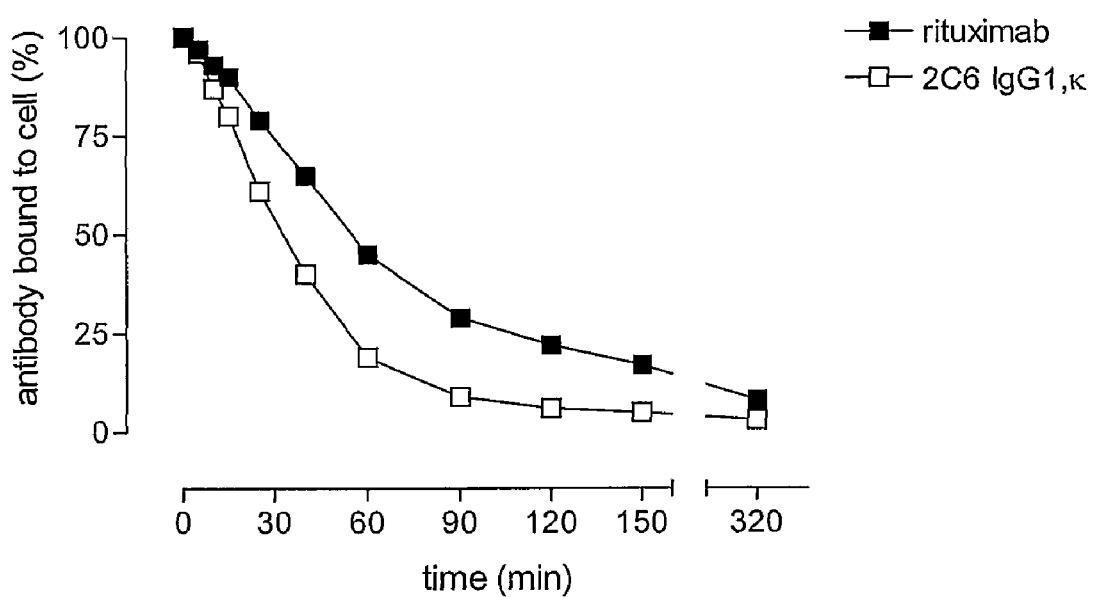
FIG. 3 shows the dissociation rate of 2C6 IgG1,κ, and in comparison herewith rituximab, in Raji cells over time.

Dissociation rate: To determine the dissociation rate of the monoclonal anti-bodies, Raji cells were incubated for 10 min at room temperature with 10 μg/ml FITC-conjugated monoclonal antibodies to achieve maximum binding. The Raji cells were washed and incubated in the presence of a high concentration of unlabeled antibody (200 μg/ml). The maximal (initial) binding to Raji cells was set at 100%. At several time points over the next 320 min following loading, 1×10$^5$ cells were removed from each sample to determine the levels of FITC monoclonal antibody remaining on the cell surface. As can be seen from FIG. 3, 2C6 IgG1,κ dissociated faster from the surface of Raji cells than rituximab. At approximately 55 min, approximately 50% of the rituximab molecules were still bound to the cell, whereas 50% of the 2C6 IgG1,κ molecules dissociated after approximately 35 min.

Figure 4:
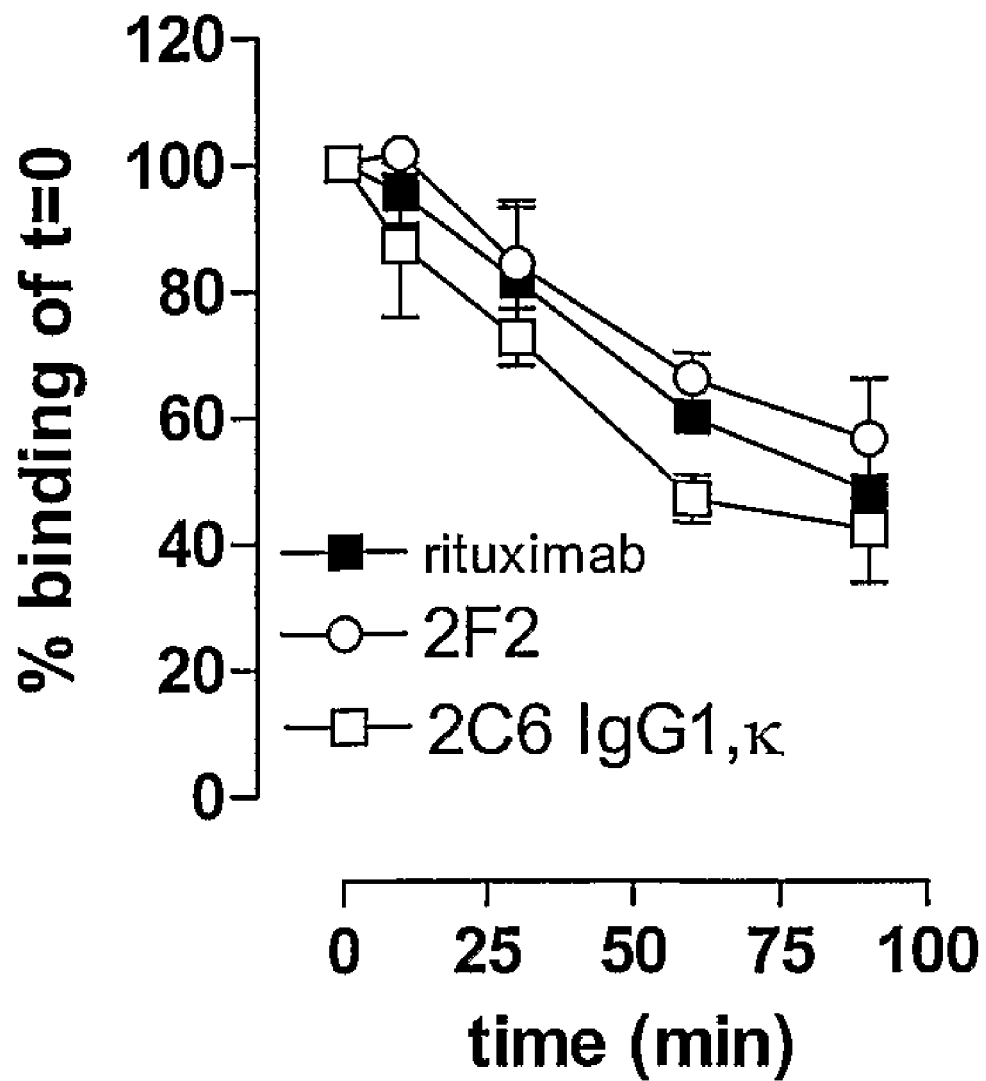
FIG. 4 shows the dissociation rate of 2C6 IgG1,κ, and in comparison herewith rituximab and 2F2, in Daudi cells over time.

Dissociation rate of $^{125}$I-labeled anti-CD20 monoclonal antibodies from Daudi cells: $^{125}$I-labeled anti-CD20 monoclonal antibodies (2C6 IgG1,κ, and the reference antibodies, rituximab and 2F2) (2 μg/ml) were added to Daudi cells, incubated for 1 hour at room temperature, and then pelleted and resuspended in 600 μl medium containing 1 mg/ml of unlabeled monoclonal antibody. Cells were kept at room temperature and at various times aliquots were taken to determine the level of cell-bound monoclonal antibodies by counting for radioactivity in a gamma counter. Counts remaining at each time point were expressed as a percentage of the initial count. FIG. 4 shows the mean of 2-4 experiments. As can be seen from FIG. 4 2C6 IgG1,κ dissociates faster than rituximab.

Example 6

CDC of 2C6 IgG1,κ

Serum preparation: Serum for complement lysis was prepared by drawing blood from healthy volunteers into autosep gel and clot activator vacutainer tubes (BD biosciences, Rutherford, N.J.) which were held at room temperature for 30-60 min and then centrifuged at 3000 rpm for 5 min. Serum was harvested and stored at −80° C.

Flow cytometry: For flow cytometry a FACScalibur flow cytometer was used with CellQuest pro software (BD Biosciences, Mountain view, Calif.). At least 5000 events were collected for analysis with cell debris excluded by adjustment of the forward sideward scatter (FCS) threshold.

CDC activity of anti-CD20 in B cell line cells: To determine the CDC activity of each antibody, elevated membrane permeability was assessed using FACS analysis of PI-stained cells.

Raji or Daudi cells were pre-incubated with a concentration range of 2C6 IgG1,κ, 2F2, 11B8, rituximab and control antibody (anti-KLH), respectively, for 10 min before NHS was added. After 45 min incubation at 37° C. when maximal lysis occurs the cells were resuspended in PI solution and cell lysis (number of PI-positive cells) was measured by flow cytometry.

Figure 5A:
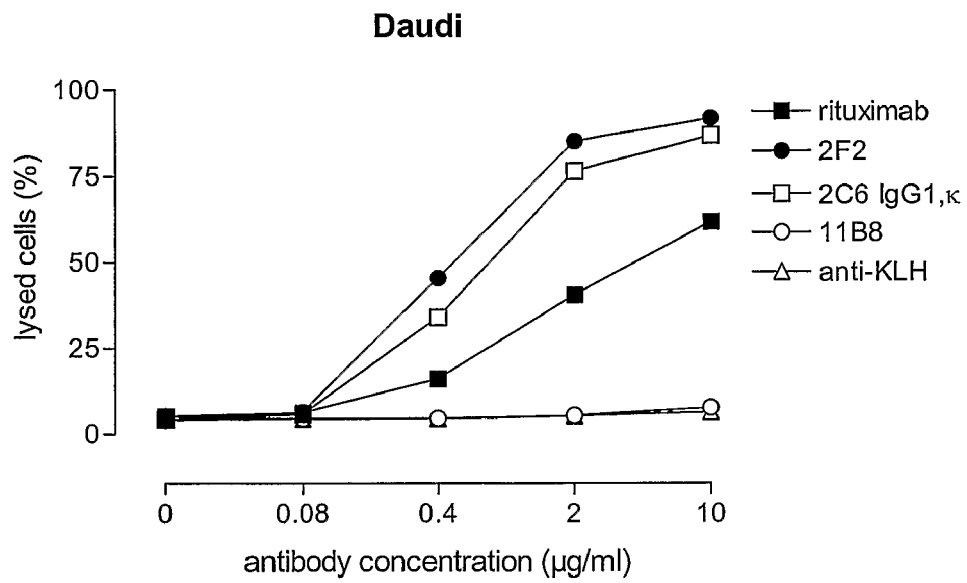
FIGS. 5A and 5B show the antibody concentration-dependent induction of CDC (complement dependent cytoxicity) of Daudi cells (FIG. 5A) or Raji cells (FIG. 5B) by 2C6 IgG1,κ, and in comparison herewith rituximab, 2F2, 11B8, and a human monoclonal isotype control antibody (anti-KLH), using flow cytometry.
Figure 5B:
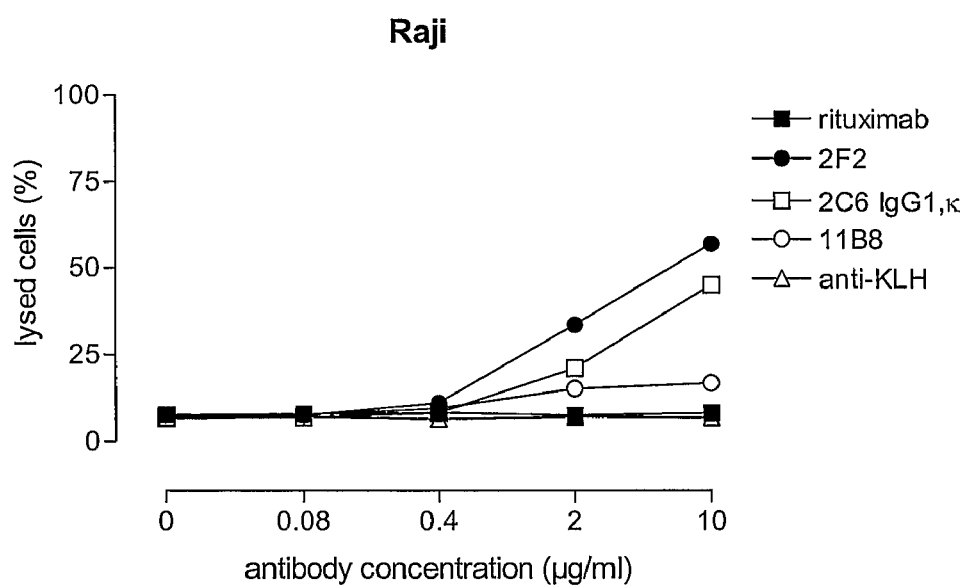
Figure 6:
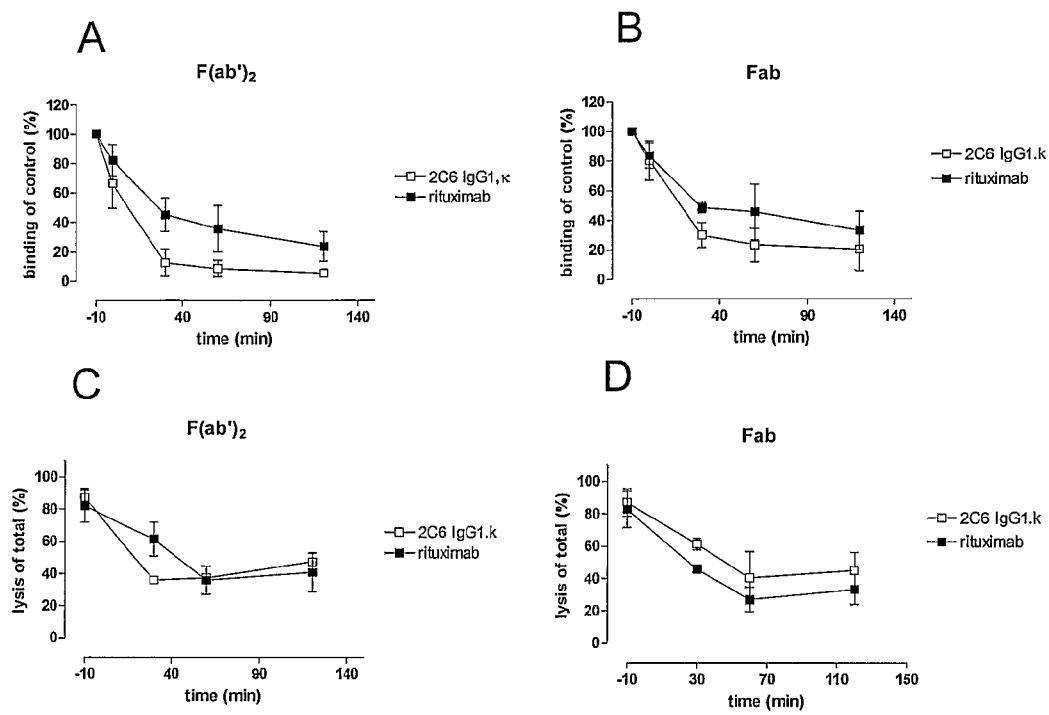
FIG. 6 show the dissociation of 2C6 IgG1,κ, and in comparison herewith rituximab, from Daudi cells at various point of times (FIGS. 6A and 6B) and the ability of the antibodies to induce CDC (FIGS. 6C and 6D) in the presence of NHS at these point of times.

FIGS. 5A (Daudi cells), and 5B (Raji cells) show the percentage of lysed (PI-positive) cells as a function of antibody concentration. 2C6 IgG1,κ as well as the reference antibodies, 2F2 and rituximab, induce a concentration-dependent increase in cell lysis of Daudi cells. Importantly, 2C6 IgG1,κ induced more than 80% lysis of Daudi cells upon addition of 2 μg/ml, whereas with rituximab this level was not reached even after addition of 10 μg/ml. Induction of lysis of Raji cells by 2C6 IgG1,κ was lower than Daudi cells, but still approximately 50% lysis was reached at an antibody concentration of 10 μg/ml. Even at its highest concentration, rituximab was not able to induce lysis of Raji cells.

Example 7

Binding and CDC Activity Over Time

Daudi cells were incubated with FITC-labeled anti-CD20 monoclonal antibodies (2C6 IgG1,κ and the reference antibody, rituximab) (5 μg/ml) for 60 min at 37° C. to allow binding to cells. A small volume of highly concentrated F(ab')$_2$ or Fab' fragments of rituximab was added to the cells (final concentration 300 μg/ml) to compete with the bound FITC-labeled anti-CD20 monoclonal antibodies. At various time points samples were taken, which were split into two parts. One part of the sample was used to determine the amount of FITC monoclonal antibodies bound to the cells (FIGS. 6A and 6B). The other part was treated with normal human serum (NHS) (20% vol/vol), and the cells were incubated at 37° C. for 15 min. Cell lysis was assessed by flow cytometry using a PI exclusion assay, and the level of CDC is expressed as PI-positive cells as percentage of the total cells (FIGS. 6C and 6D). The figures show the mean (±SEM) of 3 separate experiments.

These experiments show that rituximab and 2C6 IgG1,κ remained bound to the cells immediately after addition of the competitor and, as expected, dissociated from the cells more gradually. These experiments also show that although 2C6 IgG1,κ dissociates faster from the cells than rituximab, the ability to induce cell lysis were similar between rituximab and 2C6 IgG1,κ. Compared to rituximab, the number of 2C6 IgG1,κ molecules required to give comparable levels of lysis was less. These data suggest that the density of anti-CD20 monoclonal antibody bound to cells is not the only factor that determines lysis.

Example 8

Generation of Anaphylatoxins (C3a, C4a, C5a)

Figure 7:
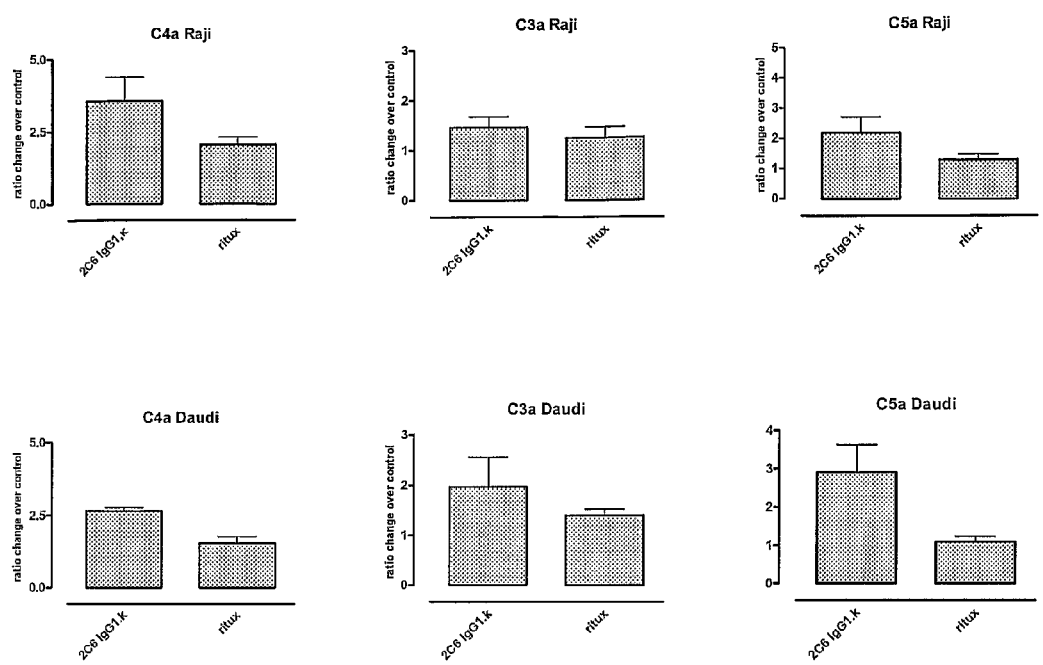
FIG. 7 shows the generation of the anaphylatoxins (C3a, C4a and C5a) in a complement activation assay using Raji cell and Daudi cell targets, by 2C6 IgG1,κ, and in comparison herewith rituximab, in the presence of NHS.

Raji or Daudi cells were incubated with saturating amounts of anti-CD20 monoclonal antibodies (2C6 IgG1,κ, and the reference antibody, rituximab) (10 μg/ml) for 30 min at room temperature to allow binding to cells. NHS (20% vol/vol) was added to the cells followed by incubation at 37° C. for 15 min. The cells were spun down and supernatant was appropriately diluted in the presence of a protease inhibitor FUT-175 to prevent further complement activation. Anaphylatoxins were measured using a cytometric bead array from Becton Dickinson, according to the manufacturers instructions. FIG. 7 shows the mean and SD of 4 separate experiments.

In Raji cells, production of anaphylatoxins was similar between the tested anti-CD20 monoclonal antibodies. In Daudi cells high analyphylatoxin production was observed by 2C6 IgG1,κ and rituximab. Differences between 2C6 IgG1,κ and rituximab were not significant.

Example 9

ADCC of 2C6 IgG1,κ

Preparation $^{51}$Cr-labeled target cells: Raji cells were collected (5×10$^6$ cells) in RPMI containing 10% fetal calf serum and pen/strep (RPMI++), spun down (1500 rpm; 5 min), resuspended in 140 μl $^{51}$Cr (Chromium-51; 140 μl is about 100 μCi) and incubated (37° C. water bath, 1 hour). After washing cells (1500 rpm, 5 min, in PBS, 3×), cells were resuspended in RPMI++ and counted by trypan blue exclusion. Cells were brought at concentration of 1×10$^5$ cells/ml.

Preparation of effector cells: Fresh peripheral blood mononuclear cells (PBMCs) were isolated from heparin anti-coagulated blood by Ficoll (Bio Whittaker; lymphocyte separation medium, cat 17-829E) using the manufacturer's instructions. After resuspension of cells in RPMI++, cells were counted by trypan blue exclusion and adjusted to a concentration of 1×10$^6$ cells/ml.

ADCC set up: 50 μl RPMI++was pipetted into 96 wells plates, and 50 μl of $^{51}$Cr-labeled targets cells were added. Thereafter, 50 μl of antibody was added, diluted in RPMI++ (final concentrations 10, 1, 0.1 μg/ml). Cells were incubated (room temperature, 10 min), and 50 μl effector cells were added, resulting in an effector to target ratio of 100:1 (for determination of maximal lysis, 50 μl 5% Triton-X-100 was added instead of effector cells). Cells were spun down (500 rpm, 5 min), and incubated (37° C., 5% CO$_2$, 4 hours). After spinning the cells (1500 rpm, 5 min), 100 μl of supernatant was harvested into micronic tubes, and counted in a gamma counter. The percentage specific lysis was calculated as follows:

$$\% \text{ specific lysis} = (cpm \text{ sample} - cpm \text{ target cells only}) / (cpm \text{ maximal lysis} - cpm \text{ target cells only}) \times 100$$

Figure 8:
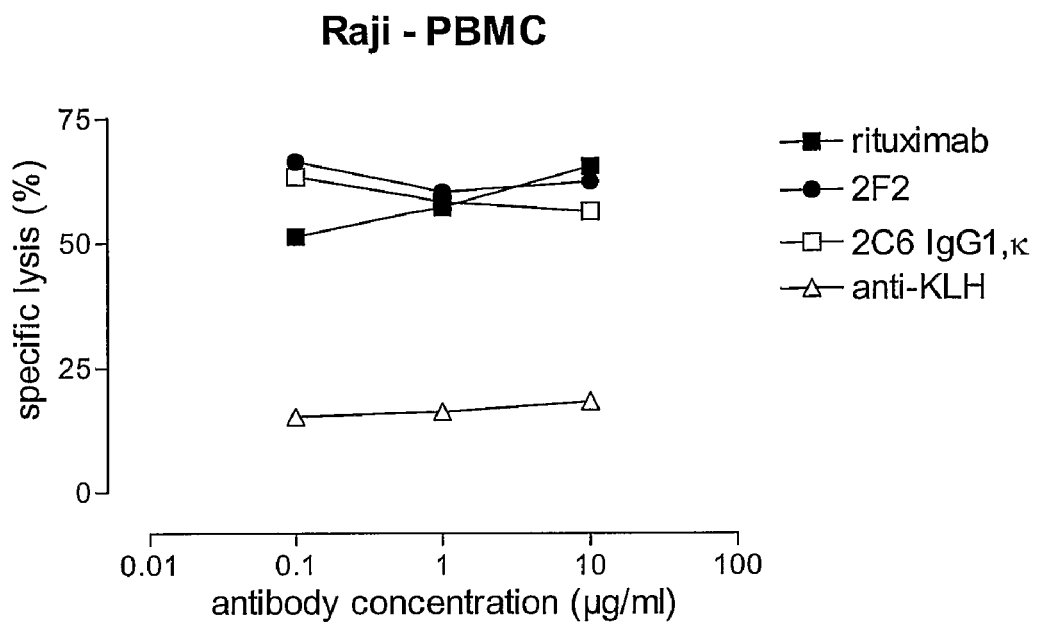
FIG. 8 shows lysis of $^{51}$Cr-labeled Raji cells in the presence of peripheral blood mononuclear cells (PBMCs) by 2C6 IgG1,κ, and in comparison herewith rituximab, 2F2, and an isotype control antibody (anti-KLH), at different antibody concentrations.

Antibody concentration-dependent lysis of Rafi cells: When Raji cells were used as target cells, 2C6 IgG1,κ induced peripheral blood mononuclear cell (PBMC)-mediated lysis of Raji cells (maximum lysis reached with 2C6 IgG1,κ was approximately 63%), at similar levels as 2F2 and rituximab, see FIG. 8. Spontaneous lysis was approximately 20%. Addition of the isotype control antibody (anti-KLH) did not induce ADCC. No specific lysis was observed without PBMCs (data not shown).

Example 10

Apoptosis of Burkitt Cell Lines with 2C6 IgG1,κ

Apoptosis: Daudi or Raji cells, 0.5×10$^6$ in 1 ml tissue culture medium, were placed into 24-well flat-bottom plates with 1 or 10 μg/ml 2C6 IgG1,κ or control antibodies, anti-CD20 antibody B1, the isotype control antibody anti-KLH, or without antibody, and incubated at 37° C. After 20 hours, cells were harvested, washed in Annexin-V-FITC binding buffer (BD biosciences) and labeled with Annexin V-FITC (BD biosciences) for 15 min in the dark at 4° C. The cells were kept at 4° C. until analysis. Each sample (150 μl) was added to 10 μl of PI solution (10 μg/ml in PBS) in a FACS tube. The mixture was assessed immediately by flow cytometry using a FACScalibur flow cytometer with CellQuest pro software (BD Biosciences, Mountain view, Calif.). At least 10,000 events were collected for analysis.

Figure 9:
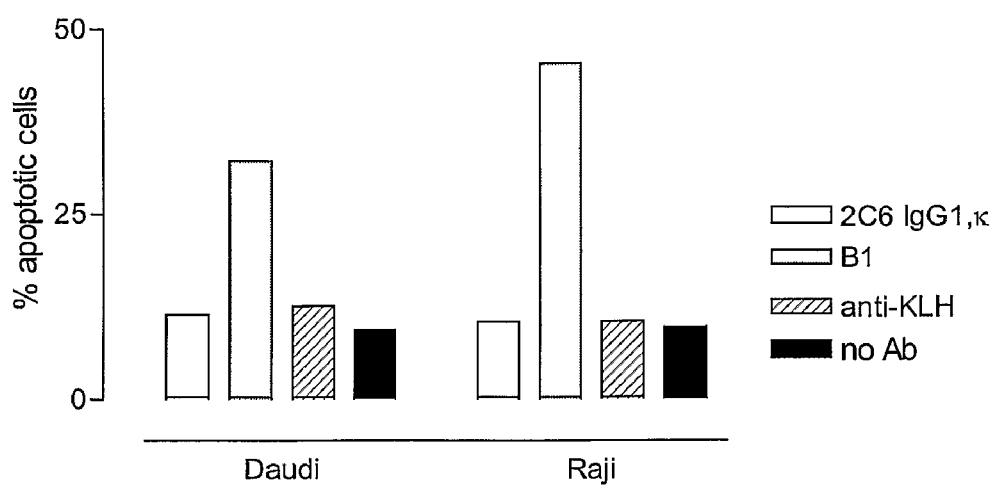
FIG. 9 shows induction of apoptosis of Daudi or Raji cells by 2C6 IgG1,κ, and in comparison herewith B1 (the unlabeled form of Bexxar™, which is a $^{131}$I-labeled murine anti-human CD20 antibody, Coulter), an isotype control antibody (anti-KLH), and in the absence of antibodies, after incubation for 20 hours.

Data in FIG. 9 show mean of two experiments. 2C6 shows no sign of apoptosis induction in both cell lines, and was similar to the isotype control antibody. As expected, the reference antibody B1 did induce apoptosis (30-40%) in both B-cell lines.

Example 11

Homotypic Adhesion of Cells with 2C6 IgG1,κ

Homotypic adhesion correlates with induction of apoptosis. Therefore, the ability of the anti-CD20 monoclonal antibodies to induce homotypic adhesion of B cells was investigated.

Figure 10A:
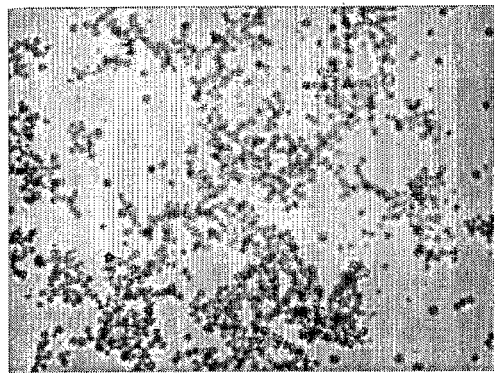
FIGS. 10A and 10B show homotypic adhesion of Daudi cells (FIG. 10A) or Raji cells (FIG. 10B) by 2C6 IgG1,κ, and in comparison herewith rituximab, 11B8, and an isotype control antibody (anti-KLH), using light microscopy.
Figure 10A:
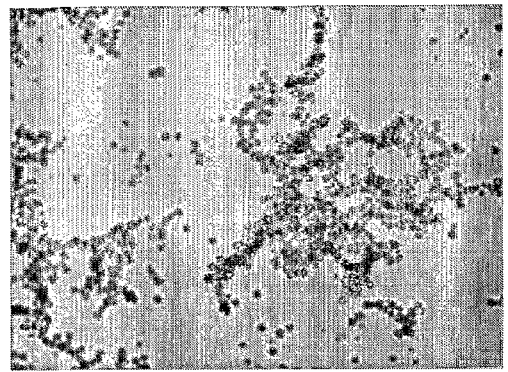
Figure 10A:
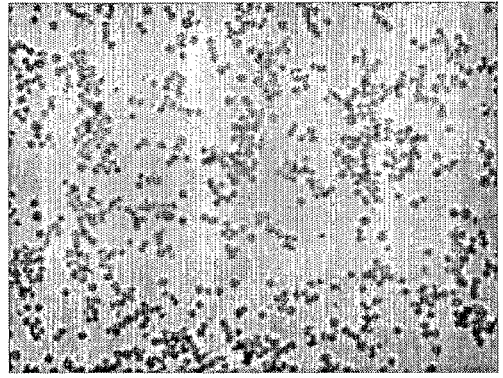
Figure 10A:
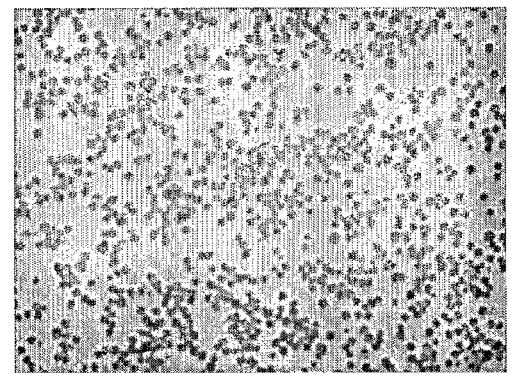
Figure 10B:
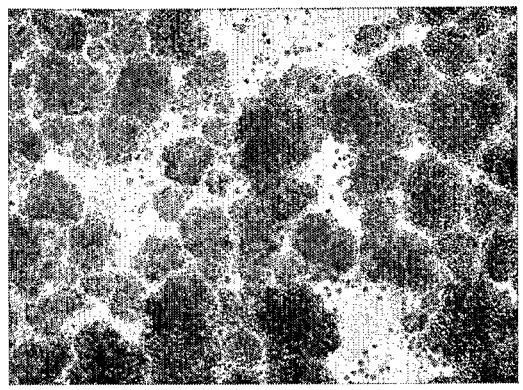
Figure 10B:
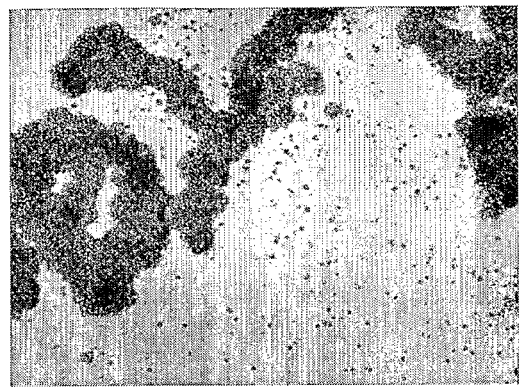
Figure 10B:
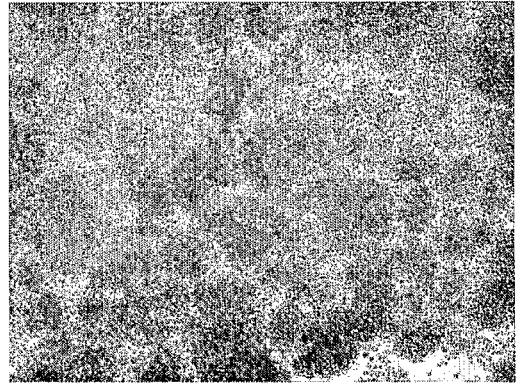
Figure 10B:
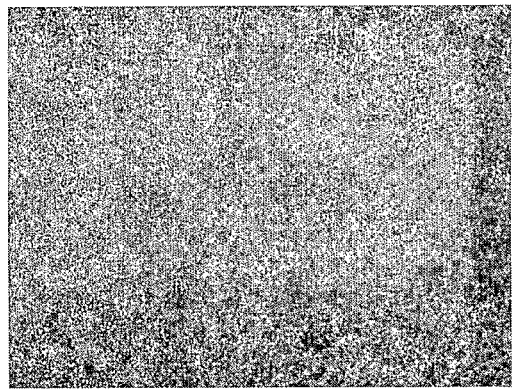

Homotypic adhesion of Daudi cells and Raji cells: Daudi or Raji cells were placed into 24-well flat-bottom plates with 1 or 10 μg/ml anti-CD20 monoclonal antibodies or control antibody (anti-KLH), and incubated at 37° C. for 4 hours. The extent of homotypic adhesion was determined by light microscopy. As can be seen from FIG. 10, 2C6 IgG1,κ poorly induced homotypic adhesion of Daudi (FIG. 10A) or Raji (FIG. 10B) cells, with 1.0 μg/ml (and 10 μg/ml, data not shown). Rituximab gave some homotypic adhesion of Daudi and Raji cells. In contrast, 11B8 was a strong inducer of homotypic adhesion.

Example 12

Epitope Mapping Using Site-Directed Mutagenesis

Epitope mapping studies using a mutagenesis approach have indicated that alanine at position 170 (A170) and proline at position 172 (P172) in the second extracellular loop are critical for the recognition of human CD20 by known anti-CD20 antibodies. In studies by Deans and colleagues (M. J. Polyak, et al., (2002) *Blood* 99(9): pp 3256-3262) the binding of all anti-CD20 monoclonal antibodies tested was abrogated by changing A170 and P172 into the corresponding murine CD20 residues S170 and S172. To verify whether the A170xP172 motive is also important for the binding of the antibodies according to the invention the AxP sequence was mutated into SxS using site-directed mutagenesis (AxP mutant=A170S, P172S), cells were transfected with the AxP mutant and wild-type (WT) CD20 DNA, and the binding characteristics of the anti-CD20 monoclonal antibodies were compared.

Further mutants were prepared, P172S (proline at position 172 mutated to serine), N166D (asparagine at position 166 mutated to aspartic acid), and N163D (asparagine at position 163 mutated to aspartic acid), using site-directed mutagenesis to evaluate whether the mutated amino acid residues are important for binding of the antibodies of the invention.

To examine this, a CD20 expression vector was constructed by amplifying the CD20 coding sequence using suitable primers introducing restriction sites and an ideal Kozak sequence for optimal expression. The amplified fragment was digested and ligated in the expression vector pEE13.4 (Lonza, Slough, UK). After transformation in *E. coli*, colonies were screened for inserts and two clones were selected for sequencing to confirm the correct sequence. The construct was named pEE13.4CD20HS.

Mutagenesis was performed to introduce the AxP mutation and to introduce 20 mouse mutations in the extracellular loop regions of human CD20. Mutagenesis was checked by restriction enzyme digestion and sequencing. The constructs were transiently transfected in CHO cells (for AxP mutations) or HEK293F cells and analyzed 24 or 48 hours post-transfection using flow cytometry.

Oligonucleotide PCR Primers: Oligonucleotide primers were synthesized and quantified by Isogen BV (Maarssen, The Netherlands). Primers were reconstituted in water in a concentration of 100 μmol/μl and stored at −20° C. until required. A summary of PCR and sequencing primers is shown in Table 2.

Optical density determination of nucleic acids: Optical density was determined using an Ultrospec 2100 pro Classic (Amersham Biosciences, Uppsala, Sweden) according to the manufacturer's instructions. The DNA concentration was measured by analysis of the OD260 nm, where one OD260 nm unit=50 μg/ml. The reference solution was identical to the solution used to dissolve the nucleic acids.

Plasmid DNA isolation from *E. coli* culture: Plasmid DNA was isolated from *E. coli* cultures using kits from Qiagen according to the manufacturer's instructions (Westburg BV, Leusden, The Netherlands). For 'bulk' plasmid preparation either a Hi-Speed plasmid Maxi kit or a Hi-Speed plasmid Midi kit were used (Qiagen). For a small scale plasmid preparation (i.e., 2 ml of *E. coli* culture) a Qiaprep Spin Miniprep Kit (Qiagen) was used and the DNA eluted in 50 μl TE (Tris-HCl 10 mM pH 8.0, EDTA 1 mM).

PCR amplification: PCR reactions were performed according to the manufacturer's instructions for the Pfu-Turbo© Hotstart DNA polymerase (Stratagene, Amsterdam, The Netherlands). Each 20 μl reaction contained 1×PCR reaction buffer, 200 μM mixed dNTPs, 6.7 μmol of each forward and reverse primer, approximately 1 ng template DNA and 1 unit of Pfu-Turbo© Hotstart DNA polymerase. PCR reactions were performed on a T-gradient Thermocycler 96 (Biometra GmbH, Goettingen, Germany) using a 30 cycle program of: +95° C. for 2 min, followed by 30 cycles of: +95° C. for 30 sec, anneal: a gradient of 45-65° C. for 30 sec and extension: +72° C. for 2 min, followed by a final extension step of 10 min at 72° C. and subsequent storage at 4° C. The completed reactions were analysed by agarose gel electrophoresis.

Agarose gel electrophoresis: Agarose gel electrophoresis was performed according to Sambrook (Molecular Cloning Laboratory Manual, 3rd edition) using gels of 50 ml, in 1× Tris/acetic acid/EDTA (TAE) buffer. DNA was visualized by the inclusion of ethidium bromide in the gel and observation under UV light. Gel images were recorded by a CCD camera and an image analysis system (GeneGnome; Syngene, Cambridge, UK).

Restriction enzyme digestions: Restriction enzymes were supplied by New England Biolabs (Beverly, Mass.) and used according to the supplier's recommendations. In general, 100 ng was digested with 5 units of enzyme(s) in appropriate buffer in a final volume of 10 μl. Reaction volumes were scaled up as appropriate. Digestions were incubated for a minimum of 60 min at the manufacturer's recommended temperature.

For fragments requiring double digestions with restriction enzymes which have incompatible buffer or temperature requirements, digestions were performed sequentially so as to offer favourable conditions for each enzyme in turn.

Alkaline phosphatase treatment: Shrimp alkaline phosphatase (USB, Cleveland, Ohio) was used according to the supplier's recommendations. Alkaline phosphatase removes 5'-phosphate groups from the ends of DNA fragments thereby preventing self-ligation. This is of particular relevance when self re-ligation of a DNA fragment could result in a replication-competent vector. The enzyme is active in most restriction enzyme buffers and was added as appropriate. After the digestion, the enzyme was inactivated by raising the temperature to 70° C. for 15 min.

Purification of PCR and restriction enzyme reaction products: Purification was carried out using the mini-elute PCR Purification kit (supplied by Qiagen), according to the manufacturer's instructions. Briefly, DNA samples were diluted in 5 volumes of binding buffer I (Qiagen) and loaded onto a mini-elute column within an Eppendorf centrifuge tube. The assembly was centrifuged in a bench-top microcentrifuge. The column was washed twice with buffer II (Qiagen): Following buffer application, the assembly was centrifuged and the flow-through was discarded. The column was dried by centrifugation in the absence of added buffer. DNA was eluted by adding elution buffer to the column and the eluate collected by centrifugation. Isolated DNA was quantified by UV spectroscopy and quality assessed by agarose gel electrophoresis.

Isolation of DNA fragments from agarose gel: Where appropriate (i.e., when multiple fragments were present), digested DNA samples were separated by gel electrophoresis and the desired fragment excised from the gel and recovered using the QIAEX II gel extraction kit (Qiagen), according to the manufacturer's instructions. Briefly, DNA bands were excised from the agarose gel and melted in an appropriate buffer at +55° C. QIAEX II resin was added and incubated for 5 min. QIAEX II resin was pelleted by a short centrifugation step (1 min, 14000 g, room temperature) and washed twice with 500 µl of wash buffer PE. The final pellet was dried in a hood and DNA was eluted with the appropriate volume of TE and temperature (depending on the size of the DNA).

Ligation of DNA fragments: Ligations were performed with the Quick Ligation Kit (New England Biolabs) according to the manufacturer's instructions. For each ligation, the vector DNA was mixed with approximately 3-fold molar excess of insert DNA such that the total amount of DNA was lower than 200 ng in 10 µl, with volume adjusted with water as appropriate. To this was added 10 µl 2× Quick Ligation Buffer and 1 µl Quick T4 DNA ligase and the ligation mix was incubated for 5-30 min at room temperature.

Transformation of DNA into bacteria: Samples of DNA were used to transform One Shot DH5α-TIR competent *E. coli* cells (Invitrogen, Breda, The Netherlands) using the heat-shock method according to the manufacturer's instructions. Briefly, 1-5 µl of DNA solution (typically 2 µl of DNA ligation mix) was added to an aliquot of transformation-competent bacterial cells and the mixture incubated on ice for 30 min. The cells were then heat-shocked by transferring to a waterbath at 42° C. for 30 sec followed by a further incubation on ice for 5 min. Cells were left to recover by incubation in a non-selective culture medium (SOC) for 1 hour with agitation at 37° C. and were subsequently spread onto agar plates containing appropriate selective agent (ampicillin at 50 µg/ml). Plates were incubated for 16-18 hours at +37° C. or until colonies of bacteria became evident.

Screening of bacterial colonies by PCR: Bacterial colonies were screened for the presence of vectors containing the desired sequences using the PCR colony screening technique. 20 µl of PCR reaction mix containing 0.5 volumes of Hot-StarTaq Master Mix (Qiagen), 4 µmol of the forward and reverse primers and completed with water was added to a PCR tube. A colony was lightly touched with a 20 µl pipet tip, once touched in 2 ml LB in a culture tube (for growing bacteria containing the corresponding plasmid) and resuspended in the 20 µl PCR mix. PCR was performed on a T-gradient Thermocycler 96 (Biometra) using a 35 cycle program of: +95° C. for 15 min, followed by 35 cycles of: +94° C. for 30 sec, anneal: 55° C. for 30 sec and extension: +72° C. for 2 min, followed by a final extension step of 10 min at 72° C. and subsequent storage at 4° C. The completed reactions were analyzed by agarose gel electrophoresis. See Table 2 for details of primer pairs used for colony PCR.

DNA sequencing: Plasmid DNA samples were send to AGOWA (Berlin, Germany) for sequence analysis. Sequences were analyzed using the Vector NTI software package (Informax, Frederick, Md., USA).

TABLE 2

| Name | Application | Length | Oligo Sequence | SEQ ID NOs |
|---|---|---|---|---|
| CD20P172S | CD20 mutagenesis | 36 | TGGGGAGTTTTTCTCAGAGGAATTC-GATGGTTCACAGTTGTA | SEQ ID NO: 31 |
| CD20N166D | CD20 mutagenesis | 39 | TGTAACAGTATTGGGTAGATGGG | SEQ ID NO: 32 |
| CD20N163D | CD20 mutagenesis | 36 | AATCATGGACATACTTAATATTA | SEQ ID NO: 33 |
| cd20exfor | CD20 construction | 41 | TATAGCCCGGGGCCGCCACCATGACAACACCCAGAAATTCA | SEQ ID NO: 34 |
| cd20exrev | CD20 construction | 38 | GCGTCTCATGTACATTAAGGAGAGCTGTCATTTTCTAT | SEQ ID NO: 35 |
| pee13.4seqrev2 | Colony PCR | 23 | TCGGACATCTCATGACTTTCTTT | SEQ ID NO: 36 |
| pConKseq1 | Colony PCR | 23 | GTAGTCTGAGCAGTACTCGTTGC | SEQ ID NO: 37 |
| cd20hsapmutf (AxP) | CD20 mutagenesis | 42 | TGGGGAGTTTTTCTCAGAGGAATTC-GATGGTTCACAGTTGTA | SEQ ID NO: 38 |
| cd20hsapmutf (AxP) | CD20 mutagenesis | 42 | TACAACTGTGAACCATCGAATTCCTCT-GAGAAAAACTCCCCA | SEQ ID NO: 39 |
| CD20seQ2 | CD20 sequencing | 23 | TGTAACAGTATTGGGTAGATGGG | SEQ ID NO: 40 |
| cd20seq1 | CD20 sequencing | 23 | AATCATGGACATACTTAATATTA | SEQ ID NO: 41 |

Mutagenesis: The mutagenesis was performed, using the QuikChange® XL Site-Directed Mutagenesis kit (Cat 200517-5, Lot 1120630, Stratagene Europe) according to the manufacturer's instructions.

Mutagenesis reactions were concentrated using ethanol precipitation and transformed into either oneshot DH5α-T1R competent *E. coli* cells or electroporated into ElectroTen-Blue Electroporation-Competent Cells. Colonies were checked by colony PCR and restriction digestion prior to transfection.

HEK293F cell transfection: HEK293F cells were obtained from Invitrogen and transfected according to the manufacturer's instructions, using 293fectin. The HEK293F cells were used for all the single mutant sequences.

Anti-CD20 Antibody binding: HEK293F cells and CHO cells were taken up in PBS in a concentration of $2 \times 10^6$/ml, and added to round bottom plates ($1 \times 10^5$/well). Then, 50 µl anti-CD20 monoclonal antibody was added, in serial dilutions of 10, 5, 2.5, or 0 µg per well (4° C., 30 min). After washing in FACS buffer (PBS supplemented with 0.1% BSA and 0.002% $NaN_3$), the cells were analyzed on a flow cytometer (Becton Dickinson, San Diego, Calif., USA), and 5,000 events per sample were acquired at high flow rate. Data in FIG. 11 have been corrected for protein to fluorescence ratio.

As can be seen from FIGS. 11A-E, both 2C6 IgG1,κ and the reference antibody rituximab bound efficiently to CHO cells expressing WT CD20. As expected, rituximab did not bind the AxP mutant and the P172S mutant (FIGS. 11B and C). 2C6 IgG1,κ in contrast did bind equally well to WT CD20, AxP mutant CD20 and P172S mutant CD20.

Figure 11A:
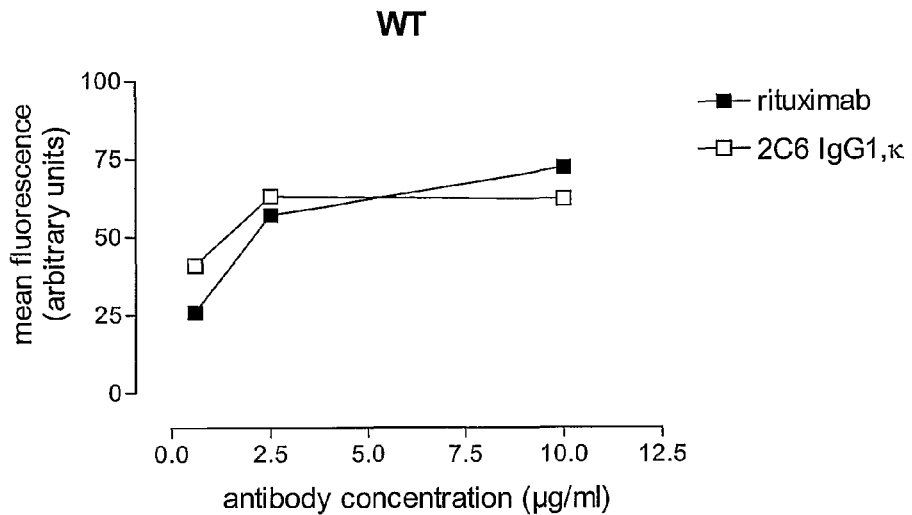
FIGS. 11A-11E show the binding of 2C6 IgG1,κ and in comparison herewith rituximab to wild-type (WT) CD20 (FIG. 11A), mutant CD20 (AxP A170SxP172S) (FIG. 11B), mutant CD20 (P172S) (FIG. 11C), mutant CD20 (N163D) (FIG. 11D), and mutant CD20 (N166D) (FIG. 11E).
Figure 11B:
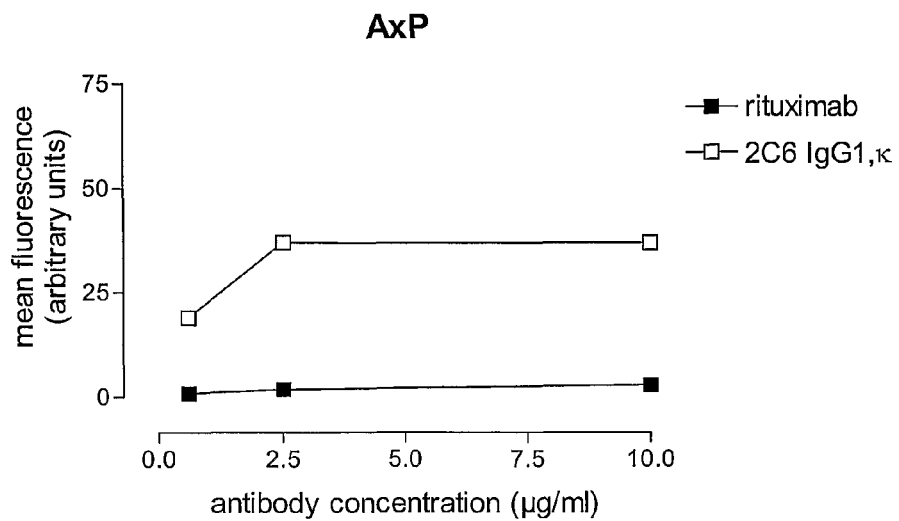
Figure 11C:
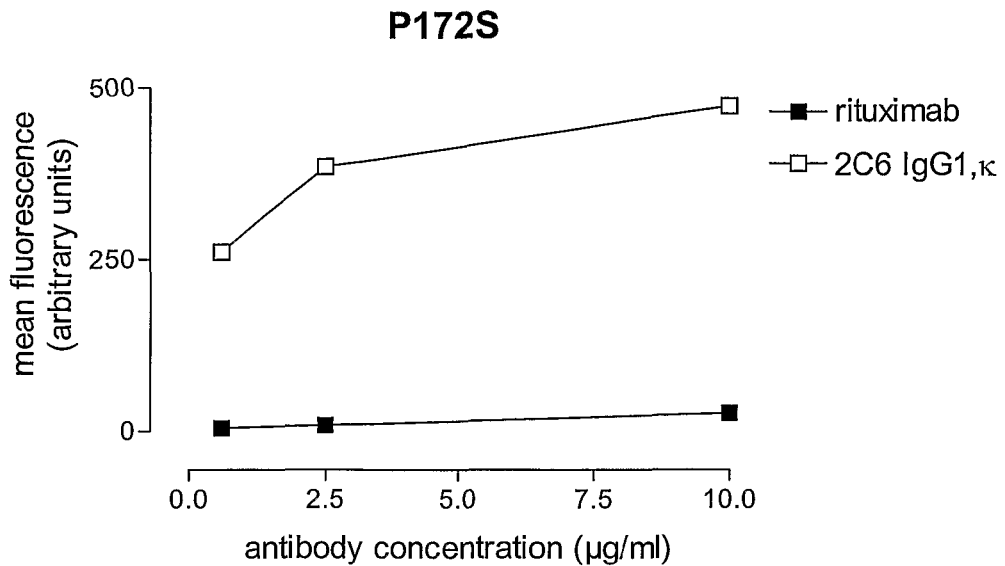
Figure 11D:
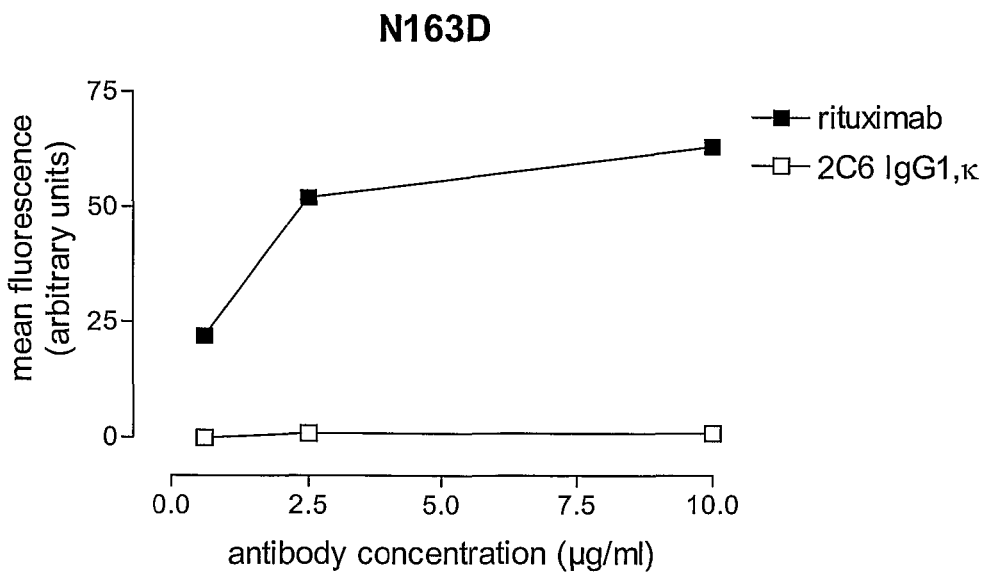

For the CD20 mutant wherein asparagine at position 163 has been replaced by aspartic acid (N163D), rituximab was able to bind to CD20N163D, whereas 2C6 IgG1,κ only showed very low binding, see FIG. 11D.

Figure 11E:
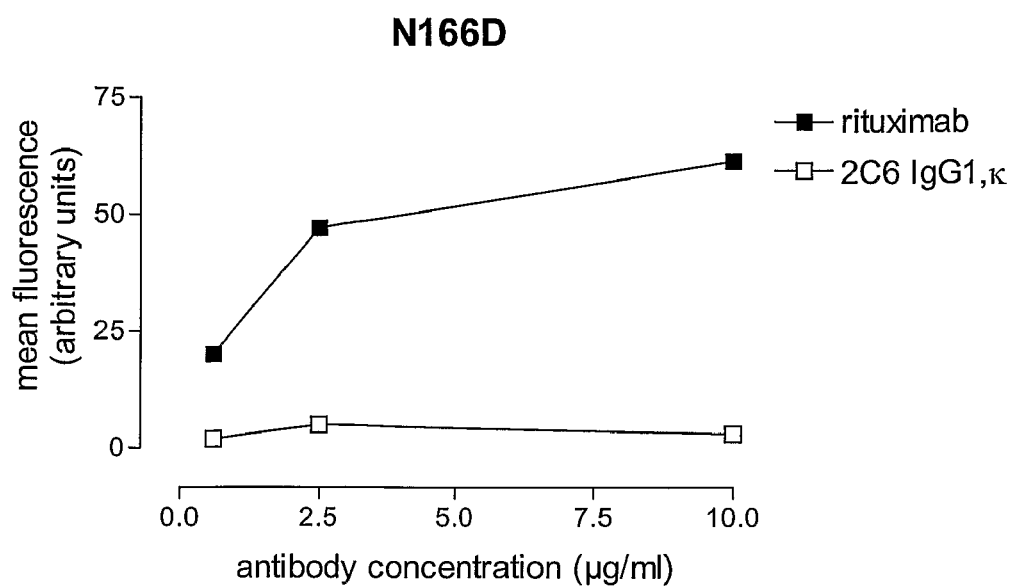

For the mutant wherein asparagine at position 166 has been replaced with aspartic acid (N166D) again 2C6 IgG1,κ showed very low binding, whereas rituximab was able to bind, see FIG. 11E.

These experiments indicate that 2C6 IgG1,κ and rituximab bind to different epitopes. Furthermore, this study indicates that binding of 2C6 IgG1,κ to human CD20 is sensitive to mutations at positions 163 and 166, but insensitive to mutations at positions 170 and 172. 2C6 IgG1,κ therefore belongs to a new class of anti-CD20 monoclonal antibodies recognizing a novel CD20 epitope.

Example 13

Immunoprecipitation and Western Blotting

Raji cells were lysed on ice for 15 min in lysis buffer containing protease inhibitors (1 μg/ml aprotinin, 1 μg/ml leupeptin, 1 mM NaMoO4, 1 mM NaVO4, 1 mM phenylmethylsulfonyl fluoride, and 1 mM EDTA) and either 1% Triton X-100 (Tx-100) or 1% digitonin. Lysates were incubated overnight with the antibodies (2C6 IgG1,κ, and the reference antibodies, rituximab, 2F2, and 7D8, and isotype control anti-KLH antibody) head over head (rotating), then protein-G Sepharose was added (approximately 30 μl from a 1:1 mixture of beads and lysis buffer), and the mixture was incubated for 1 to 2 hours at 4° C. The beads were washed with lysis buffer, and precipitated protein was eluted in non-reducing SDS sample buffer, separated by SDS-PAGE (4-15% Criterion gel, Biorad) and transferred to PVDF membranes (Biorad). The membranes were blocked with 1% topblock (Biorad) probed with anti-CD20 antibody (7D1, Serotec), whereupon the bound antibodies were detected with HRP-conjugated rabbit anti-mouse antibody (Amersham). Proteins were visualized using enhanced chemiluminescence (Pierce, Rockford, Ill.) recorded on a CCD Imager (Westburg).

Figure 12:
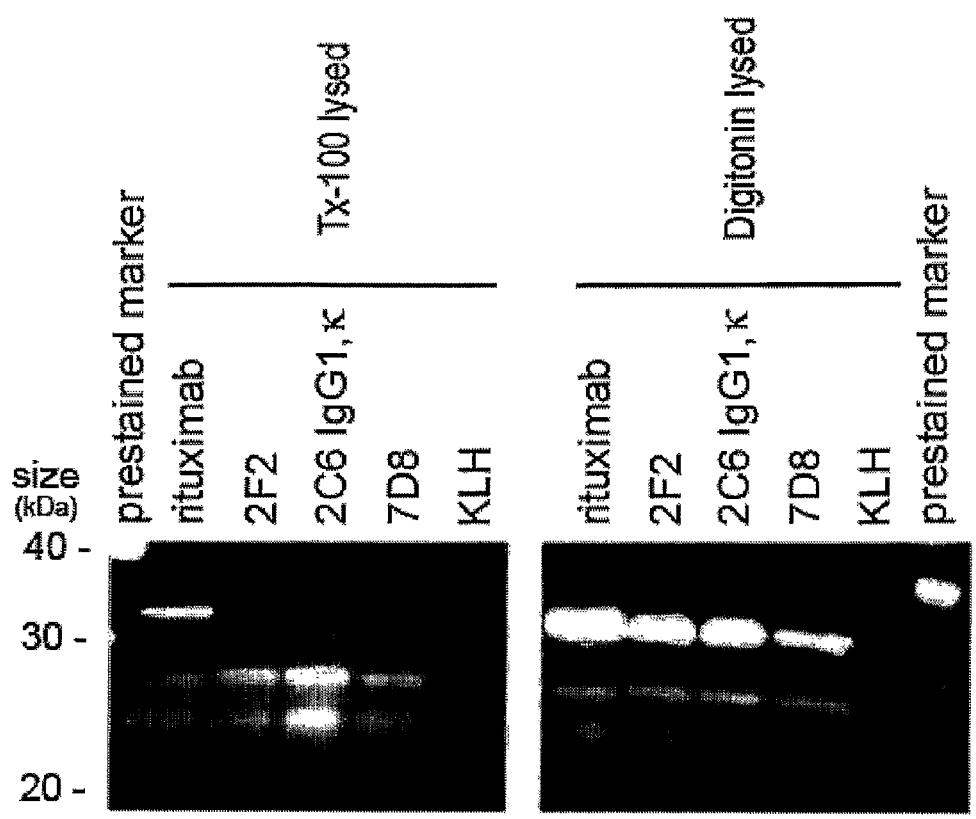
FIG. 12 shows binding of 2C6 IgG1,κ, and in comparison herewith rituximab, 2F2, 7D8 (a human monoclonal anti-CD20 antibody as further disclosed in WO 2004/035607) to Raji cells lysed with either 1% Triton-X (Tx-100) or digitonin in an immunoprecipitation assay.
Figure 13:
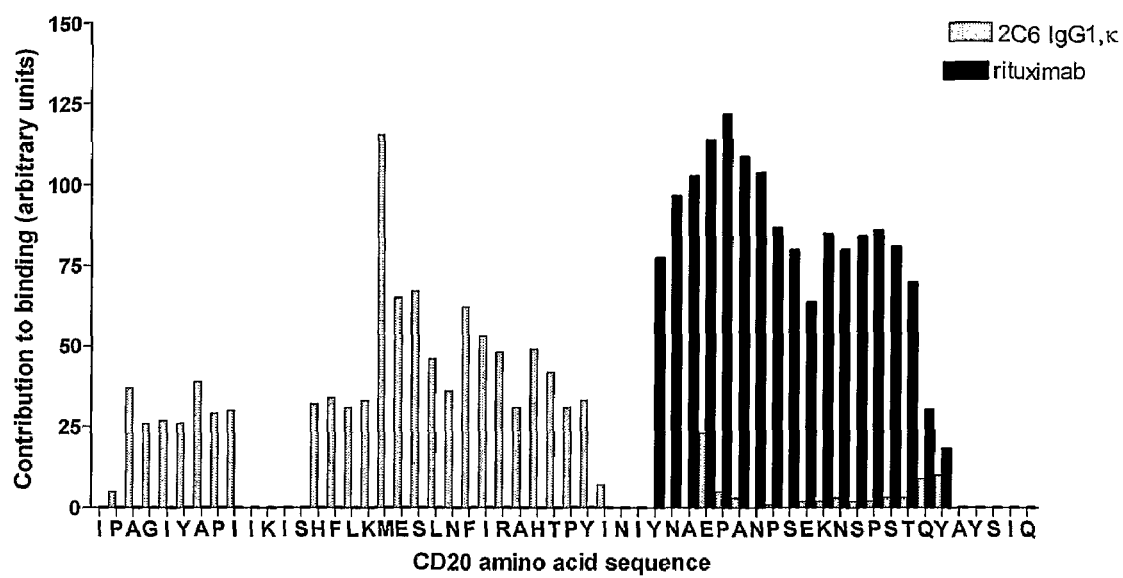
FIG. 13 shows the result of an epitope mapping for 2C6 IgG1,κ and in comparison herewith rituximab, using Pepscan method

FIG. 12 shows that rituximab efficiently precipitated CD20 from both Tx-100 and digitonin lysates, indicating that it binds to an epitope that remains intact under both conditions. In contrast, 2F2, 7D8 and 2C6 IgG1,κ only precipitated CD20 from digitonin lysate, suggesting that the epitopes for these human antibodies require the structural integrity of the multimeric form of CD20.

7D8 is a human monoclonal anti-CD20 antibody which is further disclosed in WO 2004/035607.

Example 14

Epitope Mapping Using Pepscan Method

Synthesis of peptides and pepscan screening: The overlapping mostly 15-mer synthetic peptides were synthesized and screened using credit-card format mini-PEPSCAN cards (455-well plate with 3 μl wells) as described by Slootstra et al., (1996) Structural aspects of antibody-antigen interaction revealed through small random peptide libraries. Mol-Divers. 1:87-96. The binding of antibodies (2C6 IgG1,κ and rituximab) to each peptide was tested in a PEPSCAN-based enzyme-linked immuno assay (ELISA). The 455-well creditcard-format polypropylene cards, containing the covalently linked peptides, were incubated with sample (for example 10 μg/ml antibody or serum diluted 1/1000 in a PBS solution containing 5% horse serum (vol/vol) and 5% ovalbumin (weight/vol) and 1% Tween 80 or in case of 2F2 in a PBS solution with 4% horse serum (vol/vol) and 1% Tween 80 (4° C., overnight). After washing the peptides were incubated with an anti-antibody peroxidase (dilution 1/1000, for example rabbit-anti-mouse peroxidase, Dako) (1 hour, 25° C.), and subsequently, after washing the peroxidase substrate 2,2'-azino-di-3-ethylbenzthiazoline sulfonate (ABTS) and 2 μl/ml 3% $H_2O_2$ were added. After 1 hour the color development was measured. The color development of the ELISA was quantified with a CCD-camera and an image processing system. The setup consists of a CCD-camera and a 55 mm lens (Sony CCD Video Camara XC-77RR, Nikon micro-nikkor 55 mm f/2.8 lens), a camara adaptor (Sony Camara adaptor DC-77RR) and the Image Processing Software package Optimas, version 6.5 (Media Cybernetics, Silver Spring, Md. 20910, U.S.A.). Optimas runs on a pentium computer system.

Synthesized Peptides:

Group-1: A Set of 505 Different 15-mer Single Domain Looped Peptides

All looped 15-mer peptides with spacing 4 to 13, such as for example CXXXXCXXXXXXXXX, XXXCXXXX-CXXXXXX or CXXXXXXXXXXXXXC, etc., of the peptides LMIPAGIYAPIAVTV (SEQ ID NO:42), KISHFLK-MESLNFIR (SEQ ID NO:43), KMESLNFIRAHTPYI (SEQ ID NO:44), MESLNFIRAHTPYIN (SEQ ID NO:45), YINIYNAEPANPSEK (SEQ ID NO:46), YNAEPANPSEKNSPS (SEQ ID NO:47), NAEPANPSEKNSPST (SEQ ID NO:48), EPANPSEKNSP-STQY (SEQ ID NO:49), PANPSEKNSPSTQYA (SEQ ID NO:50), NPSEKNSPSTQYAYS (SEQ ID NO:51), SEKNSPSTQYAYSIQ (SEQ ID NO:52) were synthesized.

Group-2: A Set of 400 Different Linear Two Domain 15-mer Peptides

All 400 combinations of XXXXXXXGXXXXXXX with the following 20 sequences NFIRAHT (SEQ ID NO:53), FIRAHTP (SEQ ID NO:54), IRAHTPY (SEQ ID NO:55), RAHTPYI (SEQ ID NO:56), HFLKMES (SEQ ID NO:57), FLKMESL (SEQ ID NO:58), LKMESLN (SEQ ID NO:59), KMESLNF (SEQ ID NO:60), MESLNFI (SEP ID NO:61), EPANPSE (SEQ ID NO:62), PANPSEK (SEQ ID NO:63), ANPSEKN (SEQ ID NO:64), NPSEKNS (SEQ ID NO:65), PSEKNSP (SEQ ID NO:66), SEKNSPS (SEQ ID NO:67), EKNSPST (SEQ ID NO:68), KNSPSTQ (SEQ ID NO:69), NSPSTQY (SEQ ID NO:70), PAGIAYP (SEQ ID NO:71), AGIYAPI (SEQ ID NO:72) were synthesized.

Method for epitope representation: To analyse the Pepscan data and obtain a representation of the contribution of each of the amino acids in the CD20 sequence, a novel epitope analysis method was deviced taking into account all the data obtained with the 905 peptides and allowing for scoring of amino acid contributions to conformational epitopes. In each peptide all possible tripeptide motifs, i.e. the smallest unique units, were determined. For example if the peptide was ABCDE all tripeptide motifs include ABC, BCD, CDE, ABXD, ABXXE, AXCD, AXXDE, AXCXE. Then, each of these tripeptide motifs was awarded the ELISA value of the whole peptide. This procedure was followed for all tripeptide motifs in all 905 peptides. Next, to be able to rank the tripeptide motifs from strong to poor binding, a relative signal was calculated by dividing the ELISA value obtained for each individual motif by the average ELISA value from all 905 tested 15-mers, and sorted for decreasing value.

For each of the antibodies tested all tripeptide motifs that scored above 2.5 (approximately the top 500 motifs) were selected. This means that the ELISA values of peptides containing these motifs were at least 2.5 times the average ELISA value obtained with all 905 peptides. With 2C6 IgG1,κ the scores were lower than 2.50 and the cutt-off was therefore chosen at 1.50. Finally, these data were deconvoluted into single amino acid contributions represented on the linear CD20 sequence by a scoring system. By walking along the linear CD20 sequence and by using the unique tripeptide units as a reference point, one point was awarded each time a CD20 amino acid was present in this set of high scoring peptides The graph shows the total points obtained for each of the single amino acids and represented for each of the antibodies tested. For example, the highest scoring residue with rituximab is the P172 (about 125 of the 500 high scoring tripeptide motifs contain this P172).

The results are shown in FIG. 14. FIG. 14 shows that in contrast to rituximab, 2C6 IgG1,κ binds to peptides N-terminal from A170/P172, and also to peptides derived from the smaller of the two extracellular CD20 loops (AGIYAPI: SEQ ID NO:72). Very weak binding of 2C6 IgG1,κ was observed C-terminal of A170/P172.

EQUIVALENTS

Those skilled in the art will recognize or be able to ascertain, using no more than routine experimentation, many equivalents of the specific embodiments of the invention described herein. Such equivalents are intended to be encompassed by the following claims. Any combination of the embodiments disclosed in the dependent claims are also contemplated to be within the scope of the invention.

INCORPORATION BY REFERENCE

All patents, pending patent applications and other publications cited herein are hereby incorporated by reference in their entirety.

The invention claimed is:

1. A human monoclonal antibody which specifically binds to human CD20, and which comprises a heavy chain variable region and a light chain variable region, each of the heavy chain variable region and light chain variable region comprising three complementarity determining regions (CDRs), wherein the heavy chain variable region contains the $V_H$ CDR1 of SEQ ID NO: 8, the $V_H$ CDR2 of SEQ ID NO: 9 and the $V_H$ CDR3 of SEQ ID NO: 10, and wherein the light chain variable region contains the $V_L$ CDR1 of SEQ ID NO: 11, the $V_L$ CDR2 of SEQ ID NO: 12 and the $V_L$ CDR3 of SEQ ID NO: 13.

2. A human monoclonal antibody which specifically binds to human CD20, and which comprises a heavy chain variable region and a light chain variable region, each of the heavy chain variable region and light chain variable region comprising three complementarity determining regions (CDRs), wherein the heavy chain variable region contains the $V_H$ CDR1 of SEQ ID NO: 8, the $V_H$ CDR2 of SEQ ID NO: 9 and the $V_H$ CDR3 of SEQ ID NO: 10, and wherein the light chain variable region contains the $V_L$ CDR1 of SEQ ID NO: 14, the $V_L$ CDR2 of SEQ ID NO: 15 and the $V_L$ CDR3 of SEQ ID NO: 16.

3. A human monoclonal antibody which specifically binds to human CD20, and which comprises a heavy chain variable region and a light chain variable region, each of the heavy chain variable region and light chain variable region comprising three complementarity determining regions (CDRs), wherein the heavy chain variable region contains the $V_H$ CDR1 of SEQ ID NO: 8, the $V_H$ CDR2 of SEQ ID NO: 9 and the $V_H$ CDR3 of SEQ ID NO: 10, and wherein the light chain variable region contains the $V_L$ CDR1 of SEQ ID NO: 17, the $V_L$ CDR2 of SEQ ID NO: 18 and the $V_L$ CDR3 of SEQ ID NO: 19.

4. The antibody of any one of claims 1, 2, and 3, characterized in that it is an IgG1 or IgM antibody.

5. The antibody of claim 4, characterized in that it is an IgG1,κ or IgM,κ antibody.

6. An isolated antibody which is encoded by human heavy chain nucleic acids and human kappa light chain nucleic acids comprising variable heavy chain nucleotide sequence SEQ ID NO: 1, and variable light chain nucleotide sequence SEQ ID NO: 3 or SEQ ID NO: 6, wherein each of the heavy chain and the light chain has a variable region comprising three complementarity determining regions (CDRs) and the heavy chain variable region contains $V_H$ CDR3 of SEQ ID NO: 10.

7. The antibody of any one of claims 1, 2 and 3, which is an antigen binding antibody fragment or a single chain antibody.

8. A hybridoma which produces a human monoclonal antibody against CD20 encoded by human heavy chain and human light chain nucleic acids comprising nucleotide sequences in their variable heavy chain region as set forth in SEQ ID NO: 1, and nucleotide sequences in their variable light chain region as set forth in SEQ ID NO: 3 or SEQ ID NO: 6, respectively.

9. A hybridoma which produces a human monoclonal antibody against CD20 having human heavy chain and light chain variable regions which comprise the human heavy chain variable amino acid sequence as set forth in SEQ ID NO: 2, and the human light chain variable amino sequence as set forth in SEQ ID NO: 4, SEQ ID NO: 5, or SEQ ID NO: 7, respectively.

10. A pharmaceutical composition comprising a human monoclonal antibody of any one of claims 1, 2 and 3 and a pharmaceutically acceptable carrier.

11. The pharmaceutical composition according to claim 10, further comprising one or more additional therapeutic agents.

12. The antibody according to any one of claims 1, 5 and 3, further comprising a chelator linker for attaching a radioisotope.

13. An immunoconjugate comprising an antibody according to any one of claims 1, 2 and 3 linked to a cytotoxic agent, a radioisotope, or a drug.

14. The immunoconjugate of claim 13, wherein the antibody is a monomeric IgM antibody linked to a cytotoxic agent, a radioisotope, or a drug.

15. A bispecific molecule comprising an antibody according to any one of claims 1, 2 and 3 and a binding specificity for a human effector cell.

16. A bispecific molecule comprising an antibody according to any one of claims 1, 2 and 3 and a binding specificity for a human Fc receptor or a T cell receptor.

17. A method of treating a disease or disorder involving cells expressing CD20, comprising administering to a subject an effective amount of a pharmaceutical composition comprising a human monoclonal antibody that binds to human CD20, wherein the antibody comprises a heavy chain variable region and a light chain variable region, each of the heavy chain variable region and light chain variable region comprising three complementarity determining regions (CDRs), wherein the heavy chain variable region contains the $V_H$ CDR1 of SEQ ID NO: 8, the $V_H$ CDR2 of SEQ ID NO: 9 and the $V_H$ CDR3 of SEQ ID NO: 10, and wherein the light chain variable region contains:

(a) the $V_L$ CDR1 of SEQ ID NO: 11, the $V_L$ CDR2 of SEQ ID NO: 12 and the $V_L$ CDR3 of SEQ ID NO: 13;

(b) the $V_L$ CDR1 of SEQ ID NO: 14, the $V_L$ CDR2 of SEQ ID NO: 15 and the $V_L$ CDR3 of SEQ ID NO: 16; or (c) the $V_L$ CDR1 of SEQ ID NO: 17, the $V_L$ CDR2 of SEQ ID NO: 18 and the $V_L$ CDR3 of SEQ ID NO: 19.

18. The method of claim 17, wherein the disease or disorder is a B cell lymphoma.

19. The method of claim 17, wherein the disease or disorder is B cell non-Hodgkin's lymphoma (NHL).

20. The method of claim 17, wherein the disease or disorder is selected from the group consisting of precursor B cell lymphoblastic leukemia/lymphoma and mature B cell neoplasms.

21. The method of claim 17, wherein the disease or disorder is follicular lymphoma (FL).

22. The method of claim 17, wherein the disease or disorder is B cell chronic lymhocytic leukemia (CLL)/small lymphocytic lymphoma (SLL).

23. The method of claim 17, wherein the disease or disorder is selected from the group consisting of psoriasis, psoriatic arthritis, dermatitis, systemic sclerosis, inflammatory bowel disease (IBD), Crohn's disease, ulcerative colitis, respiratory distress syndrome, meningitis, encephalitis, uveitis, glomerulonephritis, eczema, asthma, atherosclerosis, leukocyte adhesion deficiency, multiple sclerosis, Raynaud's syndrome, Sjogren's syndrome, juvenile onset diabetes, Reiter's disease, Behget's disease, immune complex nephritis, IgA nephropathy, IgM polyneuropathies, immune-mediated thrombocytopenias, hemolytic anemia, myasthenia gravis, lupus nephritis, systemic lupus erythematosus, rheumatoid arthritis (RA), atopic dermatitis, pemphigus (including pempigus vulgaris), Graves' disease, Hashimoto's thyroiditis, Wegener's granulomatosis, Omenn's syndrome, chronic renal failure, acute infectious mononucleosis, herpes virus associated diseases, and as well as diseases and disorders caused by or mediated by infection of B-cells with virus.

24. The method of claim 17, wherein the disease or disorder is rheumatoid arthritis (RA).

25. The method of claim 17, wherein the disease or disorder is selected from inflammatory bowel disease (IBD), ulcerative colitis, Crohn's disease, juvenile onset diabetes, multiple sclerosis, immune-mediated thrombocytopenias, hemolytic anemia, myasthenia gravis, systemic sclerosis, and pemphigus vulgaris.

26. The method of claim 17, wherein the disease or disorder is selected from inflammatory bowel disease (IBD), ulcerative colitis, Crohn's disease, and multiple sclerosis.

27. The method of claim 17, comprising administering one or more further therapeutic agents to the subject.

28. The method of claim 27, wherein the one or more further therapeutic agents are selected from chemotherapeutic agents, anti-inflammatory drugs, disease modifying anti-rheumatic drugs (DMARDs), and immunosuppressive agents.

29. The method of claim 27, wherein the one or more further therapeutic agents are selected from antimetabolites, alkylating agents, anthracyclines, antibiotics, and anti-mitotic agents.

30. The method of claim 27, wherein the therapeutic agent is selected from the group consisting of doxorubicin, cisplatin, bleomycin, carmustine, chlorambucil, and cyclophosphamide.

31. The method of claim 27, wherein the therapeutic agent is an immunological modulating agent.

32. The method of claim 27, wherein the therapeutic agent is selected from the group consisting of anti-CD25 antibodies, anti-CD19 antibodies, anti-CD21 antibodies, anti-CD22 antibodies, anti-CD37 antibodies, anti-CD38 antibodies, anti-IL6R antibodies, anti-IL8 antibodies, anti-IL15 antibodies, anti-IL15R antibodies, anti-CD4 antibodies, anti-CDIIa antibodies, anti-alpha-4/beta-1 integrin (VLA4) antibodies, CTLA4-Ig, and anti-C3b(i) antibodies.

33. A kit for detecting the presence of CD20 antigen, or a cell expressing CD20, in a sample comprising the antibody of any one of claims 1, 5 and 3.

34. An anti-idiotypic antibody binding to an antibody of any one of claims 1, 5 and 3.

35. A method of treating a disease or disorder involving cells expressing CD20, comprising administering to a subject an immunoconjugate according to claim 13 in an amount effective to treat the disease or disorder.

36. A method of treating or a disease or disorder involving cells expressing CD20, comprising administering to a subject a bispecific antibody according to claim 15 in an amount effective to treat the disease or disorder.

37. The bispecific molecule of claim 16, wherein the T cell receptor is CD3.

38. The method of claim 20, wherein the disease or disorder is mature B cell neoplasm selected from B cell chronic lymhocytic leukemia (CLL)/small lymphocytic lymphoma (SLL), B cell prolymphocytic leukemia, lymphoplasmacytic lymphoma, mantle cell lymphoma (MCL), follicular lymphoma (FL), cutaneous follicle center lymphoma, marginal zone B cell lymphoma (MALT type, nodal and splenic type), hairy cell leukemia, diffuse large B cell lymphoma, Burkitt's lymphoma, plasmacytoma, plasma cell myeloma, post-transplant lymphoproliferative disorder, Waldenstrom's macroglobulinemia, anaplastic large-cell lymphoma (ALCL), lymphomatoid granulomatosis, primary effusion lymphoma, intravascular large B cell lymphoma, mediastinal large B cell lymphoma, heavy chain disease, or lymphoma induced by therapy with an immunosuppressive agent.

39. The method of claim 38, wherein the lymphoma induced by therapy with an immunosuppressive agent is cyclosporine-induced lymphoma or methotrexate-induced lymphoma.

40. The method of claim 38, wherein the heavy chain disease is $\gamma$ disease, $\mu$ disease, or $\alpha$ disease.

41. The method of claim 23, wherein the disease or disorder is an immune-mediated thrombocytopenia selected from acute idiopathic thrombocytopenic purpura or chronic idiopathic thrombocytopenic purpura.

42. The method of claim 23, wherein the disease or disorder is a disease and disorder caused by or mediated by infection of B-cells with virus, wherein the virus is Epstein Barr virus (EBV).

43. The method of claim 25, wherein the disease or disorder is an immune-mediated thrombocytopenias selected from acute idiopathic thrombocytopenic purpura or chronic idiopathic thrombocytopenic purpura.

44. The method of claim 29, wherein the one or more further therapeutic agents are antimetabolites selected from methotrexate, 6-mercaptopurine, 6-thioguanine, cytarabine, fludarabin, 5-fluorouracil, decarbazine, hydroxyurea, azathiprin, gemcitabin or cladribin.

45. The method of claim 29, wherein the one or more further therapeutic agents are alkylating agents selected from mechlorethamine, thioepa, chlorambucil, melphalan, carmustine (BSNU), lomustine (CCNU), cyclophosphamide, busulfan, dibromomannitol, streptozotocin, mitomycin C, or cis-dichlorodiamine platinum (II) (DDP) cisplatin.

46. The method of claim 29, wherein the one or more further therapeutic agents are anthracyclines selected from daunorubicin (formerly daunomycin) or doxorubicin.

47. The method of claim 29, wherein the one or more further therapeutic agents are antibiotics selected from dactinomycin (formerly actinomycin), bleomycin, mithramycin, or anthramycin (AMC).

48. The method of claim 29, wherein the one or more further therapeutic agents are anti-mitotic agents selected from vincristine, vin-blastine, docetaxel, paclitaxel or vinorelbin.

49. The method of claim 31, wherein the immunological modulating agent is a cytokine or a chemokine.

* * * * *

UNITED STATES PATENT AND TRADEMARK OFFICE
CERTIFICATE OF CORRECTION

| | | |
|---|---|---|
| PATENT NO. | : 7,850,962 B2 | |
| APPLICATION NO. | : 11/578818 | |
| DATED | : December 14, 2010 | |
| INVENTOR(S) | : Jessica Teeling et al. | |

It is certified that error appears in the above-identified patent and that said Letters Patent is hereby corrected as shown below:

Column 87, Claim 12, line 51, delete "5" and insert --2--.

Column 88, Claim 23, line 39, delete "Behget's" and insert --Behçet's--.

Column 89, Claim 33, line 21, delete "5" and insert --2--.

Column 89, Claim 34, line 23, delete "5" and insert --2--.

Column 89, Claim 36, line 28, after the word "treating" delete "or".

Signed and Sealed this
Fifteenth Day of March, 2011

David J. Kappos
*Director of the United States Patent and Trademark Office*

SEQUENCE LISTING

```
<160> NUMBER OF SEQ ID NOS: 79

<210> SEQ ID NO 1
<211> LENGTH: 369
<212> TYPE: DNA
<213> ORGANISM: Homo sapiens

<400> SEQUENCE: 1
gcagtgcagc tggtggagtc tgggggaggc ttagtacagc ctggcaggtc cctgagactc      60
tcctgtgcag cctctggatt cacctttggt gattatacca tgcactgggt ccggcaagct     120
ccagggaagg gcctggagtg ggtctcaggt attagttgga atagtggtag cataggctat     180
gcggactctg tgaagggccg attcaccatc tccagagaca acgccaagaa ctccctgtat     240
ctgcaaatga acagtctgag agctgaggac acggccttgt attactgtac aaaagataat     300
caatatggtt cggggagtac ctacggtttg ggcgtctggg gccaagggac actagtcaca     360
gtctcctca                                                              369

<210> SEQ ID NO 2
<211> LENGTH: 123
<212> TYPE: PRT
<213> ORGANISM: Homo sapiens

<400> SEQUENCE: 2

Ala Val Gln Leu Val Glu Ser Gly Gly Gly Leu Val Gln Pro Gly Arg
 1               5                   10                  15

Ser Leu Arg Leu Ser Cys Ala Ala Ser Gly Phe Thr Phe Gly Asp Tyr
             20                  25                  30

Thr Met His Trp Val Arg Gln Ala Pro Gly Lys Gly Leu Glu Trp Val
         35                  40                  45

Ser Gly Ile Ser Trp Asn Ser Gly Ser Ile Gly Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Thr Lys Asp Asn Gln Tyr Gly Ser Gly Ser Thr Tyr Gly Leu Gly Val
            100                 105                 110

Trp Gly Gln Gly Thr Leu Val Thr Val Ser Ser
        115                 120
```

<210> SEQ ID NO 3
<211> LENGTH: 321
<212> TYPE: DNA
<213> ORGANISM: Homo sapiens

<400> SEQUENCE: 3

```
gaaattgtgt tgacacagtc tccagccacc ctgtctttgt ctccagggga aagagccacc      60
ctctcctgca gggccagtca gagtgttagc agctacttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cagtttatta ctgtcagcag cgtagcaact ggcctctcac tttcggcgga     300
gggaccaagg tggagatcaa a                                              321
```

<210> SEQ ID NO 4
<211> LENGTH: 107
<212> TYPE: PRT
<213> ORGANISM: Homo sapiens

<400> SEQUENCE: 4

```
Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Tyr
             20                  25                  30

Leu Ala Trp Tyr Gln Gln Lys Pro Gly Gln Ala Pro Arg Leu Leu Ile
         35                  40                  45

Tyr Asp Ala Ser Asn Arg Ala Thr Gly Ile Pro Ala Arg Phe Ser Gly
     50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Leu
                 85                  90                  95

Thr Phe Gly Gly Gly Thr Lys Val Glu Ile Lys
            100                 105
```

<210> SEQ ID NO 5
<211> LENGTH: 106
<212> TYPE: PRT
<213> ORGANISM: Homo sapiens

<400> SEQUENCE: 5

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Ser Ser Trp
             20                  25                  30

Leu Ala Trp Tyr Gln Gln Lys Pro Glu Lys Ala Pro Lys Ser Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Val Phe Thr
                 85                  90                  95

Phe Gly Pro Gly Thr Lys Val Asp Ile Lys
            100                 105
```

<210> SEQ ID NO 6
<211> LENGTH: 321
<212> TYPE: DNA
<213> ORGANISM: Homo sapiens

<400> SEQUENCE: 6

```
gaaattgtgt tgacacagtc tccagccacc ctgtctttgt ctccagggga aagagccacc    60
ctctcctgca gggccagtca gagtgttagc agctacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg cagtttatta ctgtcagcag cgtagcgact ggccgctcac tttcggcgga   300
gggaccaagg tggagatcaa a                                             321
```

<210> SEQ ID NO 7
<211> LENGTH: 107
<212> TYPE: PRT
<213> ORGANISM: Homo sapiens

<400> SEQUENCE: 7

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asp Trp Pro Leu
                85                  90                  95

Thr Phe Gly Gly Gly Thr Lys Val Glu Ile Lys
            100                 105

<210> SEQ ID NO 8
<211> LENGTH: 5
<212> TYPE: PRT
<213> ORGANISM: Homo sapiens

<400> SEQUENCE: 8

Asp Tyr Thr Met His
1               5

<210> SEQ ID NO 9
<211> LENGTH: 17
<212> TYPE: PRT
<213> ORGANISM: Homo sapiens

<400> SEQUENCE: 9

Gly Ile Ser Trp Asn Ser Gly Ser Ile Gly Tyr Ala Asp Ser Val Lys
1               5                   10                  15

Gly

<210> SEQ ID NO 10
<211> LENGTH: 14
<212> TYPE: PRT
<213> ORGANISM: Homo sapiens

<400> SEQUENCE: 10

```
Asp Asn Gln Tyr Gly Ser Gly Ser Thr Tyr Gly Leu Gly Val
1               5                   10
```

<210> SEQ ID NO 11
<211> LENGTH: 11
<212> TYPE: PRT
<213> ORGANISM: Homo sapiens

<400> SEQUENCE: 11

```
Arg Ala Ser Gln Ser Val Ser Ser Tyr Leu Ala
1               5                   10
```

<210> SEQ ID NO 12
<211> LENGTH: 7
<212> TYPE: PRT
<213> ORGANISM: Homo sapiens

<400> SEQUENCE: 12

```
Asp Ala Ser Asn Arg Ala Thr
1               5
```

<210> SEQ ID NO 13
<211> LENGTH: 9
<212> TYPE: PRT
<213> ORGANISM: Homo sapiens

<400> SEQUENCE: 13

```
Gln Gln Arg Ser Asn Trp Pro Leu Thr
1               5
```

<210> SEQ ID NO 14
<211> LENGTH: 11
<212> TYPE: PRT
<213> ORGANISM: Homo sapiens

<400> SEQUENCE: 14

```
Arg Ala Ser Gln Gly Ile Ser Ser Trp Leu Ala
1               5                   10
```

<210> SEQ ID NO 15
<211> LENGTH: 7
<212> TYPE: PRT
<213> ORGANISM: Homo sapiens

<400> SEQUENCE: 15

```
Ala Ala Ser Ser Leu Gln Ser
1               5
```

<210> SEQ ID NO 16
<211> LENGTH: 8
<212> TYPE: PRT
<213> ORGANISM: Homo sapiens

<400> SEQUENCE: 16

```
Gln Gln Tyr Asn Ser Val Phe Thr
1               5
```

<210> SEQ ID NO 17
<211> LENGTH: 11
<212> TYPE: PRT
<213> ORGANISM: Homo sapiens

<400> SEQUENCE: 17

Arg Ala Ser Gln Ser Val Ser Ser Tyr Leu Ala

<210> SEQ ID NO 18
<211> LENGTH: 7
<212> TYPE: PRT
<213> ORGANISM: Homo sapiens

<400> SEQUENCE: 18

Asp Ala Ser Asn Arg Ala Thr
1               5

<210> SEQ ID NO 19
<211> LENGTH: 9
<212> TYPE: PRT
<213> ORGANISM: Homo sapiens

<400> SEQUENCE: 19

Gln Gln Arg Ser Asp Trp Pro Leu Thr
1               5

<210> SEQ ID NO 20
<211> LENGTH: 35
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (15)...(15)
<223> OTHER INFORMATION: n is c or t
<220> FEATURE:
<221> NAME/KEY: misc_feature
<222> LOCATION: (25)...(25)
<223> OTHER INFORMATION: n is c or g
<220> FEATURE:
<221> NAME/KEY: misc_feature
<222> LOCATION: (30)...(30)
<223> OTHER INFORMATION: n is c or g
<220> FEATURE:
<221> NAME/KEY: misc_feature
<222> LOCATION: (34)...(34)
<223> OTHER INFORMATION: n is c or t

<400> SEQUENCE: 20
gggaattcat ggagnttggg ctganctggn tttnt                      35

<210> SEQ ID NO 21
<211> LENGTH: 29
<212> TYPE: DNA
<213> ORGANISM: Artificial Sequence
<220> FEATURE:
<223> OTHER INFORMATION: primer

<400> SEQUENCE: 21
cccaagctta gacgaggggg aaaagggtt                             29

<210> SEQ ID NO 22
<211> LENGTH: 35
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (18)...(18)
<223> OTHER INFORMATION: n is a or g
<220> FEATURE:
<221> NAME/KEY: misc_feature
<222> LOCATION: (19)...(19)
<223> OTHER INFORMATION: n is a or g

```
<220> FEATURE:
<221> NAME/KEY: misc_feature
<222> LOCATION: (20)...(20)
<223> OTHER INFORMATION: n is a or g
<220> FEATURE:
<221> NAME/KEY: misc_feature
<222> LOCATION: (21)...(21)
<223> OTHER INFORMATION: n is a or t or g
<220> FEATURE:
<221> NAME/KEY: misc_feature
<222> LOCATION: (22)...(22)
<223> OTHER INFORMATION: n is c or t
<220> FEATURE:
<221> NAME/KEY: misc_feature
<222> LOCATION: (25)...(25)
<223> OTHER INFORMATION: n is a or t or c
<220> FEATURE:
<221> NAME/KEY: misc_feature
<222> LOCATION: (26)...(26)
<223> OTHER INFORMATION: n is a or c or g
<220> FEATURE:
<221> NAME/KEY: misc_feature
<222> LOCATION: (28)...(28)
<223> OTHER INFORMATION: n is c or t
<220> FEATURE:
<221> NAME/KEY: misc_feature
<222> LOCATION: (29)...(29)
<223> OTHER INFORMATION: n is t or g
<220> FEATURE:
<221> NAME/KEY: misc_feature
<222> LOCATION: (32)...(32)
<223> OTHER INFORMATION: n is c or g

<400> SEQUENCE: 22
gggaattcat ggacatgnnn nnccnngnnc anctt                                  35

<210> SEQ ID NO 23
<211> LENGTH: 28
<212> TYPE: DNA
<213> ORGANISM: Artificial Sequence
<220> FEATURE:
<223> OTHER INFORMATION: primer

<400> SEQUENCE: 23
cccaagcttc atcagatggc gggaagat                                          28

<210> SEQ ID NO 24
<211> LENGTH: 37
<212> TYPE: DNA
<213> ORGANISM: Artificial Sequence
<220> FEATURE:
<223> OTHER INFORMATION: primer

<400> SEQUENCE: 24
ataagcttca ggactcacca tggagtttgg gctgagc                                37

<210> SEQ ID NO 25
<211> LENGTH: 24
<212> TYPE: DNA
<213> ORGANISM: Artificial Sequence
<220> FEATURE:
<223> OTHER INFORMATION: primer

<400> SEQUENCE: 25
ggtgactagt gtcccttggc ccca                                              24

<210> SEQ ID NO 26
<211> LENGTH: 37
<212> TYPE: DNA
<213> ORGANISM: Artificial Sequence
<220> FEATURE:
```

```
<223> OTHER INFORMATION: primer

<400> SEQUENCE: 26
ataagcttca ggactcacca tggacatgga ggccccg                                    37

<210> SEQ ID NO 27
<211> LENGTH: 24
<212> TYPE: DNA
<213> ORGANISM: Artificial Sequence
<220> FEATURE:
<223> OTHER INFORMATION: primer

<400> SEQUENCE: 27
caccgtacgt ttgatctcca cctt                                                  24

<210> SEQ ID NO 28
<211> LENGTH: 144
<212> TYPE: PRT
<213> ORGANISM: Homo sapiens

<400> SEQUENCE: 28
```

Met Glu Leu Gly Leu Ser Trp Val Phe Leu Val Ala Ile Leu Lys Gly
 1               5                  10                  15

Val Gln Cys Glu Val Gln Leu Val Gln Ser Gly Gly Gly Leu Val His
                20                  25                  30

Pro Gly Gly Ser Leu Arg Leu Ser Cys Thr Gly Ser Gly Phe Thr Phe
            35                  40                  45

Ser Tyr His Ala Met His Trp Val Arg Gln Ala Pro Gly Lys Gly Leu
        50                  55                  60

Glu Trp Val Ser Ile Ile Gly Thr Gly Gly Val Thr Tyr Tyr Ala Asp
65                  70                  75                  80

Ser Val Lys Gly Arg Phe Thr Ile Ser Arg Asp Asn Val Lys Asn Ser
                85                  90                  95

Leu Tyr Leu Gln Met Asn Ser Leu Arg Ala Glu Asp Met Ala Val Tyr
            100                 105                 110

Tyr Cys Ala Arg Asp Tyr Tyr Gly Ala Gly Ser Phe Tyr Asp Gly Leu
        115                 120                 125

Tyr Gly Met Asp Val Trp Gly Gln Gly Thr Thr Val Thr Val Ser Ser
    130                 135                 140

```
<210> SEQ ID NO 29
<211> LENGTH: 140
<212> TYPE: PRT
<213> ORGANISM: Homo sapiens

<400> SEQUENCE: 29
```

Met Glu Leu Gly Leu Ser Trp Ile Phe Leu Leu Ala Ile Leu Lys Gly
 1               5                  10                  15

Val Gln Cys Glu Val Gln Leu Val Glu Ser Gly Gly Gly Leu Val Gln
                20                  25                  30

Pro Gly Arg Ser Leu Arg Leu Ser Cys Ala Ala Ser Gly Phe Thr Phe
            35                  40                  45

Asn Asp Tyr Ala Met His Trp Val Arg Gln Ala Pro Gly Lys Gly Leu
        50                  55                  60

Glu Trp Val Ser Thr Ile Ser Trp Asn Ser Gly Ser Ile Gly Tyr Ala
65                  70                  75                  80

Asp Ser Val Lys Gly Arg Phe Thr Ile Ser Arg Asp Asn Ala Lys Lys
                85                  90                  95

```
Ser Leu Tyr Leu Gln Met Asn Ser Leu Arg Ala Glu Asp Thr Ala Leu
            100                 105                 110

Tyr Tyr Cys Ala Lys Asp Ile Gln Tyr Gly Asn Tyr Tyr Tyr Gly Met
        115                 120                 125

Asp Val Trp Gly Gln Gly Thr Thr Val Thr Val Ser
    130                 135                 140

<210> SEQ ID NO 30
<211> LENGTH: 127
<212> TYPE: PRT
<213> ORGANISM: Homo sapiens

<400> SEQUENCE: 30

Met Glu Ala Pro Ala Gln Leu Leu Phe Leu Leu Leu Leu Trp Leu Pro
  1               5                  10                  15

Asp Thr Thr Gly Glu Ile Val Leu Thr Gln Ser Pro Ala Thr Leu Ser
             20                  25                  30

Leu Ser Pro Gly Glu Arg Ala Thr Leu Ser Cys Arg Ala Ser Gln Ser
         35                  40                  45

Val Ser Ser Tyr Leu Ala Trp Tyr Gln Gln Lys Pro Gly Gln Ala Pro
     50                  55                  60

Arg Leu Leu Ile Tyr Asp Ala Ser Asn Arg Ala Thr Gly Ile Pro Ala
 65                  70                  75                  80

Arg Phe Ser Gly Ser Gly Ser Gly Thr Asp Phe Thr Leu Thr Ile Ser
                 85                  90                  95

Ser Leu Glu Pro Glu Asp Phe Ala Val Tyr Tyr Cys Gln Gln Arg Ser
            100                 105                 110

Asn Trp Pro Ile Thr Phe Gly Gln Gly Thr Arg Leu Glu Ile Lys
        115                 120                 125

<210> SEQ ID NO 31
<211> LENGTH: 42
<212> TYPE: DNA
<213> ORGANISM: Artificial Sequence
<220> FEATURE:
<223> OTHER INFORMATION: primer

<400> SEQUENCE: 31
tggggagttt ttctcagagg aattcgatgg ttcacagttg ta                        42

<210> SEQ ID NO 32
<211> LENGTH: 23
<212> TYPE: DNA
<213> ORGANISM: Artificial Sequence
<220> FEATURE:
<223> OTHER INFORMATION: primer

<400> SEQUENCE: 32
tgtaacagta ttgggtagat ggg                                             23

<210> SEQ ID NO 33
<211> LENGTH: 23
<212> TYPE: DNA
<213> ORGANISM: Artificial Sequence
<220> FEATURE:
<223> OTHER INFORMATION: primer

<400> SEQUENCE: 33
aatcatggac atacttaata tta                                             23

<210> SEQ ID NO 34
```

<211> LENGTH: 41
<212> TYPE: DNA
<213> ORGANISM: Artificial Sequence
<220> FEATURE:
<223> OTHER INFORMATION: primer

<400> SEQUENCE: 34
tatagcccgg ggccgccacc atgacaacac ccagaaattc a    41

<210> SEQ ID NO 35
<211> LENGTH: 38
<212> TYPE: DNA
<213> ORGANISM: Artificial Sequence
<220> FEATURE:
<223> OTHER INFORMATION: primer

<400> SEQUENCE: 35
gcgtctcatg tacattaagg agagctgtca ttttctat    38

<210> SEQ ID NO 36
<211> LENGTH: 23
<212> TYPE: DNA
<213> ORGANISM: Artificial Sequence
<220> FEATURE:
<223> OTHER INFORMATION: primer

<400> SEQUENCE: 36
tcggacatct catgactttc ttt    23

<210> SEQ ID NO 37
<211> LENGTH: 23
<212> TYPE: DNA
<213> ORGANISM: Artificial Sequence
<220> FEATURE:
<223> OTHER INFORMATION: primer

<400> SEQUENCE: 37
gtagtctgag cagtactcgt tgc    23

<210> SEQ ID NO 38
<211> LENGTH: 42
<212> TYPE: DNA
<213> ORGANISM: Artificial Sequence
<220> FEATURE:
<223> OTHER INFORMATION: primer

<400> SEQUENCE: 38
tggggagttt ttctcagagg aattcgatgg ttcacagttg ta    42

<210> SEQ ID NO 39
<211> LENGTH: 42
<212> TYPE: DNA
<213> ORGANISM: Artificial Sequence
<220> FEATURE:
<223> OTHER INFORMATION: primer

<400> SEQUENCE: 39
tacaactgtg aaccatcgaa ttcctctgag aaaaactccc ca    42

<210> SEQ ID NO 40
<211> LENGTH: 23
<212> TYPE: DNA
<213> ORGANISM: Artificial Sequence
<220> FEATURE:
<223> OTHER INFORMATION: primer

<400> SEQUENCE: 40

-continued

```
tgtaacagta ttgggtagat ggg                                           23
```

<210> SEQ ID NO 41
<211> LENGTH: 23
<212> TYPE: DNA
<213> ORGANISM: Artificial Sequence
<220> FEATURE:
<223> OTHER INFORMATION: primer

<400> SEQUENCE: 41

```
aatcatggac atacttaata tta                                           23
```

<210> SEQ ID NO 42
<211> LENGTH: 15
<212> TYPE: PRT
<213> ORGANISM: Artificial Sequence
<220> FEATURE:
<223> OTHER INFORMATION: oligopeptide

<400> SEQUENCE: 42

Leu Met Ile Pro Ala Gly Ile Tyr Ala Pro Ile Ala Val Thr Val
1               5                   10                  15

<210> SEQ ID NO 43
<211> LENGTH: 15
<212> TYPE: PRT
<213> ORGANISM: Artificial Sequence
<220> FEATURE:
<223> OTHER INFORMATION: oligopeptide

<400> SEQUENCE: 43

Lys Ile Ser His Phe Leu Lys Met Glu Ser Leu Asn Phe Ile Arg
1               5                   10                  15

<210> SEQ ID NO 44
<211> LENGTH: 15
<212> TYPE: PRT
<213> ORGANISM: Artificial Sequence
<220> FEATURE:
<223> OTHER INFORMATION: oligopeptide

<400> SEQUENCE: 44

Lys Met Glu Ser Leu Asn Phe Ile Arg Ala His Thr Pro Tyr Ile
1               5                   10                  15

<210> SEQ ID NO 45
<211> LENGTH: 15
<212> TYPE: PRT
<213> ORGANISM: Artificial Sequence
<220> FEATURE:
<223> OTHER INFORMATION: oligopeptide

<400> SEQUENCE: 45

Met Glu Ser Leu Asn Phe Ile Arg Ala His Thr Pro Tyr Ile Asn
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: oligopeptide

<400> SEQUENCE: 46

Tyr Ile Asn Ile Tyr Asn Ala Glu Pro Ala Asn Pro Ser Glu Lys
1               5                   10                  15

```
<210> SEQ ID NO 47
<211> LENGTH: 15
<212> TYPE: PRT
<213> ORGANISM: Artificial Sequence
<220> FEATURE:
<223> OTHER INFORMATION: oligopeptide

<400> SEQUENCE: 47

Tyr Asn Ala Glu Pro Ala Asn Pro Ser Glu Lys Asn Ser Pro Ser
 1               5                  10                  15

<210> SEQ ID NO 48
<211> LENGTH: 15
<212> TYPE: PRT
<213> ORGANISM: Artificial Sequence
<220> FEATURE:
<223> OTHER INFORMATION: oligopeptide

<400> SEQUENCE: 48

Asn Ala Glu Pro Ala Asn Pro Ser Glu Lys Asn Ser Pro Ser Thr
 1               5                  10                  15

<210> SEQ ID NO 49
<211> LENGTH: 15
<212> TYPE: PRT
<213> ORGANISM: Artificial Sequence
<220> FEATURE:
<223> OTHER INFORMATION: oligopeptide

<400> SEQUENCE: 49

Glu Pro Ala Asn Pro Ser Glu Lys Asn Ser Pro Ser Thr Gln Tyr
 1               5                  10                  15

<210> SEQ ID NO 50
<211> LENGTH: 15
<212> TYPE: PRT
<213> ORGANISM: Artificial Sequence
<220> FEATURE:
<223> OTHER INFORMATION: oligopeptide

<400> SEQUENCE: 50

Pro Ala Asn Pro Ser Glu Lys Asn Ser Pro Ser Thr Gln Tyr Ala
 1               5                  10                  15

<210> SEQ ID NO 51
<211> LENGTH: 15
<212> TYPE: PRT
<213> ORGANISM: Artificial Sequence
<220> FEATURE:
<223> OTHER INFORMATION: oligopeptide

<400> SEQUENCE: 51

Asn Pro Ser Glu Lys Asn Ser Pro Ser Thr Gln Tyr Ala Tyr Ser
 1               5                  10                  15

<210> SEQ ID NO 52
<211> LENGTH: 15
<212> TYPE: PRT
<213> ORGANISM: Artificial Sequence
<220> FEATURE:
<223> OTHER INFORMATION: oligopeptide

<400> SEQUENCE: 52

Ser Glu Lys Asn Ser Pro Ser Thr Gln Tyr Ala Tyr Ser Ile Gln
 1               5                  10                  15
```

```
<210> SEQ ID NO 53
<211> LENGTH: 7
<212> TYPE: PRT
<213> ORGANISM: Artificial Sequence
<220> FEATURE:
<223> OTHER INFORMATION: oligopeptide

<400> SEQUENCE: 53

Asn Phe Ile Arg Ala His Thr
1               5

<210> SEQ ID NO 54
<211> LENGTH: 7
<212> TYPE: PRT
<213> ORGANISM: Artificial Sequence
<220> FEATURE:
<223> OTHER INFORMATION: oligopeptide

<400> SEQUENCE: 54

Phe Ile Arg Ala His Thr Pro
1               5

<210> SEQ ID NO 55
<211> LENGTH: 7
<212> TYPE: PRT
<213> ORGANISM: Artificial Sequence
<220> FEATURE:
<223> OTHER INFORMATION: oligopeptide

<400> SEQUENCE: 55

Ile Arg Ala His Thr Pro Tyr
1               5

<210> SEQ ID NO 56
<211> LENGTH: 7
<212> TYPE: PRT
<213> ORGANISM: Artificial Sequence
<220> FEATURE:
<223> OTHER INFORMATION: oligopeptide

<400> SEQUENCE: 56

Arg Ala His Thr Pro Tyr Ile
1               5

<210> SEQ ID NO 57
<211> LENGTH: 7
<212> TYPE: PRT
<213> ORGANISM: Artificial Sequence
<220> FEATURE:
<223> OTHER INFORMATION: oligopeptide

<400> SEQUENCE: 57

His Phe Leu Lys Met Glu Ser
1               5

<210> SEQ ID NO 58
<211> LENGTH: 7
<212> TYPE: PRT
<213> ORGANISM: Artificial Sequence
<220> FEATURE:
<223> OTHER INFORMATION: oligopeptide

<400> SEQUENCE: 58

Phe Leu Lys Met Glu Ser Leu
1               5
```

```
<210> SEQ ID NO 59
<211> LENGTH: 7
<212> TYPE: PRT
<213> ORGANISM: Artificial Sequence
<220> FEATURE:
<223> OTHER INFORMATION: oligopeptide

<400> SEQUENCE: 59

Leu Lys Met Glu Ser Leu Asn
1               5

<210> SEQ ID NO 60
<211> LENGTH: 7
<212> TYPE: PRT
<213> ORGANISM: Artificial Sequence
<220> FEATURE:
<223> OTHER INFORMATION: oligopeptide

<400> SEQUENCE: 60

Lys Met Glu Ser Leu Asn Phe
1               5

<210> SEQ ID NO 61
<211> LENGTH: 7
<212> TYPE: PRT
<213> ORGANISM: Artificial Sequence
<220> FEATURE:
<223> OTHER INFORMATION: oligopeptide

<400> SEQUENCE: 61

Met Glu Ser Leu Asn Phe Ile
1               5

<210> SEQ ID NO 62
<211> LENGTH: 7
<212> TYPE: PRT
<213> ORGANISM: Artificial Sequence
<220> FEATURE:
<223> OTHER INFORMATION: oligopeptide

<400> SEQUENCE: 62

Glu Pro Ala Asn Pro Ser Glu
1               5

<210> SEQ ID NO 63
<211> LENGTH: 7
<212> TYPE: PRT
<213> ORGANISM: Artificial Sequence
<220> FEATURE:
<223> OTHER INFORMATION: oligopeptide

<400> SEQUENCE: 63

Pro Ala Asn Pro Ser Glu Lys
1               5

<210> SEQ ID NO 64
<211> LENGTH: 7
<212> TYPE: PRT
<213> ORGANISM: Artificial Sequence
<220> FEATURE:
<223> OTHER INFORMATION: oligopeptide

<400> SEQUENCE: 64

Ala Asn Pro Ser Glu Lys Asn
1               5

<210> SEQ ID NO 65
```

```
<211> LENGTH: 7
<212> TYPE: PRT
<213> ORGANISM: Artificial Sequence
<220> FEATURE:
<223> OTHER INFORMATION: oligopeptide

<400> SEQUENCE: 65

Asn Pro Ser Glu Lys Asn Ser
1               5

<210> SEQ ID NO 66
<211> LENGTH: 7
<212> TYPE: PRT
<213> ORGANISM: Artificial Sequence
<220> FEATURE:
<223> OTHER INFORMATION: oligopeptide

<400> SEQUENCE: 66

Pro Ser Glu Lys Asn Ser Pro
1               5

<210> SEQ ID NO 67
<211> LENGTH: 7
<212> TYPE: PRT
<213> ORGANISM: Artificial Sequence
<220> FEATURE:
<223> OTHER INFORMATION: oligopeptide

<400> SEQUENCE: 67

Ser Glu Lys Asn Ser Pro Ser
1               5

<210> SEQ ID NO 68
<211> LENGTH: 7
<212> TYPE: PRT
<213> ORGANISM: Artificial Sequence
<220> FEATURE:
<223> OTHER INFORMATION: oligopeptide

<400> SEQUENCE: 68

Glu Lys Asn Ser Pro Ser Thr
1               5

<210> SEQ ID NO 69
<211> LENGTH: 7
<212> TYPE: PRT
<213> ORGANISM: Artificial Sequence
<220> FEATURE:
<223> OTHER INFORMATION: oligopeptide

<400> SEQUENCE: 69

Lys Asn Ser Pro Ser Thr Gln
1               5

<210> SEQ ID NO 70
<211> LENGTH: 7
<212> TYPE: PRT
<213> ORGANISM: Artificial Sequence
<220> FEATURE:
<223> OTHER INFORMATION: oligopeptide

<400> SEQUENCE: 70

Asn Ser Pro Ser Thr Gln Tyr
1               5

<210> SEQ ID NO 71
<211> LENGTH: 7
```

```
<212> TYPE: PRT
<213> ORGANISM: Artificial Sequence
<220> FEATURE:
<223> OTHER INFORMATION: oligopeptide

<400> SEQUENCE: 71

Pro Ala Gly Ile Ala Tyr Pro
 1               5

<210> SEQ ID NO 72
<211> LENGTH: 7
<212> TYPE: PRT
<213> ORGANISM: Artificial Sequence
<220> FEATURE:
<223> OTHER INFORMATION: oligopeptide

<400> SEQUENCE: 72

Ala Gly Ile Tyr Ala Pro Ile
 1               5

<210> SEQ ID NO 73
<211> LENGTH: 99
<212> TYPE: PRT
<213> ORGANISM: Homo sapiens

<400> SEQUENCE: 73

Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp

<210> SEQ ID NO 74
<211> LENGTH: 123
<212> TYPE: PRT
<213> ORGANISM: Homo sapiens

<400> SEQUENCE: 74

Ala Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Gly Asp Tyr
            20                  25                  30

Thr Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Thr Lys Asp Asn Gln Tyr Gly Ser Gly Ser Thr Tyr Gly Leu Gly Val
                100                 105                 110
```

```
Trp Gly Gln Gly Thr Leu Val Thr Val Ser Ser
            115                 120

<210> SEQ ID NO 75
<211> LENGTH: 95
<212> TYPE: PRT
<213> ORGANISM: Homo sapiens

<400> SEQUENCE: 75

Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Tyr
                 20                  25                  30

Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro
                 85                  90                  95

<210> SEQ ID NO 76
<211> LENGTH: 107
<212> TYPE: PRT
<213> ORGANISM: Homo sapiens

<400> SEQUENCE: 76

Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Tyr
                 20                  25                  30

Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Leu
                 85                  90                  95

Thr Phe Gly Gly Gly Thr Lys Val Glu Ile Lys
            100                 105

<210> SEQ ID NO 77
<211> LENGTH: 107
<212> TYPE: PRT
<213> ORGANISM: Homo sapiens

<400> SEQUENCE: 77

Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Tyr
                 20                  25                  30

Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
 50                  55                  60
```

-continued

```
Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asp Trp Pro Leu
                 85                  90                  95

Thr Phe Gly Gly Gly Thr Lys Val Glu Ile Lys
            100                 105

<210> SEQ ID NO 78
<211> LENGTH: 95
<212> TYPE: PRT
<213> ORGANISM: Homo sapiens

<400> SEQUENCE: 78

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Ser Ser Trp
                 20                  25                  30

Leu Ala Trp Tyr Gln Gln Lys Pro Glu Lys Ala Pro Lys Ser Leu Ile
             35                  40                  45

Tyr Ala Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro
                 85                  90                  95

<210> SEQ ID NO 79
<211> LENGTH: 106
<212> TYPE: PRT
<213> ORGANISM: Homo sapiens

<400> SEQUENCE: 79

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Ser Ser Trp
                 20                  25                  30

Leu Ala Trp Tyr Gln Gln Lys Pro Glu Lys Ala Pro Lys Ser Leu Ile
             35                  40                  45

Tyr Ala Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Val Phe Thr
                 85                  90                  95

Phe Gly Pro Gly Thr Lys Val Asp Ile Lys
            100                 105
```